US006652808B1

(12) United States Patent
Heller et al.

(10) Patent No.: US 6,652,808 B1
(45) Date of Patent: *Nov. 25, 2003

(54) METHODS FOR THE ELECTRONIC ASSEMBLY AND FABRICATION OF DEVICES

(75) Inventors: Michael J. Heller, Encinitas, CA (US); Jeffrey M. Cable, Temecula, CA (US); Sadik C. Esener, Solana Beach, CA (US)

(73) Assignees: Nanotronics, Inc., San Diego, CA (US); The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/760,933

(22) Filed: Dec. 6, 1996

Related U.S. Application Data

(63) Continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,696, which is a continuation-in-part of application No. 08/146,504, filed on Nov. 1, 1993, now Pat. No. 5,605,662, which is a continuation-in-part of application No. 08/703,601, filed on Aug. 23, 1996, now Pat. No. 5,849,489, which is a continuation of application No. 08/232,233, filed on May 5, 1994, now Pat. No. 5,565,322, which is a continuation-in-part of application No. 07/790,262, filed on Nov. 7, 1991, now abandoned, which is a continuation of application No. 08/250,951, filed on May 27, 1994, now Pat. No. 5,532,129, and a continuation of application No. 08/258,168, filed on Jun. 10, 1994, now Pat. No. 5,787,032.

(51) Int. Cl.$^7$ .......................... G01N 15/00; C12Q 1/68; C12P 19/34

(52) U.S. Cl. .......................... 422/68.1; 435/6; 435/91.1

(58) Field of Search .................. 422/287, 68.1, 422/50, 76, 82.01, 82.02, 82.05; 435/6.5, 91.1, 7.1, 7.2; 204/456; 436/149, 150, 806, 807; 530/300, 350, 333; 536/24.3, 24.32, 24.33, 23.1

(56) References Cited

U.S. PATENT DOCUMENTS 3,950,738 A   4/1976   Hayashi et al. ....... 340/173 LS (List continued on next page.)

FOREIGN PATENT DOCUMENTS

EP   0228075   7/1987

(List continued on next page.)

OTHER PUBLICATIONS

Niemeyer Angew Chem. Int. Ed Engl. 36: 585–587 (of interest), 1997.*

(List continued on next page.)

*Primary Examiner*—Ardin H. Marschel
(74) *Attorney, Agent, or Firm*—O'Melveny & Myers LLP

(57) ABSTRACT

Methods provide for electric field assisted self-assembly of functionalized programmable nucleic acids, nucleic acid modified structures, and other selective affinity or binding moieties as building blocks for: creating molecular electronic and photonic mechanisms; organization, assembly, communication and interconnection of nanostructures, submicron and micron sized components onto silicon or other materials; organization, assembly, communication and interconnection of nanostructures, submicron and micron sized components within parameters of microelectronic or opto-electronic components and devices; creating, arraying, and manufacturing photonic and electronic structures, devices, and systems. Methods for the fabrication of microscale and nanoscale devices include the steps of: releasing at least one component device from a support, transporting at least one component device to a support, and attaching at least one component device to the support. Optionally, the methods may further include the step of fabricating at least one component device on a first support.

126 Claims, 46 Drawing Sheets

U.S. PATENT DOCUMENTS

| | | | | |
|---|---|---|---|---|
| 3,995,190 A | | 11/1976 | Salgo | 422/50 |
| 4,032,901 A | | 6/1977 | Levinthal | 340/173 NC |
| 4,563,419 A | | 1/1986 | Ranki et al. | 435/6 |
| 4,580,895 A | | 4/1986 | Patel | 356/39 |
| 4,584,075 A | | 4/1986 | Goldstein et al. | 204/182.3 |
| 4,594,135 A | | 6/1986 | Goldstein | 204/180.1 |
| 4,599,303 A | * | 7/1986 | Yabusaki et al. | 435/6 |
| 4,728,724 A | | 3/1988 | Jones et al. | 430/19 |
| 4,731,325 A | * | 3/1988 | Palva et al. | 435/6 |
| 4,751,177 A | | 6/1988 | Stabinsky | 435/6 |
| 4,787,963 A | | 11/1988 | MacConnell | 204/180.1 |
| 4,804,625 A | | 2/1989 | Morrison et al. | 435/7 |
| 4,816,418 A | | 3/1989 | Mack et al. | 436/518 |
| 4,822,566 A | | 4/1989 | Newman | 422/68 |
| 4,822,746 A | | 4/1989 | Walt | 436/528 |
| 4,824,776 A | | 4/1989 | Heller et al. | 435/6 |
| 4,859,583 A | | 8/1989 | Heller et al. | 435/7 |
| 4,868,103 A | | 9/1989 | Stavrianopoulos et al. | 435/5 |
| 4,908,112 A | | 3/1990 | Pace | 204/299 R |
| 4,908,453 A | * | 3/1990 | Cocuzza | 548/113 |
| 4,996,143 A | | 2/1991 | Heller | 435/6 |
| 5,063,081 A | | 11/1991 | Cozzette et al. | 427/2 |
| 5,075,077 A | | 12/1991 | Durley, III et al. | 422/56 |
| 5,096,807 A | | 3/1992 | Leaback | 435/6 |
| 5,125,748 A | | 6/1992 | Bjornson et al. | 356/414 |
| 5,126,022 A | | 6/1992 | Soane et al. | 204/180.1 |
| 5,143,854 A | | 9/1992 | Pirrung et al. | 436/518 |
| 5,164,319 A | | 11/1992 | Hafeman et al. | 435/91 |
| 5,166,063 A | | 11/1992 | Johnson | 435/173 |
| 5,200,051 A | | 4/1993 | Cozzette et al. | 530/350 |
| 5,202,231 A | | 4/1993 | Drmanac et al. | 435/6 |
| 5,219,726 A | | 6/1993 | Evans | 435/6 |
| 5,227,265 A | | 7/1993 | DeBoer et al. | 430/41 |
| 5,231,626 A | | 7/1993 | Tadokoro et al. | 369/121 |
| 5,234,565 A | | 8/1993 | Osman et al. | 204/403 |
| 5,304,487 A | | 4/1994 | Wilding et al. | 422/68.1 |
| 5,312,527 A | | 5/1994 | Mikkelsen et al. | 204/153.12 |
| 5,316,900 A | | 5/1994 | Tsujioka et al. | 430/495 |
| 5,346,789 A | | 9/1994 | Lewis et al. | 430/19 |
| 5,355,577 A | | 10/1994 | Cohn | 29/592.1 |
| 5,380,833 A | * | 1/1995 | Urdea | 536/22.1 |
| 5,399,451 A | | 3/1995 | Hashida et al. | 430/19 |
| 5,405,783 A | * | 4/1995 | Pirrung et al. | 436/518 |
| 5,434,049 A | | 7/1995 | Okano et al. | 435/6 |
| 5,505,700 A | * | 4/1996 | Leone et al. | |
| 5,565,322 A | | 10/1996 | Heller | 435/6 |
| 5,567,811 A | * | 10/1996 | Misiura et al. | 536/25.34 |
| 5,637,458 A | * | 6/1997 | Frankel et al. | |
| 5,741,462 A | * | 4/1998 | Nova et al. | 422/68.1 |
| 5,751,629 A | * | 5/1998 | Nova et al. | 365/151 |
| 5,789,167 A | * | 8/1998 | Konrad | 435/6 |
| 5,795,714 A | * | 8/1998 | Cantor et al. | |
| 5,874,214 A | * | 2/1999 | Nova et al. | 435/6 |
| 5,925,562 A | * | 7/1999 | Nova et al. | 435/287.1 |
| 5,964,410 A | * | 10/1999 | Chow et al. | |
| 5,972,187 A | * | 10/1999 | Parce et al. | |
| 6,025,129 A | * | 2/2000 | Nova et al. | 435/6 |

FOREIGN PATENT DOCUMENTS

| | | |
|---|---|---|
| EP | 0229943 | 7/1987 |
| EP | 0 617 303 A | 9/1994 |
| GB | 2156074 | 10/1985 |
| WO | 8603782 | 7/1986 |
| WO | WO88/08528 | 11/1988 |
| WO | WO89/01159 | 2/1989 |
| WO | 8910977 | 11/1989 |
| WO | 9001564 | 2/1990 |
| WO | WO92/044770 | 3/1992 |
| WO | WO93/09128 | 5/1993 |
| WO | WO93/21663 | 10/1993 |
| WO | WO93/22678 | 11/1993 |
| WO | WO95/07363 | 3/1995 |
| WO | WO96/01836 | 1/1996 |
| YU | 57087 | 8/1990 |

OTHER PUBLICATIONS

Dagani C& EN pp. 20–23 (of interest), Dec. 2, 1996.*
Stroscio et al. Science 254: 1319–1326 (of interest), 1991.*
Whitesides et al. Science 254:1312–1318 (of interest), 1994.*
Callahan et al., Electronics Letters, 29, pp 951–953, 1993.*
Matthews et al., Analytical Biochemistry, vol. 169, pp 1–25, 1988.*
Misiura et al., Nucleic Acids Research, vol. 18, No. 15, pp. 4345–4354, 1990.*
Mizuno, "The Organic Chemistry of Nucleic Acids", [published by Elsevier, Tokyo, (1986)] pp. 181–200.*
Anand and Southern "Pulsed Field Gel Electrophoresis," Gel Electrophoresis of Nucleic Acids—A Practical Approach, 2d. Ed., D. Rickwood and B.D. Hames (New York:IRL Press 1990), pp 101–123.
Anderson and Young, "Quantitative Filter Hybridization," Nucleic Acid Hybridization—A Practical Approach, Eds. B.D. Hames and S.J. Higgins (Washington, D.C. :IRL Press 1985) pp 73–111.
Baines, "Setting a Sequence to Sequence a Sequence," Bio/Technology, 10:757–758 (1992).
Barinaga, "Will 'DNA Chip' Speed Genome Initiative?", Science, 253:1489 (1991).
Beattie et al., "Genosensor Technology," The 1992 San Diego Conference: Genetic Recognition, pp 1–5 (Nov., 1992).
Beltz et al., "Isolation of Multigene Families and Determination of Homologies by Filter Hybridization Methods," Methods in Enzymology, 100:266–285 (1983).
Connor et al., "Detection of Sickle Cell $\beta^3$–Globin Allele by Hybridization With Synthetic Oligonucleotides," Proc. Natl. Acad. Sci. USA, 80:278–282 (1983).
Drmanac et al., "Sequencing of Megabase Plus DNA by Hybridization: Theory of the Method," Genomics, 4:114–128 (1989).
Drmanac et al., "DNA Sequence Determination by Hybridixation: A Strategy for Efficient Large–Scale Sequencing," Science, 260: 1649–1652 (1993).
Fodor et al., "Multiplexed Biochemical Assays With Biological Chips," Nature, 364:555–556 (1993).
Fodor et al., "Light–Directed, Spatially Addressable Parallel Chemical Synthesis," Science, 251:767–773 (1991).
Horejsi, "Some Theoretical Aspects of Affinity Electrophoresis," Journal of Chromatography, 178:1–13 (1979).
Horjsi et al., Determination of Dissociation Constants of Lectin Sugar Complexes by Means of Affinity Electrophoresis, Biochimica at Biophysica Acta, 499:200–300 (1977).
Ranki et al., "Sandwich Hybridization as a Convenient Method for the Detection of Nucleic Acids in Crude Samples," Gene, 21:77–85 (1983).
Saiki, "Amplification of Genomic DNA," PCR Protocols: A Guide to Methods and Applications, (Academic Press, Inc. 1990), pp 13–20.
Southern et al., "Analyzing and Comparing Nucleic Acid Sequences by Hybridization to Arrays of Oligonucleotides Evaluation Using Experimental Models," Genomics, 13:1008–1017 (1992).
Strezoska et al., "DNA Sequencing by Hybridization: 100 Bases Read by a Non–Gel–Based Method", Proc. Natl. Acad. Sci. USA, 88:10089–93 (1991).

Wallace et al., "Hybridization of Synthetic Oligodcoxyribonucleotides to Φx 174 DNA: The Effect of Single Base Pair Mismatch," *Nucleic Acid Res.*, 6:3543–3557 (1979).

Washizu, "Electrostatic Manipulation of Biological Objects," *Journal of Electrostatics*, 25:109–123 (1990).

Washizu and Kurosawa, "Electrostatic Manipulation of DNA in Microfabricated Structures," *IEEE Transactions on Industry Applications*, 26:1165–1172 (1990).

Brown et al., "Electrochemically Induced Adsorption of Radio–Labelled DNA on Gold and HOPG Substrates for STM Investigations," *Ultramicroscopy*, 38 (1991) pp 253–264.

Palacek, "New Trends in Electrochemical Analysis of Nucleic Acids", *Bioelectrochemistry and Bioenergetics*, 20 (1988) pp 179–194.

Kornberg, Arthur, "DNA Synthesis", 1974.

Cardullo et al., *Proc. Nat. Acad. Sci. USA*, 85:8790–8794 (1988).

Garner et al, *Anal. Chem.*, 62:2193–2198 (1990).

Haddon et al., *Proc. Natl. Acad. Sci. USA*, 92:1874–1878 (1985).

Heller et al., "Rapid Detection and Infection of Infectious Diseases", Kingsbury et al., eds. Acad Pr, NY, pp 245–256 (1985).

Hopfield et al., *Science* 241:817–820 (1988).

Keller et al., "DNA Probes", pp 104–108, Stockton Press, N.Y. (1989).

McAlear et al., "Molecular Electronic Devices II", pp 623–633, Carter, e.d., Marcel Dekker, Inc., N.Y. (1987).

Morrison et al., *Anal. Biochem.*, 183:231–244 (1989).

Robinson et al., *Protein Eng.*, 1:295–300 (1987).

Glazer et al., *Emerging Techniques* Physofluor Probes, Trends in Biochemical Sciences, vol. 9, No. 10, pp 423 (1984).

Halfhill, Tom, R., "New Memory Architectures to Boost Performance", *Byte*, Jul., 1993, pp 86–87.

"An Active Microelectronic Device for Multiplex DNA Analysis", IEEE Engineering in Medicine and Biology, pp 100–104, Mar./Apr. 1996.

"Use of Thiazole Orange Homodimer as an Alternative to Ethidium Bromide for DNA Detection in Agarose Gels", *Modern Pathology*, vol. 7, #3, pp 385–387 (1994).

"Oncogene Amplification Screening by Labeled Primer Multiplex Polymerization Chain Reaction", *Modern Pathology*, vol. 7, #7, pp 784–789 (1994).

Heller, M.J. et al., "Fluorescent Detection Methods in PCR Analysis", *The Polymerase Chain Reaction*, Mullis et al. eds., Birkhanuser, 1994.

Heller, M.J. et al, "Microelectrophoresis for the Separation of DNA Fragments," *Electrophoresis*, #13, pp 512–520 (1992).

"Multiplex Polymerase Chain Reaction", *Modern Pathology*, v. 5, #3, pp 320–323, 1992.

Heller et al., "Self–Organizing Structures Based on Functionalized Synthetic Nucleic Acid Polymers", *Nanotechnology*, #2, pp 165–171 (1991).

Heller et al., "Chemiluminescent and Fluorescent DNA Probes in Hybridization Systems", *Rapid Detection and Identification of Infectious Agents*, Kingsbury et al. eds., Academic Press, New York, pp 345–365 (1985).

Heller et al., "Interactions of Miracil D with Double–Stranded Polyadenylic Acid and Polyuridylic Acid", *Biochemistry*, vol. 13, 1623, 1974.

Tu et al., "Structure and Stability of Metal Nucleoside Phosphate Complexes", *Metal Ions and Biological Systems*, e.d. Siegel, vol. 1, Ch 1, Marcel Dekker, Inc. 1974.

Heller et al., "Interaction of Divalent Manganese Ion With Adenosine Triphosphate and Related Compounds", *Biochemistry*. vol. 9, #25, 4970, 1970.

Esener et al, "Punch–Through Current Under Diffusion Limited Injection: Analysis and Applications,", *J. Appl. Phys.* (12), pp 1380–87, Aug. 1985.

Esener et al., "Design Considerations for Three–Terminal Optically Addressed MQW Spatial Light Modulators," presented at the Annual Meeting of OSA, at Seattle, Oct., 1986.

Esener et al.. "One–Dimension Silicon/PLZT Spatial Light Modulators," *Opt. Eng.* 26, (5) pp 406–413, May 1987, also in Proc. SPIE Annual Meeting in San Diego, Aug. 1986.

Feldman et al, "A Comparison of Electrical and Free Space Optical Interconnections," Appln. Opt. 27, pp 1742–51, 1988.

Lin et al., "Two–Dimensional Spatial Light Modulators Fabricated in Si/PLZT," *Appl. Opt.* 29 (11) 1595, Apr. 1990.

Krishnakumar et al., "Deposition and Characterization of Thin Ferroelectric Lead Lanthanum Zirconate Titanate (PLZT) Films on Sapphire for Spatial Light Modulators Applications", *IEEE Transactions on Ultrasonics Ferroelectrics and Frequency Control*, 38 (6), pp 585–90, Nov., 1991.

Fan et al., "Fundamental Bandgap and Schottky Barrier Height of Quaternary InAlGaAs Grown on GaAs," MRS Meeting, Spring, 1992.

Fan et al., "Quantum–Confined Stark Effect Modulators at 1.06 $\mu$m on GaAs", Accepted for publication *IEEE Photonics Technology Letter*, Dec., 1993.

Yu et al., "A Novel InGaAs PIN Photodiode on Semi–Insulating InP", *Optical and Quantum Electronics*, 18, pp 174–177, 1986.

Yu et al., "High–Speed, Self–Passivated InGaAs PIN Photodiode for Microwave Fiber Links", *Electron. Lett.*, 23, pp 571–572, 1987.

Yu et al., "Self–Aligned Diffusion Technique for n–Imp JFETs", *Electron. Lett.*, 23, pp 981–982, 1987.

Lee et al., "Interfacial Properties of InAlAs/InGaAs HIGH-FETs and MIS Capacitors", *Semiconductor Science and Technology*, 5, pp 716–720, 1990.

Krishnakumar et al., "Deposition and Characterization of Thin Ferroelectric Lead lanthanum Zirconate Titanate (PLZT) Films on Sapphire for Spatial Light Modulators Applications", *IEEE Transactions on Ultrasonics*, Ferroelectrics and Frequency Control, 38 (6), pp 585–590, Nov., 1991.

Shih et al., "Quantum–Confined Stark Effective Modulators at 1.06 $\mu$m on GaAs", *IEEE Photonics Technology Letter*, 5, No. 12, pp 1383–1385, Dec. 1993.

Shih et al., "Integration of InAlGaAs/InGaAs MODFETs on MQW Modulators on GaAs Substrates", *Electronics Letters*, 30 No. 20, Sep. 1994.

Mansoorian et al., "A Comparison of Transmitter Technologies for Digital Free–Space Optical Interconnections", Submitted to *Applied Optics*, Jul. 1994.

Heller, M.J., "An Active Microelectronics Device for Multiplex DNA Analysis", IEEE Engineering in Medicine and Biology Magazine, vol. 15, No. 2, Mar. 1, 1996, pp 100–104.

* cited by examiner

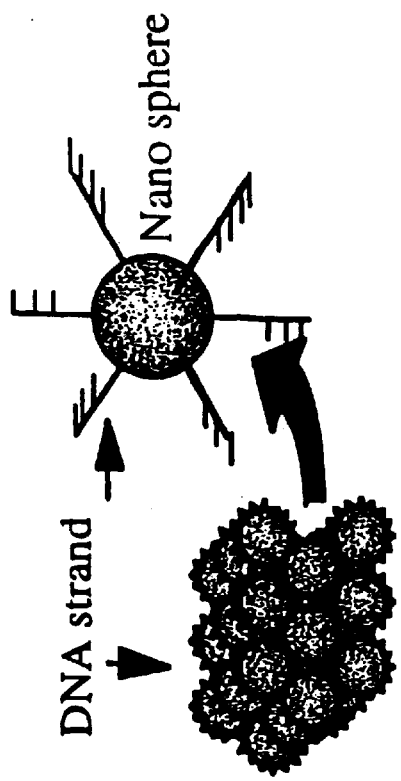
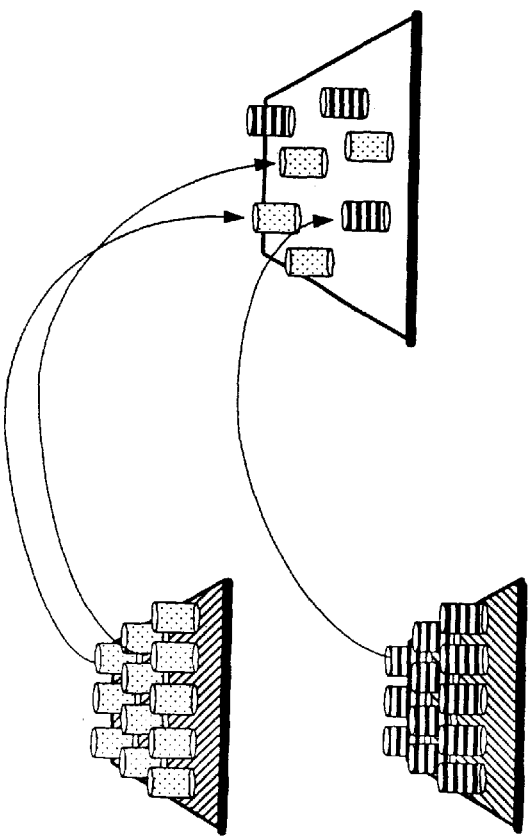
FIG. 3B.
FIG. 3A.

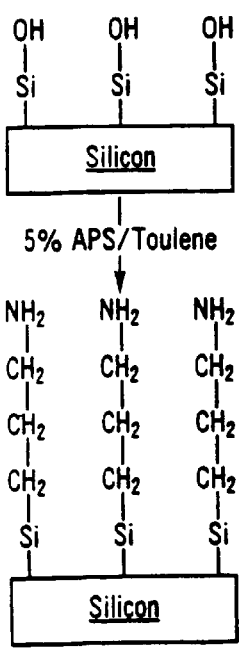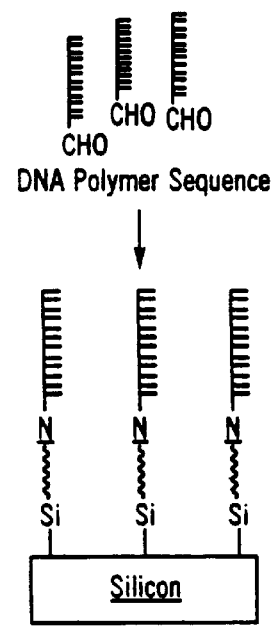
FIG. 4.

PROCESS FOR PREPARING FOUR ID DNA WRITE MATERIAL
THE DNA WITH SEQUENCE (A) IDENTITY IS BOUND COVALENTLY TO THE ENTIRE SURFACE

PROCESS FOR PREPARING FOUR ID DNA WRITE MATERIAL

DNA SEQUENCE (B) FUNCTIONALIZED WITH A PSORALEN MOLECULE IS HYBRIDIZED TO SEQUENCE (A) LEAVING AN UNHYBRIDIZED OVERHANG SEQUENCE FOR SUBSEQUENT HYBRIDIZATION

FIG. 11

LOCATION #1 IS MASKED FROM UV EXPOSURE WHILE LOCATIONS 2,3 &4 ARE EXPOSED ALLOWING THE PSORALEN MOLECULES TO COVALENTLY CROSS-LINK THE (A) AND (B) DNA SEQUENCE.

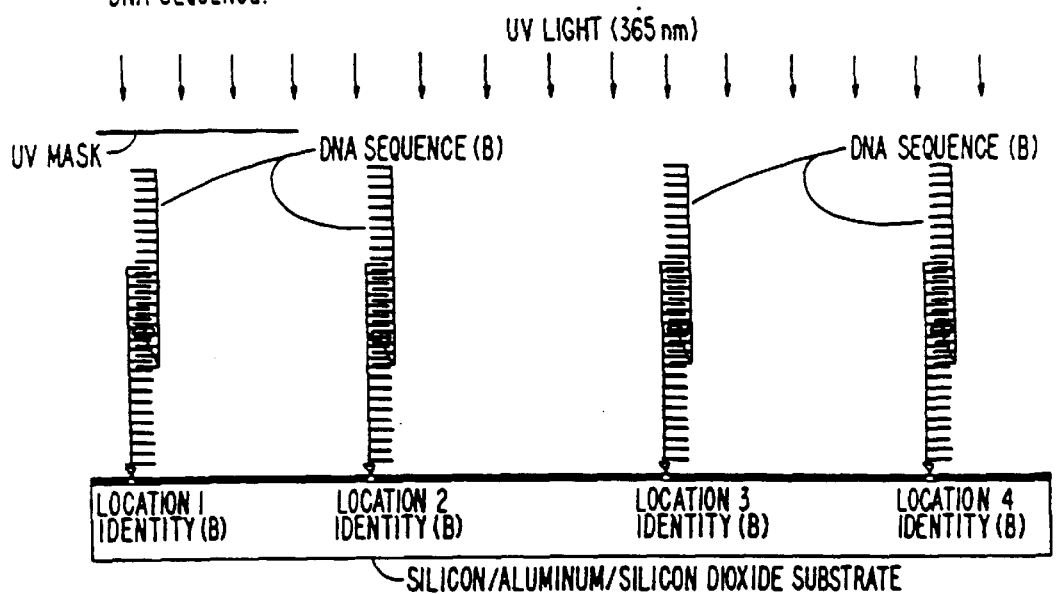

FIG. 12

PROCESS FOR PREPARING FOUR ID DNA WRITE MATERIAL

DEHYBRIDIZATION IS CARRIED OUT TO REMOVE THE NON-CROSSLINKED SEQUENCE (B) FROM THE 1st LOCATION, WHICH NOW HAS A PERMANENT (A) SEQUENCE IDENTITY. DNA SEQUENCE (B) IS NOW COVALENTLY COUPLED TO LOCATIONS 2, 3 AND 4

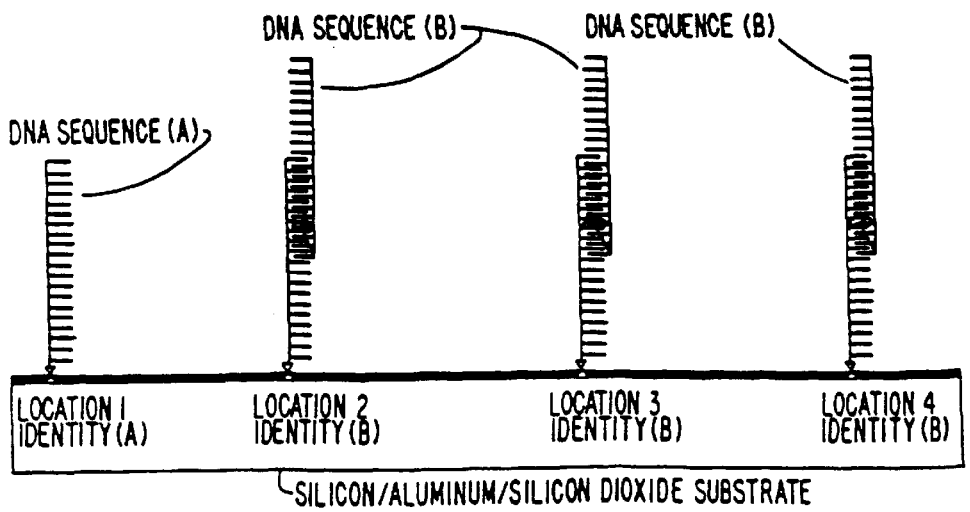

PROCESS FOR PREPARING FOUR ID DNA WRITE MATERIAL

A PSORALEN FUCTIONALIZED DNA SEQUENCE (C) IS NOW HYBRIDIZED TO SEQUENCE (B), AND THE PROCESS IS REPEATED.

PROCESS FOR PREPARING FOUR ID DNA WRITE MATERIAL

LOCATIONS 1 AND 2 ARE NOW MASKED WHILE LOCATIONS 3 AND 4 ARE EXPOSED AFFECTING THE COVALENT CROSS-LINKING OF SEQUENCES (B) AND (C).

PROCESS FOR PREPARING FOUR ID DNA WRITE MATERIAL

DEHYBRIDIZATION IS CARRIED OUT TO REMOVE SEQUENCE (C) FROM LOCATION 2. A PERMANENT (B) DNA SEQUENCE IDENTITY IS NOW PRESENT AT LOCATION 2

PROCESS FOR PREPARING FOUR ID DNA WRITE MATERIAL

A PSORALEN FUCTIONALIZED DNA SEQUENCE (D) IS NOW HYBRIDIZED TO SEQUENCE (C), AND THE PROCESS IS REPEATED.

PROCESS FOR PREPARING FOUR ID DNA WRITE MATERIAL

DEHYBRIDIZATION IS CARRIED OUT TO REMOVE DNA SEQUENCE (D) FROM LOCATION 3. A PERMANENT (C) IDENTITY IS PRESENT AT LOCATION 3 AND A PERMANENT (D) IDENTITY IS PRESENT AT LOCATION 4. THIS COMPLETES THE PROCESS FOR PREPARING A FOUR ID DNA WRITE MATERIAL.

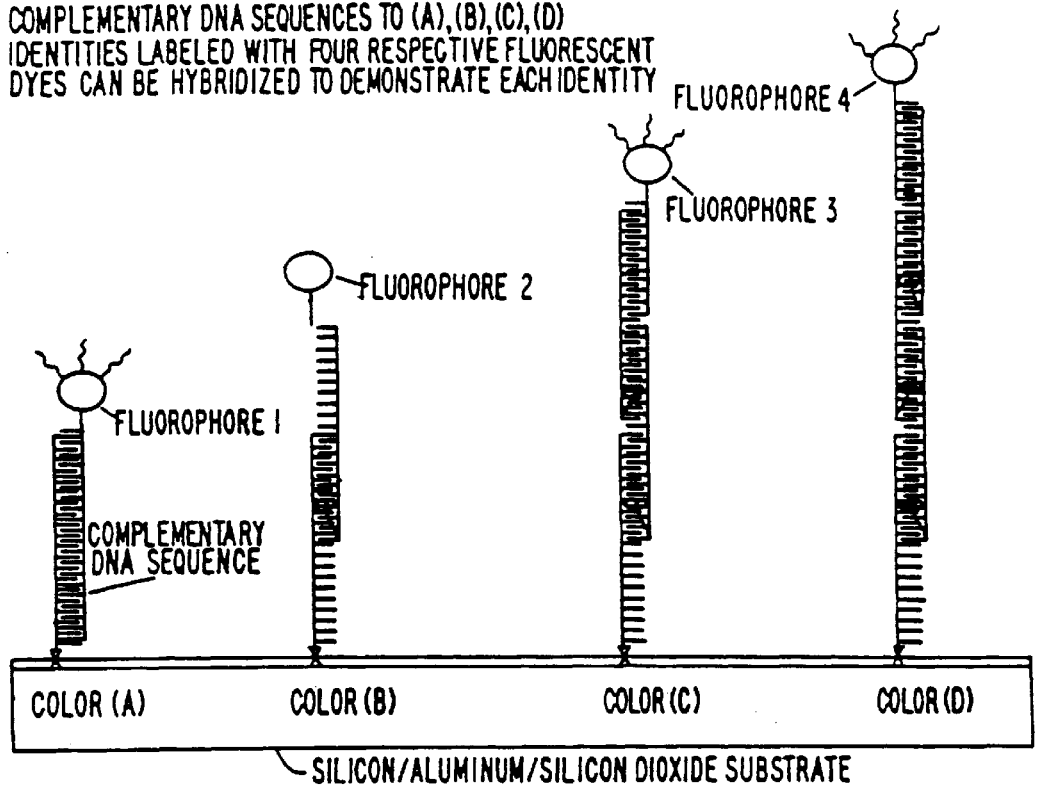

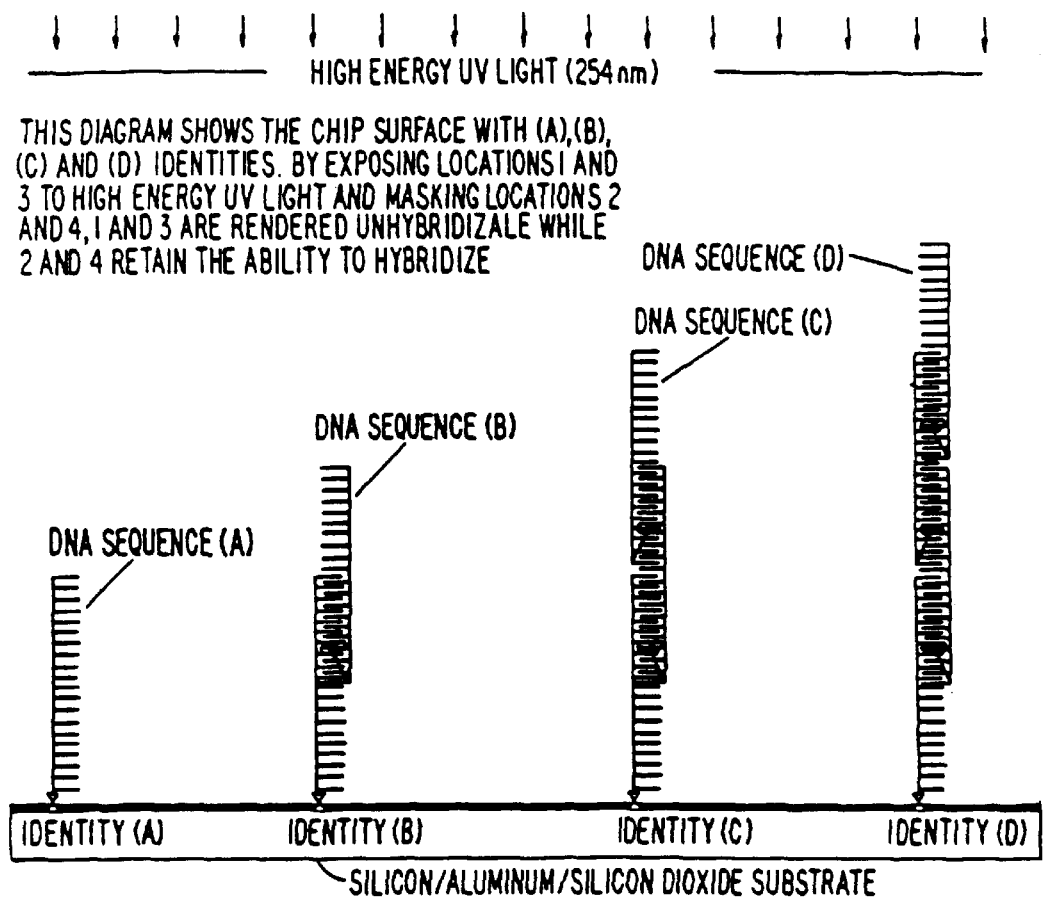

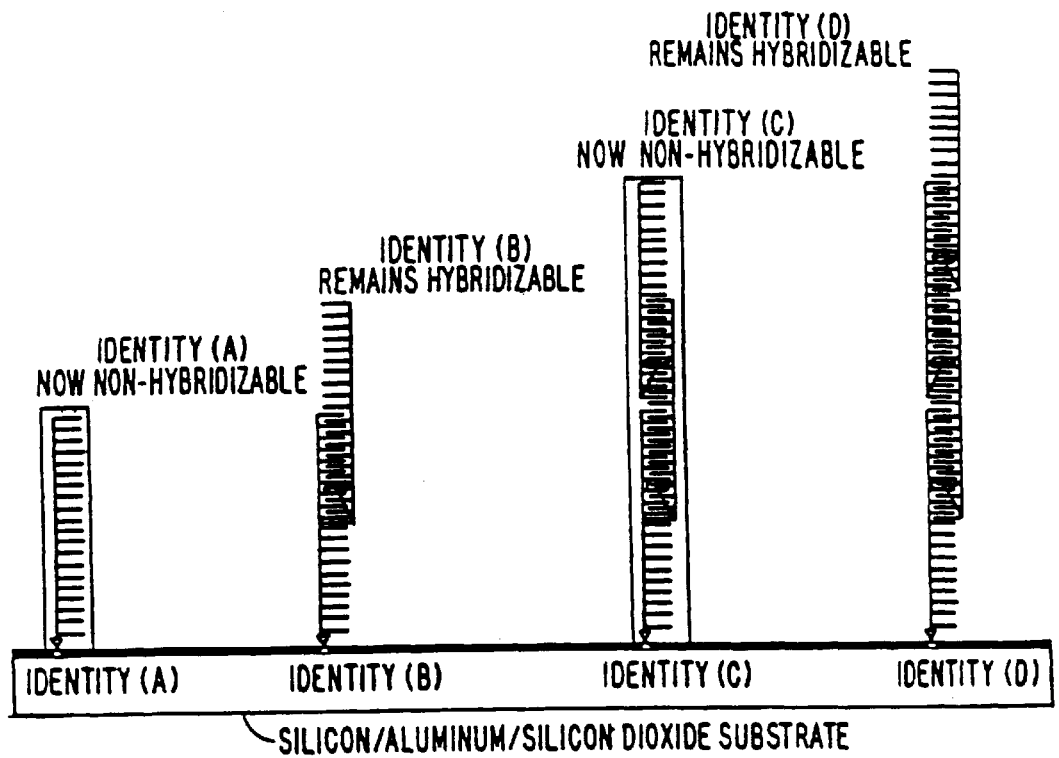

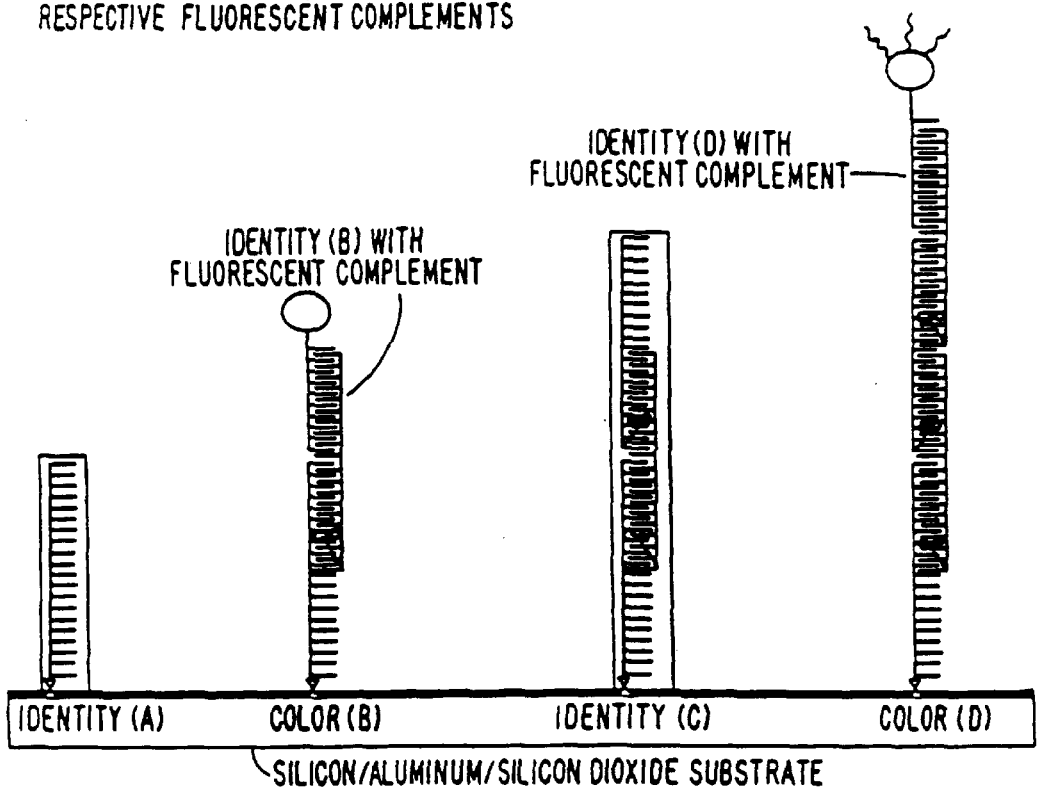

CHIP SURFACE IS FUNCTIONALIZED ONLY WITH APS

ORIGINAL CAPTURE DNA SEQUENCE A, WHICH IS NOT FLUORESCENTLY LABELED, IS COVALENTLY ATTACHED TO THE APS LAYER ON THE CHIP SURFACE

FLUORESCENTLY LABELED COMPLEMENTARY DNA SEQUENCE TO THE (A) IDENTITY ON THE SURFACE IS HYBRIDIZED TO THE ENTIRE CHIP LEAVING THE ENTIRE SURFACE BRIGHT

1/2 OF SURFACE IS UV CROSSLINKED SO WHEN THE BODIPY TEXAS RED LABELED (A) IDENTITY COMPLEMENT IS HYBRIDIZED ACROSS THE ENTIRE CHIP ONLY THE NON-CROSSLINKED RIGHT SIDE OF THE CHIP ATTAINS COLOR

AFTER UV CROSSLINKING THE BODIPY ORANGE LABELED (B) DNA COMPLEMENT IS HYBRIDIZED LEAVING ONLY THE (B) IDENTITY LEFT SIDE OF THE CHIP BRIGHT

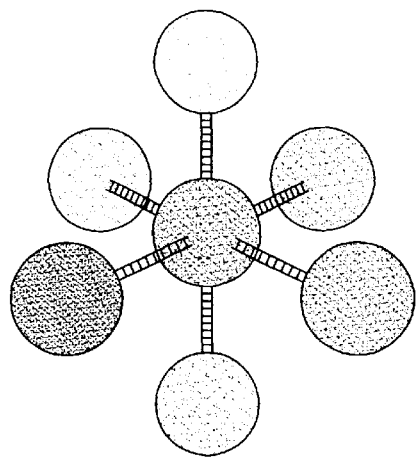
NANOSPHERES ARRANGED IN OCTAHEDRON
USING 3D DNA NANOCONSTRUCTION TECHNIQUES
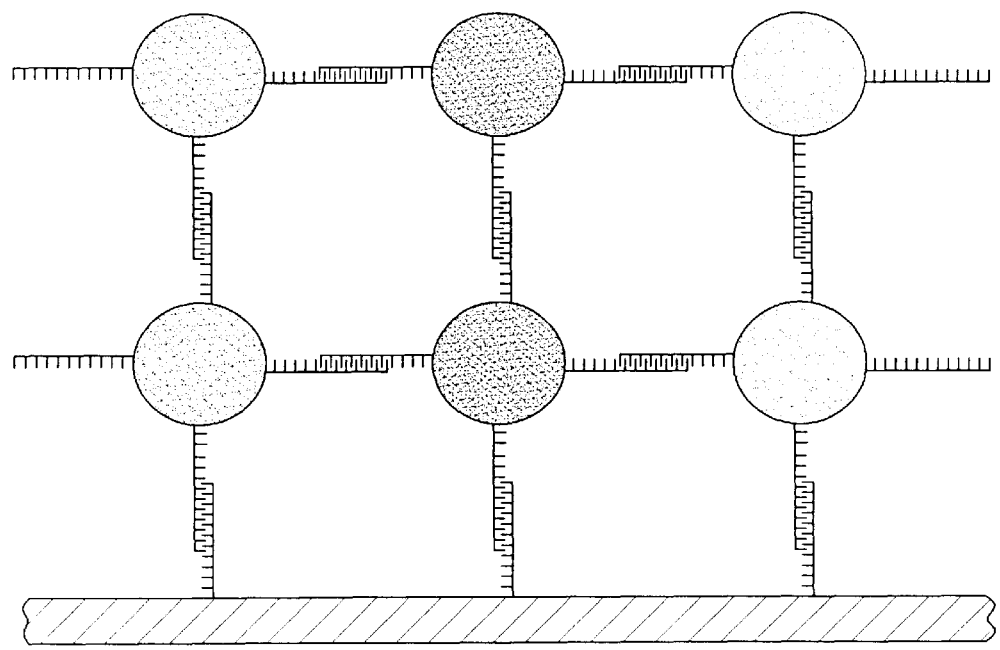
NANOSPHERES ARRANGED INTO LATTICE STRUCTURE AND BOUND TO SURFACE TO CREATE A 3D DEVICE
FIG. 36

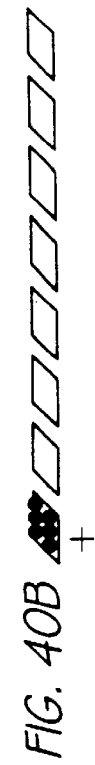

FIG. 40A NEGATIVELY CHARGED TYPE 1 NANOSTRUCTURES MOVE TOWARD POSITIVELY BIASED MICROLOCATION — TYPE 1 NANOSTRUCTURES

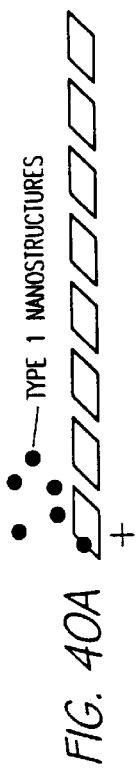

FIG. 40B TYPE 1 NANOSTRUCTURES ACCUMULATE ON THE POSITIVELY BIASED MICROLOCATION

FIG. 40C NEGATIVELY CHARGED TYPE 2 NANOSTRUCTURES ARE INTRODUCED OVER THE ARRAY AND ACCUMULATE ON THE POSITIVELY BIASED MICROLOCATIONS — TYPE 2 NANOSTRUCTURES

FIG. 40D BOTH TYPE 1 AND TYPE 2 NANOSTRUCTURES ARE NOW CLUSTERED ONTO THEIR RESPECTIVE MICROLOCATIONS

FIG. 40E ELECTRONICALLY ASSISTED SELF-ASSEMBLY BEGINS WHEN MICROLOCATION #1 IS BIASED NEGATIVE AND A CENTER MICROLOCATION IS BIASED POSITIVE CAUSING THE NEGATIVELY CHARGED TYPE 1 NANOSTRUCTURES TO MOVE TO CENTER LOCATION

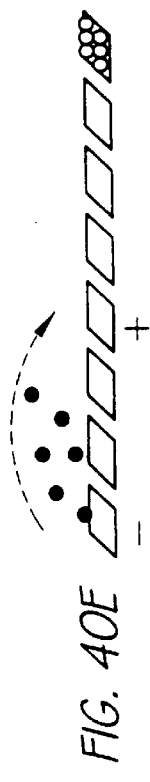

FIG. 40F TYPE 1 NANOSTRUCTURES ACCUMULATE AND HYBRIDIZE TO THE SPECIFIC MICROLOCATION

FIG. 40G TYPE 2 NANOSTRUCTURES ARE MOVED TO CENTER LOCATION BY BIASING MICROLOCATION #8 NEGATIVE AND CENTER LOCATION POSITIVE

FIG. 40H TYPE 2 NANOSTRUCTURES CONTAINING COMPLEMENTARY DNA SEQUENCE HYBRIDIZE TO TYPE 1 NANOSTRUCTURES

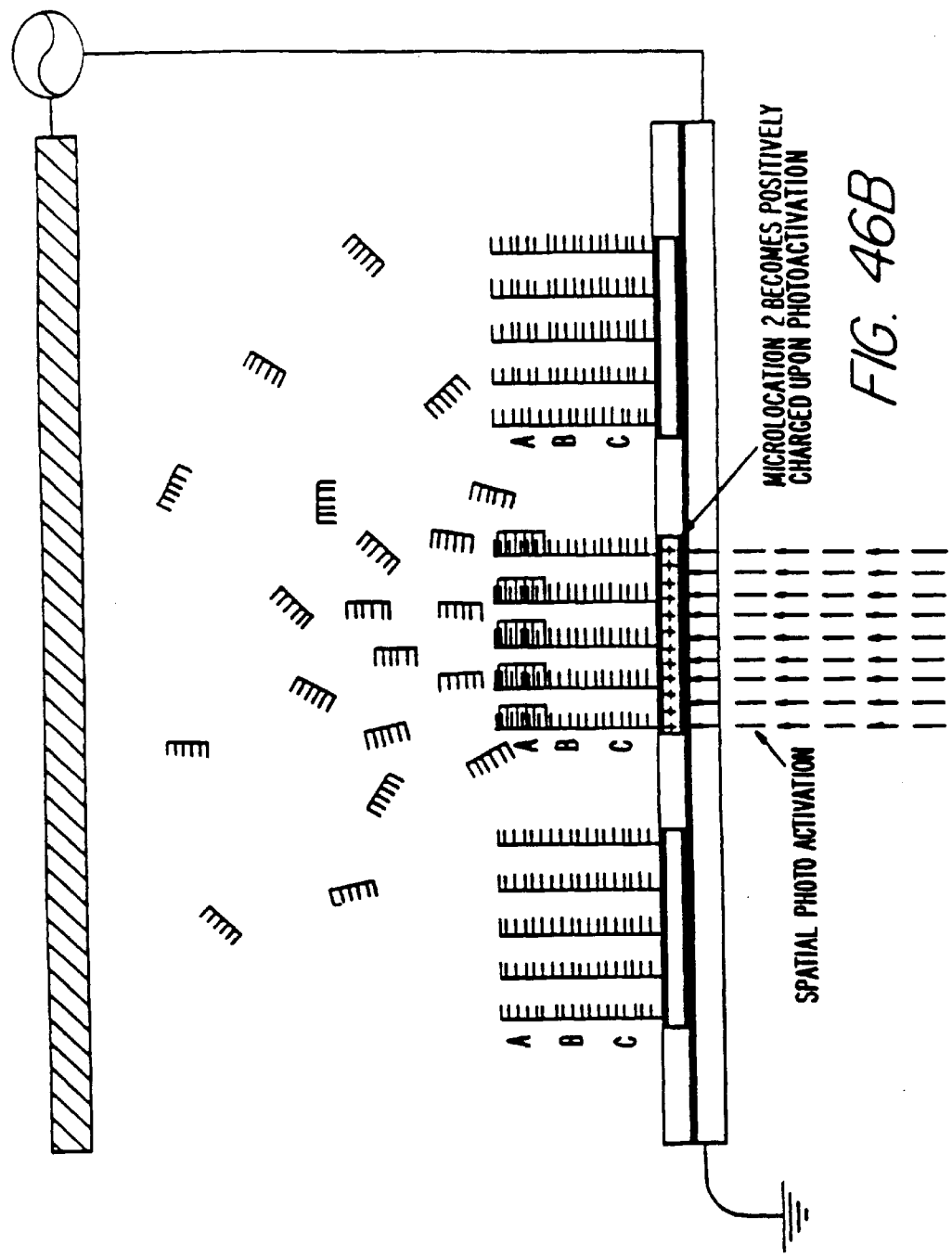

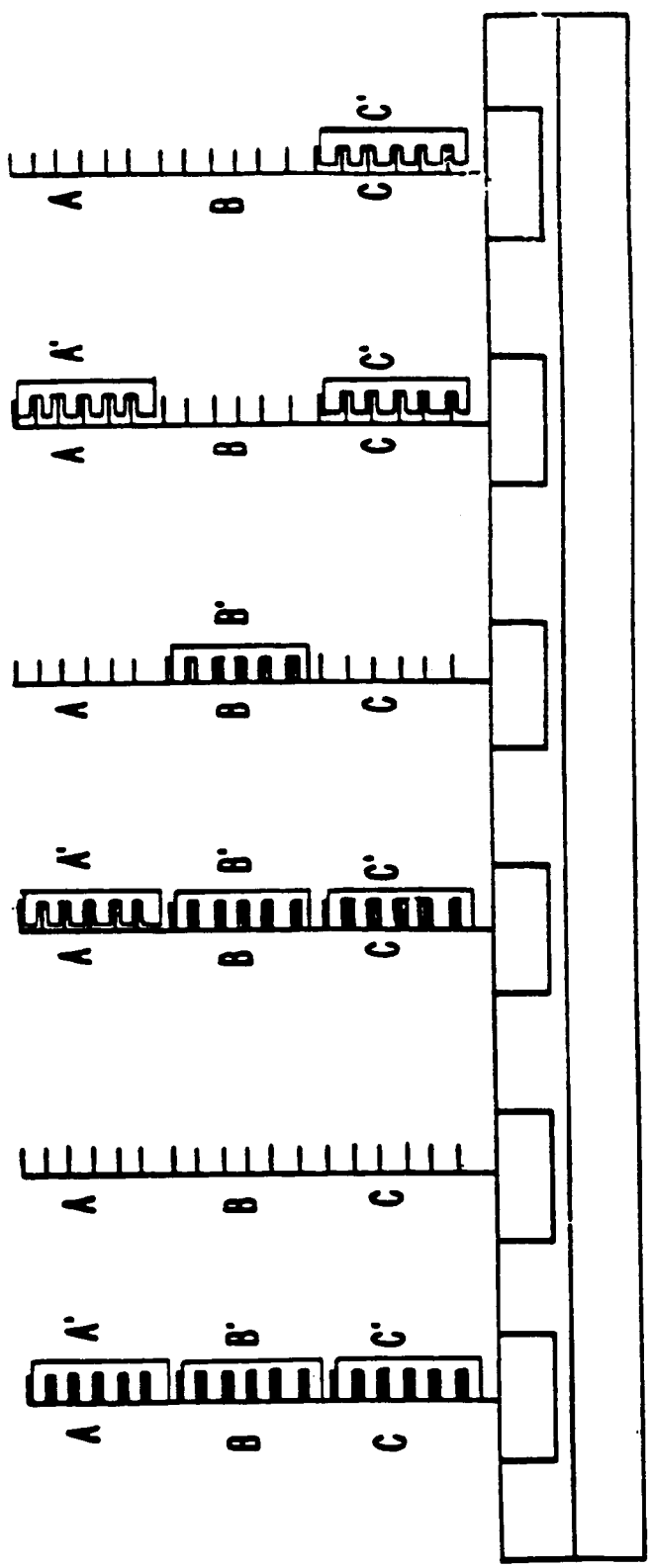

US 6,652,808 B1

METHODS FOR THE ELECTRONIC ASSEMBLY AND FABRICATION OF DEVICES

RELATED APPLICATION INFORMATION

This application is a continuation-in-part application of Application Ser. No. 08/534,454, filed Sep. 27, 1995, entitled "Apparatus and Methods for Active Programmable Matrix Devices", now U.S. Pat. No. 5,849,486; which is a continuation-in-part of application Ser. No. 08/304,657, filed Sep. 9, 1994, entitled, as amended, "Molecular Biological Diagnostic Systems Including Electrodes", now issued as U.S. Pat. No. 5,632,957, which is a continuation-in-part of application Ser. No. 08/271,882, filed Jul. 7, 1994, entitled, as amended, "Methods for Electronic Stringency Control for Molecular Biological Analysis and Diagnostics", now U.S. Pat. No. 6,017,691; which is a continuation-in-part of application Ser. No. 07/146,504, filed Nov. 1, 1993, entitled, as amended, "Active Programmable Electronic Devices for Molecular Biological Analysis and Diagnostics", now issued as U.S. Pat. No. 5,605,662 and application Ser. No. 08/703,601, filed Aug. 23, 1996, entitled "Hybridization of Polynucleotide Conjugated with Chromophores and Fluorophores to Generate Donor-to-Donor Energy Transfer System", now U.S. Pat. 5,849,489; which is a continuation of application Ser. No. 08/232,233, filed May 5, 1994, entitled "Hybridization of Polynucleotide Conjugated with Chromophores and Fluorophores to Generate Donor-to-Donor Energy Transfer System", now issued as U.S. Pat. No. 5,565,322, which is a continuation-in-part of application Ser. No. 07/790,262, filed Nov. 7, 1991, entitled "Self-Organizing Molecular Photonic Structures Based on Chromophore- and Fluorophore-Containing Polynucleotide and Methods of Their Use", now abandoned which is continued as U.S. Pat. No. 5,532,129 now application Ser. No. 08/250,951, filed May 27, 1994) and application Ser. No. 08/258,168, filed Jun. 10, 1994, entitled "DNA Optical Storage", now U.S. Pat. No. 5,787,032; all incorporated herein by reference as if fully set forth herein.

FEDERAL GOVERNMENT RIGHTS

The Federal Government may have rights in certain claims of this patent under Contract No. F 30602-94-C-0179 with the United States Air Force.

FIELD OF THE INVENTION

This invention relates to methodologies and techniques which utilize programmable functionalized self-assembling nucleic acids, nucleic acid modified structures, and other selective affinity or binding moieties as building blocks for: (1) creating molecular electronic and photonic mechanisms; (2) for the organization, assembly, and interconnection of nanostructures, submicron and micron sized components onto silicon or other materials; (3) for the organization, assembly, and interconnection of nanostructures, submicron and micron sized components within perimeters of microelectronic or optoelectronic components and devices; (4) for creating, arraying, and manufacturing photonic and electronic structures, devices, and systems; (5) for the development of a high bit density (large byte) three and four dimensional optical data storage materials and devices; and (6) for development of low density optical memory for applications in authentication, anti-counterfeiting, and encryption of information in document or goods. This invention also relates to associated microelectronic and optoelectronic devices, systems, and manufacturing platforms which provide electric field transport and selective addressing of self-assembling, nanostructures, sub-micron and micron sized components to selected locations on the device itself or onto other substrate materials.

BACKGROUND OF THE INVENTION

The fields of molecular electronics/photonics and nanotechnology offer immense technological promise for the future. Nanotechnology is defined as a projected technology based on a generalized ability to build objects to complex atomic specifications. Drexler, *Proc. Natl. Acad. Sci USA*, 78:5275–5278, (1981). Nanotechnology generally means an atom-by-atom or molecule-by-molecule control for organizing and building complex structures all the way to the macroscopic level. Nanotechnology is a bottom-up approach, in contrast to a top-down strategy like present lithographic techniques used in the semiconductor and integrated circuit industries. The success of nanotechnology may be based on the development of programmable self-assembling molecular units and molecular level machine tools, so-called assemblers, which will enable the construction of a wide range of molecular structures and devices. Drexler, "Engines of Creation," Doubleday Publishing Co., New York, N.Y. (1986). Present molecular electronic/photonic technology includes numerous efforts from diverse fields of scientists and engineers. Carter, ed., "Molecular Electronic Devices II," Marcel Dekker, Inc, New York, N.Y. (1987). Those fields include organic polymer based rectifiers, Metzger et al., "Molecular Electronic Devices II," Carter, ed., Marcel Dekker, New York, N.Y., pp. 5–25 (1987), conducting conjugated polymers, MacDiarmid et al., *Synthetic Metals*, 18:285 (1987), electronic properties of organic thin films or Langmuir-Blogett films, Watanabe et al., *Synthetic Metals*, 28:C473 (1989), molecular shift registers based on electron transfer, Hopfield et al., *Science*, 241:817 (1988), and a self-assembly system based on synthetically modified lipids which form a variety of different "tubular" microstructures. Singh et al., "Applied Bioactive Polymeric Materials," Plenum Press, New York, N.Y., pp. 239–249 (1988). Molecular optical or photonic devices based on conjugated organic polymers, Baker et al., *Synthetic Metals*, 28:D639 (1989), and nonlinear organic materials have also been described. Potember et al., *Proc. Annual Conf. IEEE in Medicine and Biology*, Part 4/6:1302–1303 (1989).

However, none of the cited references describe a sophisticated or programmable level of self-organization or self-assembly. Typically the actual molecular component which carries out the electronic and/or photonic mechanism is a natural biological protein or other molecule. Akaike et al., *Proc. Annual Conf. IEEE in Medicine and Biology*, Part 4/6:1337–1338 (1989). There are presently no examples of a totally synthetic programmable self-assembling molecule which produces an efficient electronic or photonic structure, mechanism or device.

Progress in understanding self-assembly in biological systems is relevant to nanotechnology. Drexler, *Proc. Natl. Acad. Sci USA*, 78:5275–5278 (1981), and Drexler, "Engines of Creation," Doubleday Publishing Co., New York, N.Y. (1986). Areas of significant progress include the organization of the light harvesting photosynthetic systems, the energy transducing electron transport systems, the visual process, nerve conduction and the structure and function of the protein components which make up these systems. The so called bio-chips described the use of synthetically or biologically modified proteins to construct molecular electronic devices. Haddon et al., *Proc. Natl. Acad. Sci. USA*, 82:1874–1878 (1985), McAlear et al., "Molecular Electronic Devices II," Carter ed., Marcel Dekker, Inc., New York N.Y., pp. 623–633 (1987).

Some work on synthetic proteins (polypeptides) has been carried out with the objective of developing conducting networks. McAlear et al., "Molecular Electronic Devices," Carter ed., Marcel Dekker, New York, N.Y., pp. 175–180 (1982). Other workers have speculated that nucleic acid based bio-chips may be more promising. Robinson et al., "The Design of a Biochip: a Self-Assembling Molecular-Scale Memory Device," *Protein Engineering*, 1:295–300 (1987).

Great strides have also been made in the understanding of the structure and function of the nucleic acids, deoxyribonucleic acid or DNA, Watson, et al., in "Molecular Biology of the Gene," Vol. 1, Benjamin Publishing Co., Menlo Park, Calif. (1987), which is the carrier of genetic information in all living organisms (See FIG. 1). In DNA, information is encoded in the linear sequence of nucleotides by their base units adenine, guanine, cytosine, and thymidine (A, G, C, and T). Single strands of DNA (or polynucleotide) have the unique property of recognizing and binding, by hybridization, to their complementary sequence to form a double stranded nucleic acid duplex structure. This is possible because of the inherent base-pairing properties of the nucleic acids: A recognizes T, and G recognizes C. This property leads to a very high degree of specificity since any given polynucleotide sequence will hybridize only to its exact complementary sequence.

In addition to the molecular biology of nucleic acids, great progress has also been made in the area of the chemical synthesis of nucleic acids. This technology has developed so automated instruments can now efficiently synthesize sequences over 100 nucleotides in length, at synthesis rates of 15 nucleotides per hour. Also, many techniques have been developed for the modification of nucleic acids with functional groups, including: fluorophores, chromophores, affinity labels, metal chelates, chemically reactive groups and enzymes. Smith et al., *Nature*, 321:674–679 (1986); Agarawal et al., *Nucleic Acids Research*, 14:6227–6245 (1986); Chu et al., *Nucleic Acids Research*, 16:3671–3691 (1988).

An impetus for developing both the synthesis and modification of nucleic acids has been the potential for their use in clinical diagnostic assays, an area also referred to as DNA probe diagnostics. Simple photonic mechanisms have been incorporated into modified oligonucleotides in an effort to impart sensitive fluorescent detection properties into the DNA probe diagnostic assay systems. This approach involved fluorophore and chemilluminescent-labeled oligonucleotides which carry out Förster nonradiative energy transfer. Heller et al., "Rapid Detection and Identification of Infectious Agents," Kingsbury et al., eds., Academic Press, New York, N.Y. pp. 345–356 (1985). Förster nonradiative energy transfer is a process by which a fluorescent donor group excited at one wavelength transfers its absorbed energy by a resonant dipole coupling process to a suitable fluorescent acceptor group. The efficiency of energy transfer between a suitable donor and acceptor group has a $1/r^6$ distance dependency (see Lakowicz et al., "Principles of Fluorescent Spectroscopy," Plenum Press, New York, N.Y., Chap. 10, pp. 305–337 (1983)).

As to photonic devices, they can generally be fabricated in dense arrays using well developed micro-fabrication techniques. However, they can only be integrated over small areas limited by the relatively high defect densities of the substrates employed. In order to be useful and economically viable, these devices must in many cases, be used within large area silicon integrated circuits. A good example of this issue is the vertical cavity surface emitting lasers. To address many potential applications, it would be highly desirable to integrate these devices with large area silicon IC's. A major obstacle in the integration of these new devices with silicon is the existence of material and geometrical incompatibilities. These devices need to be integrated on silicon in large sparse arrays with minimal performance degradation, and without affecting the underlying silicon circuits. Over the past years, a number of component assembly technologies have been extensively investigated regarding the integration of such compound semiconductor devices on silicon. These include hybrid flip-chip bonding or epitaxial lift-off and other direct bonding methods. Although these hybrid technologies have made significant progress and several component demonstrations have shown the viability of these techniques, these methods do not address the problem of geometrical incompatibility. That is, the dimensions with which the specialty devices are fabricated on their mother substrate must be conserved when they are coupled onto the host substrate. This makes the integration of small area devices on large area components economically unfeasible.

A major obstacle in the integration of these new devices with silicon is the existence of material and geometrical incompatibilities. These devices need to be integrated on silicon in large sparse arrays with minimal performance degradation, and without affecting the underlying silicon circuits. Over the past years, a number of component assembly technologies have been extensively investigated regarding the integration of such compound semiconductor devices on silicon. These include hybrid flip-chip bonding or epitaxial lift-off and other direct bonding methods. Although these hybrid technologies have made significant progress and several component demonstrations have shown the viability of these techniques, these methods do not address the problem of geometrical incompatibility. That is, the dimensions with which the specialty devices are fabricated on their mother substrate must be conserved when they are coupled or grafted onto the silicon board.

The prior art has no integration technique that is capable of creating a sparse array of devices distributed over a large area, when the devices are originally fabricated densely over small areas. This makes large area components made up from integration of micron size devices economically unfeasible. To solve this problem, the electronics industry employs a hierarchy of packaging techniques. However, this problem remains unsolved when a regular array of devices is needed on large areas with a relatively small pitch. This problem is probably most noticeable through the high cost associated with the implementation of matrix addressed displays, where the silicon active matrix consists of small transistors that need to be distributed over a large area. Thus, prior art microfabrication techniques limit devices to small area components where a dense array of devices are integrated. However, there are a number of important applications that could benefit from specialty devices being integrated more sparsely over large areas.

One possible method for removing the geometrical limitations is the further development of semiconductor substrate materials to the point where their defect densities approaches that of silicon. This is a long and expensive process that requires incremental progress. A second approach is the development of special robots capable of handling micron and sub-micron size devices and able to graft them to appropriate places. This also seems impractical because the grafting process will remain sequential where one device may be grafted after another, requiring impractical processing times. In any case, both of these approaches may be limited to motherboard dimensions on the order of 10 cm.

With regard to memories, data processing engines have been physically and conceptually separated from the memory which stores the data and program commands. As processor speed has increased over time, there has been a continuous press for larger memories and faster access. Recent advances in processor speed have caused system bottlenecks in access to memory. This restriction is critical because delays in obtaining instructions or data may cause significant processor wait time, resulting in loss of valuable processing time.

Various approaches have been taken to solve these concerns. Generally, the solutions include using various types of memory which have different attributes. For example, it is common to use a relatively small amount of fast, and typically expensive, memory directly associated with the processor units, typically called cache memory. Additionally, larger capacity, but generally slower, memory such as DRAM or SRAM is associated with the CPU. This intermediate memory is often large enough for a small number of current applications, but not large enough to hold all system programs and data. Mass storage memory, which is ordinary very large, but relatively inexpensive, is relatively slow. While advances have been continually made in improving the size and speed of all types of memory, and generally reducing the cost per bit of memory, there remains a substantial need especially to serve yet faster processors.

For the last 20 years most mass storage devices have utilized a rotating memory medium. Magnetic media have been used for both "floppy" (flexible) disks or "hard" disk drives. Information is stored by the presence or absence of magnetization at defined physical locations on the disk. Ordinarily, magnetic media are "read-write" memories in that the memory may be both written to and read from by the system. Data is written to or read from the disk by heads placed close to the surface of the disk.

A more recent development in rotating mass storage media are the optical media. Compact disks are read only memory in which the presence or absence of physical deformations in the disk indicates the data. The information is read by use of a focused laser beam, in which the change in reflectance properties from the disk indicate the data states. Also in the optical realm are various optical memories which utilize magnetooptic properties in the writing and reading of data. These disks are both read only, write once read many ("WORM") drives and multiple read-write memories. Generally, optical media have proved to have a larger storage capacity, but higher costs per bit and limited write ability, as compared with magnetic media.

Several proposals have been made for using polymers for electronic based molecular memories. For example, Hopfield, J. J., Onuchic, J. N. and Beratan, D. N., "A Molecular Shift Register", *Science*, 241, p. 817, 1988, discloses a polymer based shift register memory which incorporates charge transfer groups. Other workers have proposed an electronic based DNA memory (see Robinson et al, "The Design of a Biochip: A Self-Assembling Molecular-Scale Memory Device", *Protein Engineering*, 1:295–300 (1987). In this case, DNA is used with electron conducting polymers for a molecular memory device. Both concepts for these molecular electronic memories do not provide a viable mechanism for inputting data (write) and for outputting data (read).

Molecular electronic memories have been particularly disappointing in their practical results. While proposals have been made, and minimal existence proofs performed, generally these systems have not been converted to commercial reality. Further, a specific deficiency of the system described above is that a sequential memory is typically substantially slower than a random access memory for use in most systems.

The optical memories described above suffer from the particular problem of requiring use of optical systems which are diffraction limited. This imposes size restrictions upon the minimum size of a data bit, thereby limiting memory density. This is an inherent limit in systems which store a single bit of data at a given physical memory location.

Further, in all optical memory systems described above, the information is stored on a bit-by-bit basis, such that only a single bit of data is obtained by accessing a giving physical location in memory. While word-wide memory access systems do exist, generally they store but a single bit of information at a given location, thereby requiring substantially the same amount of physical memory space whether accessed in a bit manner or word-wide manner.

While systems have generally increased in speed and storage density, and decreased in cost per bit, there remains a clear gap at present between processor speed and system requirements. See generally, "New Memory Architectures to Boost Performance", Tom R. Halfhill, Byte, July, 1993, pp 86 and 87. Despite the general desirability of memories which are faster, denser and cheaper per bit, and the specific critical need for mass memory which can meet the demands of modern day processor systems speed, no completely satisfactory solution has been advanced heretofore. The fundamental limitations on the currently existing paradigms cannot be overcome by evolutionary enhancements in those systems.

Despite the clear desirability for new and improved apparatus and methods in this field, no optimal solution has been proposed previously.

SUMMARY OF THE INVENTION

Increasingly, the technologies of communication, information processing, and data storage are beginning to depend upon highly-integrated arrays of small, fast electronic and photonic devices. As device sizes scale down and array sizes increase, conventional integration techniques become increasingly costly. The dimensions of photonic and electronic devices permit the use of molecular biological engineering for the integration and manufacturing of photonic and electronic array components. This invention relates to methodologies and manufacturing techniques which utilize programmable functionalized self-assembling nucleic acids, nucleic acid modified structures, and other selective affinity or binding moieties as building blocks for: (1) creating molecular electronic and photonic mechanisms; (2) for the organization, assembly, and interconnection of nanostructures, submicron and micron sized components onto silicon or other materials; (3) for the organization, assembly, and interconnection of nanostructures, submicron and micron sized components within perimeters of microelectronic or optoelectronic components and devices; (4) for creating, arraying, and manufacturing photonic and electronic structures, devices, and systems; (5) for the development of a high bit density (large byte) three and four dimensional optical data storage materials and devices; and (6) for development of low density optical memory for applications in authentication, anti-counterfeiting, and encryption of information in documents or goods. This invention also relates to associated microelectronic and optoelectronic devices, systems, and manufacturing platforms which provide electric field transport and selective addressing of self-assembling, nanostructures, sub-micron and micron size components to selected locations on the device itself or onto other substrate materials.

Functionalized nucleic acids based polymers (e.g., DNA, RNA, peptide nucleic acids, methyphosphonates) constitute a vehicle to assemble large numbers of photonic and electronic devices and systems, utilizing the base-pair coding property of the DNA which allows specific complementary double stranded DNA structures to be formed. This unique property of DNA provides a programmable recognition code (via the DNA sequence) which can be used for specific placement and alignment of nanostructures.

In the preferred embodiment, the process by which photonic devices would be aligned, involves first coating them with a specific DNA sequence. The area of the host substrate where attachment of the devices is desired are coated with the specific complementary DNA sequence. The substrate and DNA-covered devices are released into a solution and hybridization between complementary DNA strands occurs. Hybridization effectively grafts the devices to their proper receptor locations on the substrate.

More broadly, the invention in this respect relates to a method for the fabrication of micro scale and nanoscale devices comprising the steps of: fabricating first component devices on a first support, releasing at least one first component device from the first support, transporting the first component device to a second support, and attaching the first component device to the second support.

Some potential applications for these techniques are: (1) fabricating light emitter arrays over large surfaces; (2) assembly of two or three-dimensional photonic crystal structures; and (3) manufacturing of various hybrid-integrated components including flat panel displays, medical diagnostic equipment and data storage systems.

As photonics plays an increasingly important role in information processing, communication and storage systems it will deliver faster, smaller, more power efficient, and functionally versatile integrated systems at lower cost. New fabrication technologies including nanostructure fabrication, integration and self-assembly techniques are used. As device dimensions shrink to submicron levels, it becomes important to utilize the inventive concepts employing molecular biological engineering concepts and principles as manufacturing techniques for the fabrication of integrated photonic and electronic devices.

These inventions relate to nanostructures, submicron and micron-sized structures incorporating synthetic DNA polymers. This includes DNA modified with small chromophore molecules, to large structures (e.g., micron-sized) which are modified with DNA sequences. Synthetic DNA polymers can be designed with highly specific binding affinities. When covalently attached to nanoscale organic and metallic structures or micron scale semiconductor component devices, DNA polymers can provide a self-assembly fabrication mechanism. This mechanism can be used for both the selective grafting of the devices to specific pre-programmed locations on a desired surface, and for the clustering of devices into pre-programmed 2-D or 3-D lattices. For grafting of photonic or electronic component devices onto host substrates, DNA polymers with complementary sequences are first synthesized. The photonic component devices and desired areas of the host substrate (receptor areas) are coated with the complementary DNA sequences. The host substrates are then introduced into a solution.

In one aspect of this invention, a method for fabrication of nanoscale and microscale structures is provided comprising the steps of: providing a structure with multiple affinity surface identities, orienting the structure in an electric field, and reacting the oriented structure with an affinity site.

In yet another aspect of this invention, a method for forming a multiple identity substrate material is provided comprising the steps of: providing a first affinity sequence at multiple locations on a support, providing a functionalized second affinity sequence, which reacts with the first affinity sequence, and has an unhybridized overhang sequence, and selectively cross-linking first affinity sequences and second affinity sequences.

In yet another aspect of this invention, a method for the assembly of chromophoric structures is provided comprising the steps of: selectively irradiating a photoactivatable region, whereby an electric field is generated corresponding to the region, providing charged reactants in solution which includes the electric field, and repeating the selective irradiation to sequentially assemble the chromophoric structures.

It is an object of this invention to enable nanotechnology and self-assembly technology by the development of programmable self-assembling molecular construction units.

BRIEF DESCRIPTION OF THE DRAWINGS

FIG. 3A is a perspective drawing of the apparatus and method for redistribution of photonic devices fabricated as dense arrays onto the host substrate without mother substrate layout constraints.

FIG. 3B is a perspective view of a clustering of nanospheres by DNA assisted self-assembly to form synthetic photonic crystals.

FIG. 4 shows a cross-section of an attachment mechanism for attaching DNA to silicon.

FIG. 11 is a cross-sectional view of a step in the process for preparing DNA write materials wherein location number 1 is masked from ultraviolet exposure while unmasked locations are exposed permitting cross-linking between sequences A and B.

FIG. 12 is a cross-sectional view of a step in the process for preparing DNA write materials wherein dehybridization is carried out to remove the non-crosslinked sequence B from the previously masked location.

FIG. 19 is a cross-sectional view of a step in the process for preparing DNA write materials wherein complementary DNA sequences to A, B, C and D identities labeled with four respective fluorescent dyes are hybridized to demonstrate each identity.

FIG. 20 is a cross-sectional view of a step in the process for preparing DNA write materials showing the chip surface with A, B, C and D identities.

FIG. 21 is a cross-sectional view of a step in the process for preparing DNA write materials showing selective UV exposure which leaves locations 1 and 3 unhybridizable and locations 2 and 4 hybridizable.

FIG. 22 is a cross-sectional view of a step in the process for preparing DNA write materials showing the DNA complements labeled with their respective fluorophores applied to the surface, wherein only locations B and D hybridized their respective fluorescent complements.

FIGS. 28A, 28B and 28C show cross-sectional views of apparatus and method steps for providing multicolor images, wherein FIG. 28A shows a portion of the surface being labeled with BODIPY Texas Red, FIG. 28B shows a portion of the surface being labeled with BODIPY Orange and FIG. 28C showing a portion of the surface being labeled with BODIPY Texas Red and the other portion labeled with BODIPY Orange.

FIG. 36 shows structures for the formation of nanodevices, providing an octahedron using 3-D DNA nanoconstruction techniques (top) and nanospheres arranged into lattice structure and bound to surface to create a 3-D device (lower).

FIGS. 40A–40H show the larger environment of FIG. 39, wherein FIG. 40A shows negatively charged type 1 nanostructures moving towards a positively biased microlocation, FIG. 40B shows accumulated nanostructures on the positively biased microlocation, FIG. 40C shows negatively charged type 2 nanostructures introduced over the array and accumulated on the positively biased microlocations, FIG. 40B shows both type 1 and type 2 nanostructures clustered on their respective locations, FIG. 40E shows electronically assisted self-assembly beginning when microlocation number 1 is biased negative and a center microlocation is biased positive causing the negatively charged type 1 nanostructures to move to the center location, FIG. 40F shows type 1 nanostructures accumulated and hybridized to the specific microlocation, FIG. 40G shows type 2 nanostructures moved to the center location by biasing microlocation number 8 negative and center location positive, and FIG. 40H shows type 2 nanostructures containing complementary DNA sequence hybridized to type 1 nanostructures.

FIGS. 46A–46F show steps in a spatial light addressing process.

IMPORTANT ASPECTS OF DNA STRUCTURE, PROPERTIES, AND SYNTHESIS

Figure 1B:
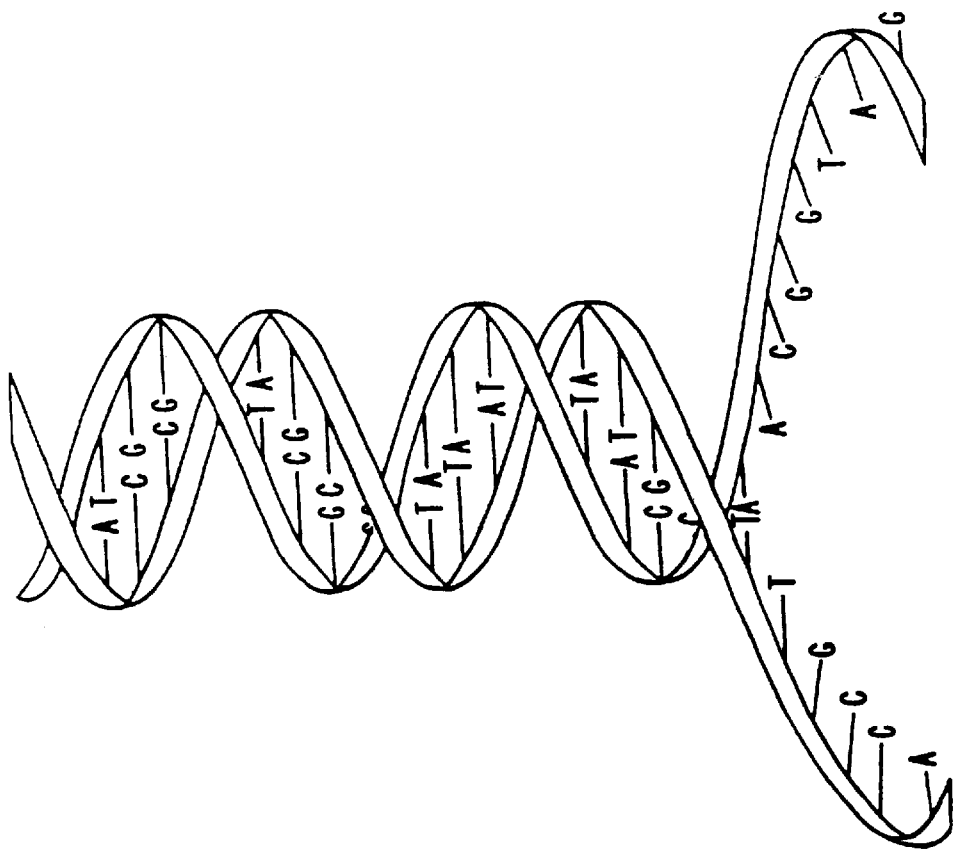
FIGS. 1A and 1B show DNA structure and its related physical dimensions.
Figure 1A:
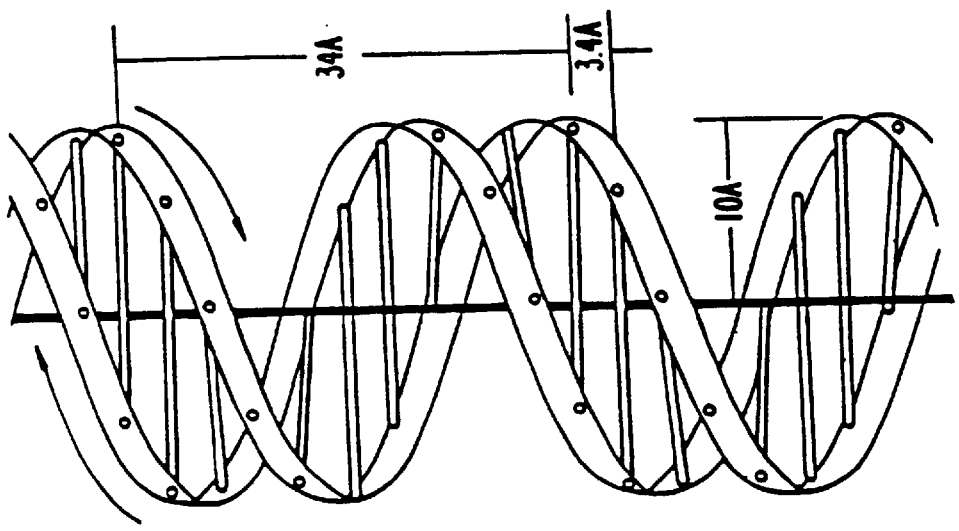

Synthetic DNA possesses a number of important properties which make it a useful material for the applications of these inventions. The most important are the molecular recognition (via base pairing) and self-assembly (via hybridization) properties which are inherent in all DNA molecules. Other important advantages include the ability to easily synthesize DNA, and to readily modify its structure with a variety of functional groups. We have extensively investigated the photonic and electronic energy transfer mechanisms in self-assembled arrangements of synthetic DNA functionalized with a wide variety of donor and acceptor chromophore groups. We have paid particular attention to the basic problems involved in communicating or getting information in and out of these molecular structures. This basic work is now being applied to potential applications for high density optical storage materials, which have been designed to absorb light energy at a single wavelength and re-emit at predetermined multiple wavelengths. We are also now using DNA polymers for the two and three dimensional organization of micron and submicron sized structures on silicon surfaces. This work is being directed at the development of novel optoelectronic devices.

The DNA molecule is considered important to this invention and the proposed applications because it is inherently programmable and can self-assemble. Designing, synthesizing, and organizing these systems requires nanometer range control which few other synthetic polymer systems can match. Additionally, DNA molecules are relatively stable and have a number of other attributes which make them a preferred material for nanofabrication.

The underlying technology for DNA and other nucleic acid type polymers comes from the enormous effort that has been invested over the past fifteen years in synthetic nucleic acid chemistry. Molecular biologists have refined techniques and DNA materials in their pursuit of diagnostics, genetic sequencing, and drug discovery. The basic chemistry for the efficient synthesis of DNA, its modification, its labeling with ligands and chromophores, and its covalent linkage to solid supports are now well developed technologies. Synthetic DNA represents the preferred material into which so many important structural, functional, and mechanistic properties can be combined.

DNA polymers have three important advantages over any of the present polymeric materials used for electronic and photonic applications. First, DNA polymers provide a way to encode highly specific binding-site identities o semiconductor or photonic surfaces. These sites, produced at defined locations, could be of microscopic (micron), sub-micron, or even molecular (nanometer) dimension. Second, DNA polymers provide a way to specifically connect any of these locations. The pre-programmed DNA polymers self-organize automatically. Finally, DNA polymers provide the building blocks for nanotechnology; they are self-organizing materials for creating true molecular-level electronic and photonic devices.

The specificity of DNA is inherent in the hydrogen bonding properties of the base components (Adenine bonds only with Thymine, and Guanine bonds only with Cytosine). These specific base pairing properties of DNA allow complementary sequences of DNA to "hybridize" together to form the double-stranded structure. It is this inherent property which allows DNA polymers to be used to form programmable self-assembling structures. Thus, when a photonic device has one specific DNA polymer sequence attached to it, it will only bind (hybridize) to a device or surface coated with the complementary DNA polymer sequence. Since a large variety of DNA sequences can be used, multiple devices, each attached to a different DNA sequence can in principle be self-assembled simultaneously. The following lists the important advantages of using DNA polymers for self-assembling nanofabrication applications:

1. DNA polymers can by synthesized both rapidly and efficiently with automated instruments. Conventional polymer chemistries can be significantly more complex and costly to develop.

2. DNA polymers can be synthesized in lengths from 2 to 150 nucleotides, which is the appropriate size range (1 nm to 60 nm) for self-assembling unit cells.

3. DNA polymers can be synthesized with any desired base sequence, therein providing programmable recognition for an almost unlimited number of specific connections.

4. DNA polymers with unique sequences of as few as ten nucleotides are highly specific and will bind only to their complementary sequence. Thus, the material allows specific connections as small as 3.4 nm to be made between molecular units.

5. DNA polymers can be covalently labeled with fluorophores, chromophores, affinity labels, metal chelates, chemically reactive functional groups and enzymes. This allows important photonic and electronic properties to be directly incorporated into the DNA polymers.

6. DNA polymers can be modified at any position in their sequence, and at several places within the individual nucleotide unit. This provides a means to position functional groups for maximum performance.

7. DNA polymers can be both covalently and non-covalently linked to solid surfaces: glass, metals, silicon, organic polymers, and bio-polymers. These attachment chemistries are both existing and easily developed.

8. The backbone structure of the DNA molecule itself can be highly modified to produce different properties. Thus, there is compatibility with existing semiconductor and photonic substrate materials.

9. Modified DNA polymers can be used to form three-dimensional structures, thus leading to ultra high density secondary storage schemes.

10. DNA polymers can be reversibly assembled and disassembled by cooling and heating, or modified to remain in the assembled state. This is a critical property for self-organizing materials as it allows for more options in the manufacture of resulting systems.

11. The structural and organizational properties of DNA polymers (nucleic acids in general) are well understood and can be easily modeled by simple computer programs. Thus, more complex molecular photonic and electronic devices can be designed.

DETAILED DESCRIPTION OF THE INVENTION

This invention relates to methodologies, techniques, and devices which utilize self-assembling DNA polymers, modified DNA polymers, DNA derivitized structures and other affinity binding moieties for nanofabrication and microfabrication of electronic and photonic mechanisms, devices and systems. This invention also relates to processes which allow mutiplex and multi-step fabrication, organization or assembly of modified DNA polymers, DNA derivitized structures, and other types of affinity or charged structures into more complex structures on or within silicon or other surfaces.

For purposes of this invention "DNA polymers" is broadly defined as polymeric or oligomeric forms (linear or three-dimensional) of nucleic acids including: deoxyribonucleic acid, ribonucleic acids (synthetic or natural); peptide nucleic acids (PNA); methyphosphonates; and other forms of DNA in which the backbone structure has been modified to produce negative, positive or neutral species, or linkages other than the natural phosphate ester. Also included are forms of DNA in which the sugar or base moieties have been modified or substituted, and polymeric forms of DNA in which nucleotide or polynucleotide units are interspersed with other units including but not limited to phosphate ester spacer moieties, amino acids, peptides, polysaccharides, synthetic organic polymers, silicon or inorganic polymers, conductive polymers, chromophoric polymers and nanoparticles or nanostructures.

For purposes of this invention "Modified or Derivitized DNA polymers" are broadly defined as nucleic acids which have been functionalized with chemical or biological moieties (e.g., amines, thiols, aldehydes, carboxyl groups, active esters, biotin and haptens) which allow the DNA to be attached covalently or non-covalently to other molecules, structures, or materials. Also included are forms of DNA which have been modified or Derivitized with chromophores, fluorophores, chelates, metal ions, amino acids, peptides, proteins, enzymes, antibodies, or aliphatic or aromatic moieties which change solubility, and moieties which change the net charge on the DNA molecule.

For purposes of this invention "DNA Derivitized structures" are broadly defined as nanostructures (organic, inorganic, biological); nanoparticles (gold, silica, and other inorganic materials); organic or polymeric nanobeads; submicron devices, components, particles, (silicon based devices produced by photolithography or E-beam lithography); and micron scale devices or particles which have been functionalized with a specific DNA sequence which allows the structure to be specifically attached or interconnected to another structure, device, or to a specific location on a surface.

While the terms "nanostructure" refers to sub-micron sized structures, terms such as "nano" or "micro" are not intended to be limited in the sense that a micron scale device can be functionalized with DNA polymers which technically have lengths of 10–180 nanometers.

The unique properties of DNA provides a programmable recognition code (via the DNA base sequence) which can be used for specific placement and alignment of sub-micron and nanoscale structures. The basic chemistry and technology required to attach specific DNA sequences to organic, semiconductor, and metallic compounds is known to the art and specific chemistries are described for carrying out such applications.

In the preferred embodiment, the process by which photonic devices are aligned and fixed to substrate surfaces, involves first coating them with a specific DNA polymer sequences. The area of the host substrate where attachment of the specific device is desired, would then be coated with the specific complementary DNA sequence. The substrate would be exposed to a solution containing the DNA covered devices, and hybridization between complementary DNA strands allowed to occur. This hybridization process effectively grafts the devices to their proper receptor locations on the substrate surface. This self-assembly fabrication process can be used for, by way of example, (1) the fabrication of light emitter arrays over large surface areas, and (2) the fabrication of two or three-dimensional photonic band-gap crystal structures.

This fabrication technique has major applications in the field of optoelectronics and in the manufacturing of various hybrid-integrated components including flat panel displays, medical diagnostic equipment and data storage systems. Novel devices with very small physical dimensions take advantage of various quantum confinement techniques. In most cases, these devices are preferably distributed over large areas (e.g. smart pixels and displays). Other devices may be brought together in dense regular crystal lattices (e.g. photonic bandgap crystals). In both cases, the physics of the devices are now understood, and viable fabrication techniques of these inventions are required. With regard to new processing techniques, DNA self-assembly technology allows these devices to be constructed.

Integrated photonic and electronic systems utilize the inventive fabrication technologies including nanostructure fabrication, integration, interconnection and self-assembly techniques. For such applications, DNA self-assembly fabrication technology involves the following steps. Synthetic DNA polymers are designed with highly specific binding affinities. When covalently attached to nanoscale organic, metallic or semiconductor component devices, DNA polymers provide a self-assembly fabrication mechanism. This mechanism can be used for both the selective grafting of devices to specific pre-programmed locations on a desired surface, and for the clustering of devices into pre-programmed 2 and 3 dimensional lattices.

Figure 2:
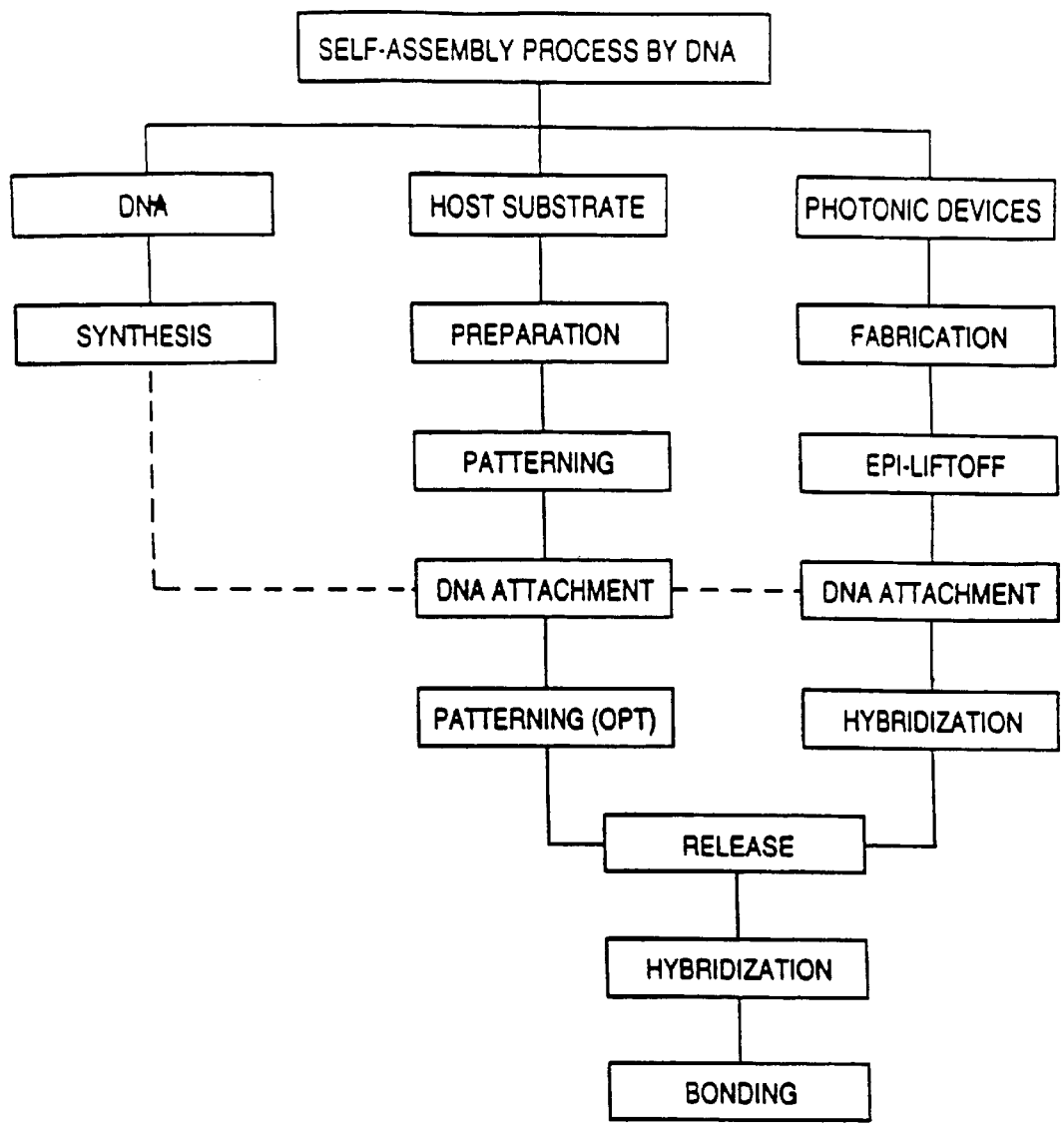
FIG. 2 is a flow diagram of self-assembly processes.

For grafting an array of photonic component devices onto a host substrates, DNA polymers with complementary sequences are first synthesized as shown in FIG. 2. The photonic component devices and desired areas of the host substrate (receptor areas) are coated with the complementary DNA sequences. The host substrate is then introduced into a hybridization solution. The devices coated with the specific DNA polymers are also released from their mother substrate into the solution. The released devices can be actively transported to their receptor areas under the influence of electrically or optically induced local fields (electrophoresis). Hybridization is carried out by carefully controlling the solution temperature, ionic strength, or the electric field strength. Once the devices are grafted via hybridization to their specific receptor areas, the solution is removed and the substrate is dried. Metallurgical (or eutectic) bonding can now be carried out at a higher temperature to fully bond the devices to the host substrate material. The clustering of sub-micron and nanoscale elements into 2-D or 3-D structures (e.g., photonic band-gap crystals), can be carried out in a similar fashion. In this case, the host substrate is replaced by other nanoscale elements. A major difference however, is the attachment technique used to position different DNA strands on the nanoscale elements.

The self-assembly fabrication technique based on DNA polymers offers two unique features. First, by removing the requirement for conservation of relative device spacing (as defined by the mother substrate) during the device grafting (hybridization) process, the technique enables the micron, sub-micron or nanoscale devices to be fabricated densely on their mother substrates and then be redistributed in a preprogrammed fashion onto the host substrate (FIG. 3.a).

This feature has a profound impact on the viability of intra-chip optical interconnects within large chips. It lowers the cost of silicon based smart pixels where photonic devices must be fabricated on more expensive smaller substrates. The second feature is the ability to manipulate and orient with respect to each other a large number of nanoscale devices (e.g. organic or metallic nanospheres). This feature allows the "growth" of synthetic photonic crystals with large lattice constants possessing desired orientation symmetries for exhibiting photonic bandgap properties (FIG. 3.b).

Thus, the highly specific binding affinities and self-assembly of DNA polymers can lead to:

(1) Low cost smart pixels and display devices by enabling photonic or electronic micron or nanoscale devices to be self-assembled and integrated over very large areas of silicon or other substrates, i.e. the self-assembly of an arrays of light emitters on a silicon substrate, (2) Highly selective wavelength and tunable devices by enabling dielectric nanostructures to be self-assembled to form photonic bandgap crystals, i.e. the encapsulation of emitter devices within a photonic bandgap crystal layer created by the self-assembly of DNA nanospheres, (3) Ultra high density optical storage media by enabling chromophore molecules and nanostructure units to be selectively self-positioned, and (4) The selective positioning of bonding structures, such as gold, tin or solder structures as bonding pads, e.g., to achieve low cost or unassisted die-to-die processing, e.g., for flip-chip applications.

In the preferred embodiment, these applications require four steps in the process. The first involves the design and synthesis of the DNA polymer sequences and their selective attachment to the sub-micron and nanoscale devices of interest. Second, attachment of specific complementary DNA polymers to pre-selected receptor locations on a host substrate surface. Third, the self-assembly of the devices by the DNA hybridization process. The fourth process involves establishing the electrical contacts.

This invention brings together molecular biological (DNA structure and function) and photonic and electronic device principles in a synergistic manner. On the photonic device side, novel devices with very small physical dimensions take advantage of various quantum confinement techniques. In most cases, these devices must be distributed over large areas (e.g. smart pixels and displays). In other cases, these devices must be brought together densely to form regular crystal lattices (e.g. photonic bandgap crystals). With regard to processing techniques, self-assembly DNA techniques with its well developed base of DNA synthesis, modification, and hybridization is an enabling technology for these applications. DNA linkage to solid supports and various other materials is possible via a variety of processes for attaching DNA selectively to silicon, gold, aluminum and other inorganic and organic materials. A number of thin film processing techniques are highly complementary with these DNA processes. For example, as will be described later, the lift-off process can be easily adapted to produce micron, and sub-micron devices with attached DNA sequences.

KEY PROCESSES FOR DNA BASED COMPONENT DEVICE SELF-ASSEMBLY

Four techniques are important for the DNA based component device self-assembly process. These are the DNA polymer synthesis, DNA attachment chemistry, DNA selective hybridization and epitaxial lift-off of semiconductor thin films and devices. In the following sections we provide brief summaries of these techniques.

DNA Synthesis and Derivitization

The synthesis of the DNA polymer or oligomer sequences, their purification, and their Derivitization with the appropriate attachment and chromophore groups can be carried out in the following preferred manner: DNA sequences are synthesized using automated DNA synthesizer and phosphoramidite chemistry procedures and reagents, using well known procedures. DNA polymers (polynucleotide, oligonucleotides, oligomers) can have primary amine groups incorporated at chemical bonding sites for subsequent attachment or functionalization reactions. These primary amine groups can be incorporated at precise locations on the DNA structure, according to the need for that particular sequence. Attachment sequences can also contain a terminal ribonucleotide group for subsequent surface coupling reactions. Sequences, including the amino modified oligomers, can be purified by preparative gel electrophoresis (PAGE) or high pressure liquid chromatography (HPLC). Attachment sequences with terminal amino groups can be designed for covalent bonding to gold, silver, or aluminum metalized features or to small areas where silicon dioxide is present. These sequences can be further Derivitized with a thiolation reagent called succinimidyl 3-(2-pyridyldithio)propionate (SPDP). This particular reagent produces a sequence with a terminal sulfhydryl group which can be used for subsequent attachment to metal surfaces. Other attachment sequences containing a terminal ribonucleotide group can be converted to a dialdehyde derivative via Schiff's base reaction. These attachment sequences can then be coupled to aminopropylated silicon dioxide surfaces. Specific sequences designed for electronic or photonic transfer responses can be functionalized with their appropriate chromophore, fluorophore, or charge transfer groups. Many of these groups are available off-the-shelf as activated reagents that readily couple with the chemical bonding sites described above to form stable derivatives.

DNA Attachment to Solid Supports and Preparation of the Host Substrate Materials This step involves the covalent coupling of the attachment sequences to solid support materials. In the general area of DNA attachment to solid materials, sequences have been covalently attached to a number of materials which include: (i) Glass ($SiO_2$), (ii) Silicon (Si), (iii) Metals (Gold, Silver, Aluminum), and (iv) Langmuir-Blodgett (LB) films. Glass, silicon, and aluminum structures have been prepared in the following manner. Glass and silicon ($SiO_2$) are first treated with dilute sodium hydroxide solution and aluminum with dilute hydrogen fluoride solution. The materials are then Derivitized for covalent coupling with the attachment sequences by treatment with 3-aminopropyltriethoxysilane (APS). This is carried out by refluxing the materials for 2–5 minutes in a 10% APS/toluene solution. After treatment with APS, the materials are washed once with toluene, then methanol, and finally dried for 1 hour at 100° C. Attachment to the APS Derivitized materials is carried out by reaction with the specific dialdehyde Derivitized attachment oligomers (see FIG. 4) for 1–2 hours in 0.1 M sodium phosphate buffer (pH 7.5). In addition, attachment to metal (gold, silver, aluminum) and organic features can be carried out.

To delineate the areas where the grafting of the specialty devices will take place, a selective attachment procedure for the complementary DNA polymer may be carried out. The selective attachment can be realized by using the inherent selectivity of DNA sequences, selective attachment chemistries, or by directed electrophoretic transport. Alternatively after attachment, the DNA strands in unwanted regions can be destroyed by UV radiation. This approach is useful only when one group of devices need to be self-assembled. This approach would in normal operation preclude subsequent DNA attachment processes, and would not allow for the self-assembly of several specialty device groups. Attachment chemistry is strongly dependent upon the materials used to which the DNA polymers may be attached.

For example, to attach DNA to aluminum pads on a silicon chip coated with a protective glass layer, the aluminum regions are activated by dipping the sample for a short period of time into a dilute buffered HF solution. The end result of this process is that only a few DNA strands are attached to the protective glass layer while the exposed aluminum pads are highly reactive to DNA. This material selectivity is a convenient and general way to attach DNA to the desired regions. When material selectivity is combined with UV directed inactivation and electrophoretic transport, this allows for repeatable attachment processes to be carried out sequentially.

Consider the simultaneous self-assembly of several types of specialty devices. The receptor pads need to be grouped according to the device to which they are to be coupled. In this case, each pad group needs to be coated with a specific DNA sequence complementary to the DNA sequence attached to the specialty device that it would be bonded to. In order to "pre-program" the receptor pads, each DNA sequence is attached sequentially to the proper pads. This can be easily achieved by using the electrophoretic transport process and by applying a negative potential to the pads where DNA attachment is not desired. Simultaneously, a positive voltage can be applied to enhance attachment to the desired locations. Alternatively, an optically induced electric field can be used to migrate the DNA strands to desired locations. For a second set of DNA sequence attachment, the procedure is repeated. It should be pointed out that when only one type of device needs to be self-assembled on the host substrate, the use of the material selectivity of the DNA attachment chemistry alone is sufficient. UV radiation of the regions where DNA hybridization is not desired, would be carried out.

Component Device Preparation and Epitaxial Lift-Off

Figure 5:
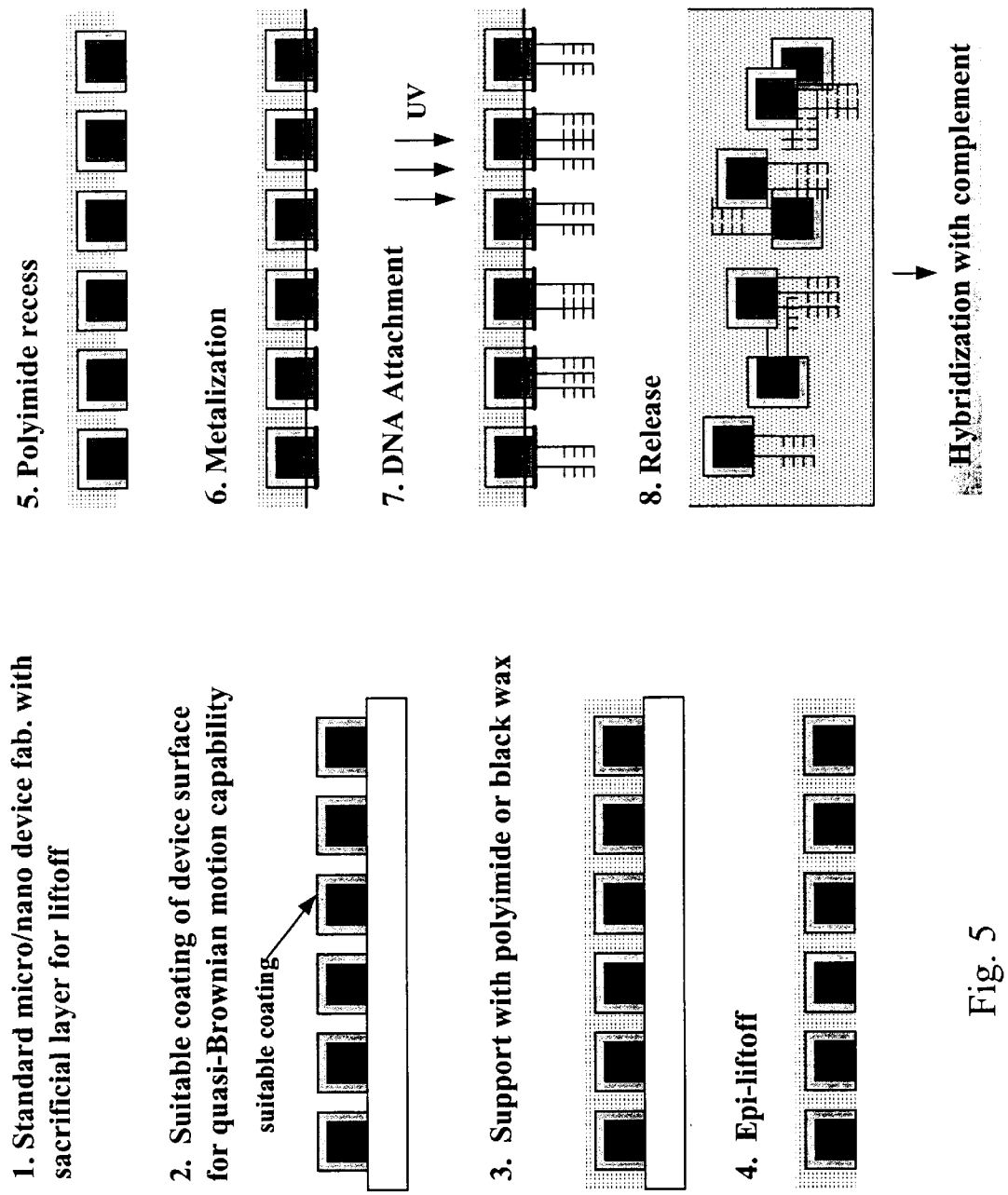
FIG. 5 shows steps for preparation of photonic devices for self assembly.

Another key step for the self-assembly process is the preparation of the sub-micron and micron-scale component devices for DNA attachment, their handling during the attachment process, and their final release into solution prior to hybridization. The epitaxial lift-off (ELO) process can substantially improve these aspects of this technique. Epitaxial films in the thickness range of 20 nm to 10 mm have been separated from their growth substrates, handled and manipulated. For example, using this technique thin III–V semiconductor films have been direct-bonded to foreign substrates, such as processed silicon wafers. Prior to lift-off, various devices can be fabricated on the films while still on their mother substrates. The first step in our self-assembly technique is the preparation of the photonic devices that are to be grafted. FIG. 5 describes a preferred process flow for this preparation step. The photonic devices are fabricated in a standard fashion on their mother substrates on a sacrificial layer as required by the ELO process. A suitable coating layer is then deposited on these devices. By controlling the characteristics of the deposited material with respect to device materials the behavior of the devices once released into the saline solution can be controlled. For example, by controlling the coating material properties the direction of the devices in the solution can be controlled. A thick polyimide film is spun to provide a physical support to the devices after the ELO process. The ELO process is carried out and the thin film devices are separated from their mother substrates. By using plasma etching, the polyimide holding membrane is recessed in areas with no devices. If needed, a metal layer can be deposited to assure good electrical contacts to the photonic devices. The DNA attachment process is then carried out and a specific DNA sequence is covalently attached on all metal surfaces. By irradiating the front surface with a UV light, the photonic devices are used as a self-aligned mask enabling exposure of polyimide areas coated with DNA polymer. In these areas, the DNA polymers react to a form that is not suitable for further hybridization. By using a solvent, the polyimide may then be removed and the devices released into the saline solution used for the further hybridization processes.

Selective DNA Hybridization Techniques

Once the host substrate is pre-programmed and the component devices are released into the solution, the self-assembly process can take place. Two different approaches for hybridization are applicable: (1) Conventional hybridization and (2) Active hybridization using an electric field.

For the conventional hybridization process, all devices may be released simultaneously into the solution. By gently agitating the devices in the solution at the proper hybridization stringency temperature and ionic strength, hybridization of the complementary DNA strands takes place as the proper device-receptor pairs come into contact. The probability of hybridization taking place may be related directly to the probability of the proper device-host pad pairs coming into contact. Since the probability distribution is most likely random, this process may take longer to achieve reasonable hybridization yields on large area surfaces unless the solution is saturated with the devices. In order to improve the selectivity and alignment accuracy several controlled heating and cooling cycles may be carried out during the hybridization process. During the heat cycle, weakly hybridized components are dissociated away to increase the chances of forming stronger bonds.

For active or electronic hybridization, the host itself or another electrode array manufacturing device are used to produce localized electric fields which attract and concentrate selected component devices at selected locations. For this process the host or manufacturing device has sites which can be used as an electrodes. A potential is applied across the solution between selected receptor sites and auxiliary electrodes. Receptor sites biased opposite (+) to the net charge (−) on selected devices, now affect the electrophoretic transport and concentration of these devices thereby increasing the rate of hybridization and binding. These sites can be selectively switched on or off using electronic or photonic addressing. A pulsing DC or biased AC electric field can be applied at a suitable frequency to eliminate the screening effect of the unwanted device types.

The electric field effect can also be used in a protective manner. In this case, the receptor pads are now biased the same (−) as the net charge (−) on the devices. The devices are then repelled from these regions and interact or bind only to those locations which have the opposite charge (+) or are neutral. Active electric field transport can be used to carry out multiplex and multi-step addressing of component devices and structures to any location on the host array.

Another important consideration during hybridization is the alignment accuracy of the photonic devices on the host or host substrate. It is assumed cylindrical photonic devices that rotation is invariant. In this case, if the device and host pad diameter is d, an alignment accuracy of d/2 may be first achieved with the natural hybridization process prior to the drying process. Devices that are misaligned with more than d/2 misalignment will not form a strong bond during the hybridization process and will not be held in place during the heating and cooling cycles of the hybridization process. Better alignment accuracy and orientation are possible when active electric field hybridization is used. Once the substrates are removed from the solution, increased surface tension during the drying process could further improve the alignment accuracy.

Metallurgical Bonding

After the hybridization process the specialty devices are held in their proper places through the formation of the double-stranded DNA structure which has a very high bonding strength. The entire assembly is then cleaned by rinsing and then dried. The DNA bond strength remains in the solid state and serves to keep the devices in place. At this point of the process, there is however, no electrical contact between the host substrate and the photonic devices. One method to achieve a metallurgical bond exhibiting an ohmic contact between the host substrate and the photonic devices is to use conductive materials on the pads and devices that can be bonded together eutectically at low temperatures. A second method is to use metals with low melting temperatures like solder or indium under a metal layer that is active for DNA attachment. While the photonic devices are held in place by the DNA bonds, the application of heat will result in the formation of a metallurgical bond. The DNA polymer will disintegrate within the bond but may only contribute to an increased contact resistance depending on the initial DNA loading factor used.

Development of Self-Assembled Emitter Arrays

As one example of the utility of these inventions, emitter arrays can be advantageously formed. Specific DNA polymer sequences may be covalently attached to semiconductor light emitting diodes (LED) and the complementary DNA sequences may be attached to receptor pads on the host silicon substrate. UV/DNA patterning techniques may be used for selective activation/inactivation of DNA on the coated surfaces. All DNA Derivitized test structures and materials will then be tested for selective hybridizability using complementary fluorescent DNA probes. LED test devices Derivitized with specific DNA sequences may be hybridized to test substrates Derivitized with complementary DNA sequences.

Development of Self-Assembled Photonic Band-Gap Structures

Photonic or crystals may be formed using the DNA self-assembly technique. Photonic Bandgap Structures are artificial periodic lattice structures in two- or three-dimensional arrangements and composed of elements of proper dimensions, density and separations. Such structures result in the modification of photonic density of states and a gap in the electromagnetic wave dispersion. Indeed, photonic bandgap structures operating at specific optical wavelengths have been demonstrated. Potential applications of photonic bandgap materials include tailoring of the spontaneous emission of a laser to achieve ultra-low threshold lazing, improved wave guiding structures without radiation loss, novel optical modulators, etc.

In one aspect of these inventions, nano-scale rods or spheres of higher dielectric constant are positioned in a medium of lower dielectric constant. A three-dimensional diamond lattice arrangement of close-packed tetrahedrally-connected dielectric spheres (200 nm in diameter and a refractive index of 3.6) embedded in a lower-dielectric-constant medium such as air exhibits photonic bandgaps. This invention relates to new ways of constructing photonic crystals by self-assembling high dielectric constant elements with desired geometry's in lower dielectric materials. In order to construct such a structure and to obtain the desired lattice geometry and nano-elements at the lattice sites, the selective attachment of DNA sequences to the nano-elements and the hybridization of finite sequences of DNA strands are employed. Metal spheres exhibiting magnetic properties may have attached DNA strands. Magnetic properties may be used to control the orientation of the spheres (or rods for 2-D crystals). The metal spheres may be dipped into a DNA solution, aligned using a magnetic field, and exposed under UV radiation. This technique allows 2D and 3D photonic-bandgap structures to be "grown" around active optoelectronic devices with minimum fabrication complexity. Additionally, because the DNA bonds connecting the nanospheres are somewhat flexible, this technique may also provide a means of realizing tunable photonic bandgap structures. The process for electronic orientation is discussed in the "Process for Electric Field Orientation Synthesis of Nanospheres and Sub-Micron Devices", below.

The various DNA polymer (oligonucleotide) sequences described above, in the 20-mer to 50-mer size range, may be synthesized on automated DNA synthesizers using phosphoramidite chemistry. Longer DNA sequences are generally required to bind larger objects to surfaces because.the binding force must be sufficient to overcome forces (e.g., shearing forces) tending to remove the object. Longer DNA sequences (>50 mers) may be constructed using the polymerize chain reaction (PCR) technique. The DNA sequences may be further Derivitized with appropriate functional groups (amines, thiols, aldehydes, fluorophores, etc.). All sequences may be purified by either PAGE gel electrophoresis or HPLC. After purification, all sequences may be checked on analytical PAGE gels for purity, and then tested for specificity by hybridization analysis.

Several DNA sequences may be used to develop and test additional chemistries for the covalently attachment to various, organic polymer based nanospheres, semiconductor, and other material substrates (glass, gold, indium tin oxide, etc.). Additional attachment chemistries provide more options and flexibility for attachment selectivity to different semi-conductor materials.

Specific DNA polymer sequences may be covalently attached to semiconductor test structures and the complementary DNA sequences to test substrate (host) materials. UV/DNA patterning techniques may be used for selective activation/inactivation of DNA on the coated surfaces. All DNA Derivitized test structures and materials will then be tested for selective hybridizability using complementary fluorescent DNA probes.

Nanospheres, nanoparticles, and semi-conductor test structures Derivitized with specific DNA sequences will now be hybridized using both conventional (temperature, salt, and chaotropic agents) and electronic (electrophoretic) techniques to the test substrates (host) Derivitized with complementary DNA sequences. The hybridization techniques may be optimized for highest selectivity and least amount of non-specific binding.

Fabrication of an LED Array

Specific DNA polymer sequences may be covalently attached to semi-conductor light emitting diode (LED) component devices and the complementary DNA sequences to host materials. UV/DNA patterning techniques may be used for selective activation/inactivation of DNA on the coated surfaces. LED component devices Derivitized with specific DNA sequences are then hybridized to test substrates (host) Derivitized with complementary DNA sequences.

Self-Assembly Fabrication of a Photonic Crystal Structure

Multiple specific DNA polymer identities may be incorporated into nanoparticles or nanospheres for the self-assembly around emitter test devices located on host materials. UV/DNA patterning techniques may be used for selective activation/inactivation of DNA on the coated surfaces. Nanoparticles Derivitized with specific DNA sequences will now hybridized to the emitter test devices located on the substrates (host) Derivitized with complementary DNA polymers.

FURTHER ASPECTS OF SELF-ASSEMBLY

Figure 30:
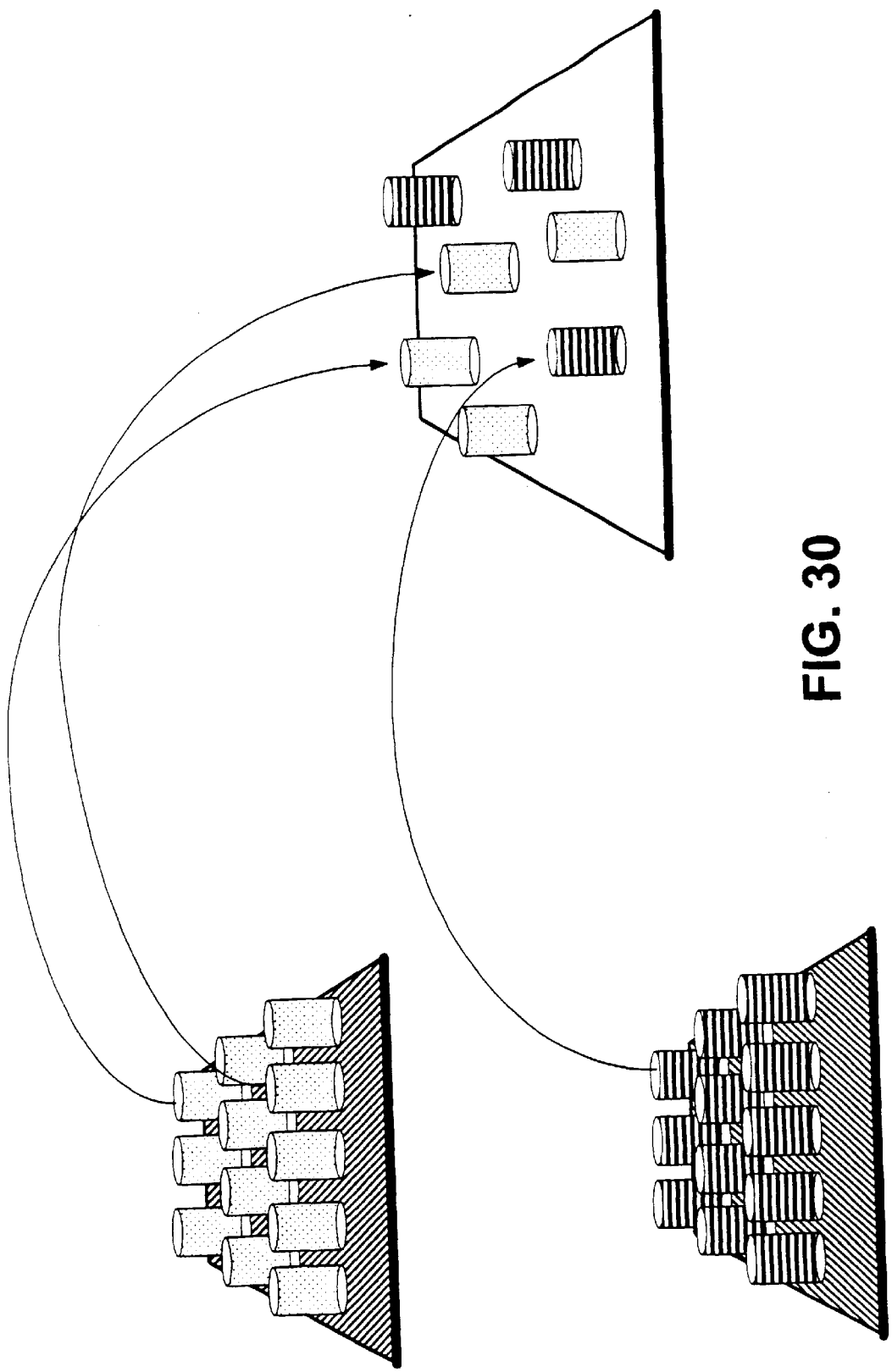
FIG. 30 shows a perspective view of global distribution of small dense structures from small dense chips on to less dense host boards.
Figure 31:
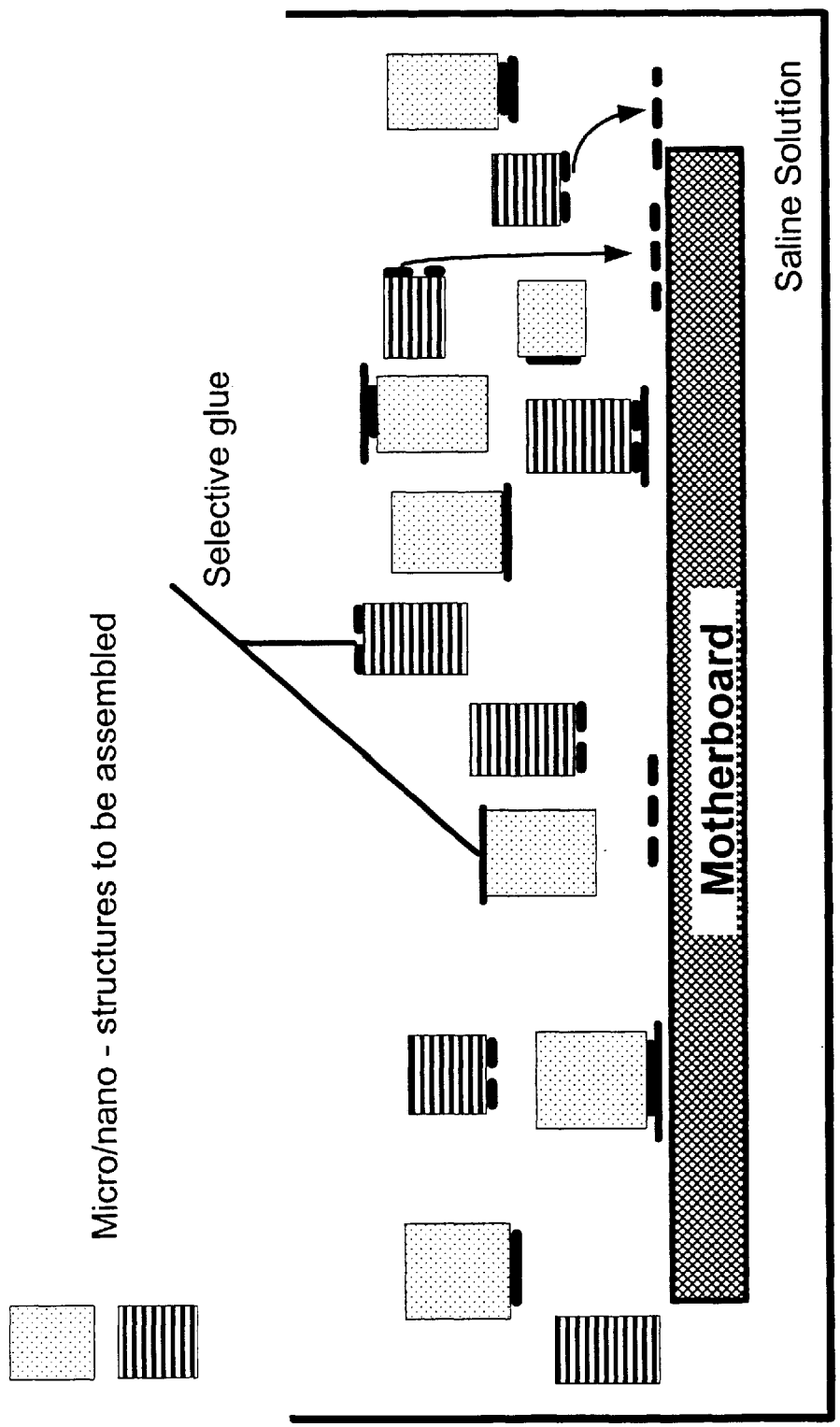
FIG. 31 shows a cross-sectional view of a structure for the self-assembly of micro or nanostructures utilizing a selective glue in which speciality devices of the given type are provided with a specific DNA polymer glue, the areas where these devices must attach being covered with the complementary DNA glue.

This invention provides for assembling specialty devices in parallel and over larger areas (up to several meters on a side) using a "self-assembly" technique. In this approach, each device to be grafted somehow "knows" where it is destined to be on the host. This invention relates to a new integration technique based on programmable self-assembly principles encountered in biological systems. This new technique removes the requirement of dimension conservation during the grafting process. Our objective is to demonstrate the self-assembly of micro/nano structures on silicon using DNA (Deoxyribonucleic Acid) polymers as "selective glues", thereby developing techniques for integrating these structures sparsely onto large area hosts. This brings together with high precision, at low cost, devices made of different materials with different real densities as shown in FIG. 30. This approach relies on the principles of programmable self-assembly found in all biological systems, and uses existing well-understood synthetic DNA chemistry as the enabling process. These techniques include: 1) remove the specialty devices from their mother substrates using the epitaxial lift-off process, 2) attach selective DNA polymer sequences onto the specialty devices using DNA attachment chemistry specially developed in our company, 3) selectively attach complementary DNA polymer sequences to proper locations on the host substrate, and 4) carry out self-assembly by using hybridization of the complementary DNA strands. This uses DNA polymer sequences as a smart and very selective glue to attach micron/nanosize specialty devices to designated areas on a host (see FIG. 31).

Selective DNA Hybridization and Electric Field Transport Techniques

Figure 7:
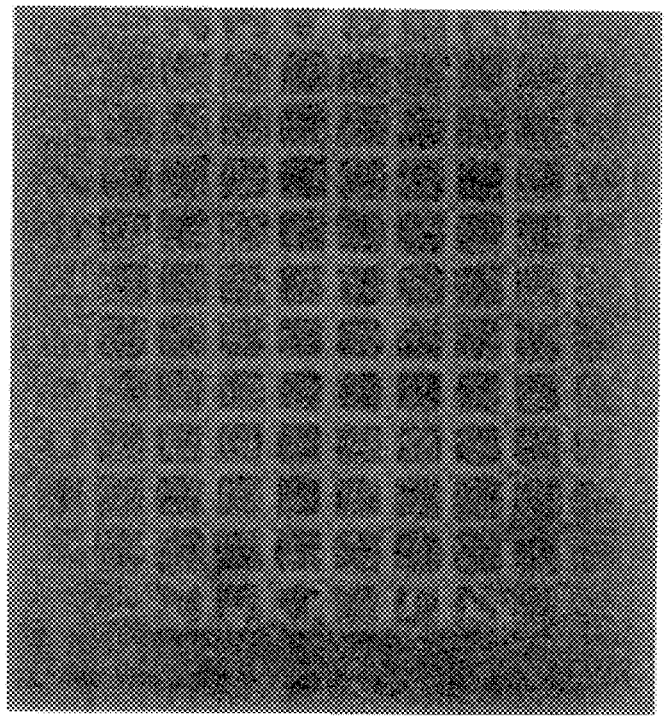
FIG. 7 is a plan view of a UV write/imaging into monolayers of DNA on silicon/silicon dioxide/aluminum.
Figure 32:
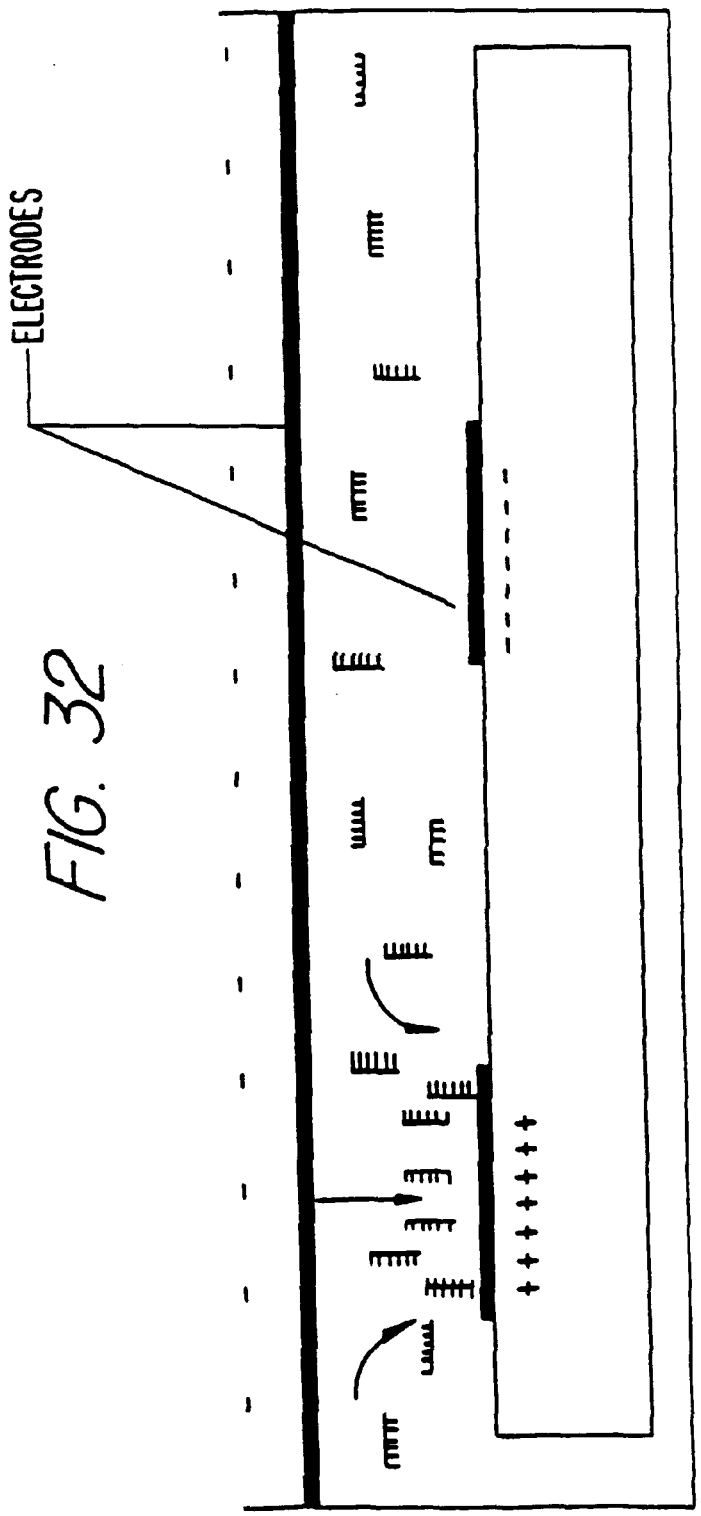
FIG. 32 shows a cross-sectional view of selective electric field deposition of DNA onto the specially derivitized microelectrode surfaces.

Techniques for the hybridization of DNA sequences to complementary DNA sequences attached to solid support materials are well known and used in many biotechnological, molecular biology, and clinical diagnostic applications. In general hybridization reaction are carried out in aqueous solutions which contain appropriate buffer electrolyte salts (e.g., sodium chloride, sodium phosphate). Temperature is an important parameter for controlling the stringency (specificity) and the rate of the hybridization reactions. Techniques exist for hybridization of DNA sequences to semiconductor materials. The first is a UV lithographic method which allow imprinting or patterning of DNA hybridization onto solid supports materials such as silicon dioxide and various metals. The second is a method for electrophoretically transporting DNA-nanostructures (nanostructures to which specific DNA sequences are attached) to selected locations on substrate materials. The technique for UV lithography with DNA involves first coating a substrate material with a molecular layer of specific attachment DNA polymer sequences. An appropriate mask can be used to imprint a pattern into the attachment layer of DNA by exposure to UV irradiation (300 nm) for several seconds. The DNA in the area on the substrate exposed to UV light becomes in-active to hybridization with its complementary DNA sequence i.e., it is not able to form the double-stranded structure. FIG. 7 show fluorescent DNA on a silicon structure was patterned with 10 micron lines using an electron microscope grid pattern. After UV patterning the material is hybridized with a complementary fluorescent labeled DNA probe, and examined epifluorescent microscopy. The fluorescent image analysis shows where the complementary probe has hybridized (fluorescent), and where no hybridization has occurred (no fluorescence). In addition to DNA based UV photolithographic type processes, other electric field based process allows derivitized DNA and charged fluorescent nanospheres to be electrophoretically transported and deposited onto selective microscopic locations on solid supports. The basic method and apparatus for this technology is shown in FIG. 32. Negatively charged DNA, sub-micron or micron-scale structures can be suspended in aqueous solutions and transported via an electric field (electrophoresis in solutions) to microscopic locations which are biased positive, relative to other locations which are biased negative. This is a particularly important technique in that it provides a mechanism to direct the transport of specifically labeled devices to specific locations on a substrate material.

Micron/Nanoscale Structure Preparation

The first step in our self-assembly technique is the preparation of the specialty devices to grafting. In this case, the specialty devices are fabricated in a standard fashion on their mother substrates on a sacrificial layer as required by the ELO process. A suitable coating layer is then deposited on these devices to assure they have a Brownian like motion in the saline solution. By controlling the characteristics of the deposited material with respect to device materials the behavior of the devices once released into the saline solution can be controlled. For example, by controlling the coating material properties we could control the direction of the devices in the solution. Once the devices are coated, a thick polyimide film may be spun to provide a physical support to the devices after the ELO process. The ELO process may be carried out and the thin film devices may be separated from their mother substrates. By using plasma etching the polyimide film may be recessed to provide sufficient steps to prevent the metal layer from being continuous. The DNA attachment process is then carried out and a specific DNA sequence may be covalently attach on all the metal surfaces. By irritating with a UV light from the front surface of the devices, the DNA areas that are exposed and not protected, may be destroyed or put in a form that is not suitable for further hybridization. By using a proper solvent the polyimide will then be removed and the devices may be released into the saline solution used for the further hybridization processes.

Preparation of the Motherboard Substrate

To delineate the areas where the grafting of the specialty devices will take place, a selective attachment procedure for the complementary DNA polymer must be carried out. The selective attachment can be realized by using the inherent selectivity of DNA sequences, selective attachment chemistries, or by directed electrophoretic transport. Alternatively after attachment, the DNA strands in unwanted regions can be destroyed by UV radiation. This approach is useful only when one group of devices need to be self-assembled.

As described in earlier sections, DNA attachment chemistry is strongly dependent on the materials used to which the DNA polymers may be attached. For example, to attach DNA to aluminum pads on a silicon chip coated with a protective glass layer, we first activate the aluminum regions by dipping the sample for a short period of time into a dilute buffered HF solution. The end result of this process is that only a few DNA strands are attached to the protective glass layer while the exposed aluminum pads are highly reactive to DNA. This material selectivity is a convenient and general way to attach DNA to the desired regions. When material selectivity is combined with UV directed inactivation and electrophoretic transport process, this allows for repeatable attachment processes to be carried out sequentially. Consider the simultaneous self-assembly of several types of specialty devices. The pads need then to be grouped according to the device to which they are to be coupled. In this case, each pad group needs to be coated with a specific DNA sequence complementary to the DNA sequence attached to the specialty device that it would be bonded to. In order to "pre-program" the host pads, each DNA sequence can be attached sequentially to the proper pads. This can be easily achieved by using the electrophoresis process and by applying a negative potential to the pads where DNA attachment is not desired. Simultaneously, a positive voltage can be applied to enhance attachment to the desired locations. For a second set of DNA sequence attachment, the procedure may be repeated with a different set of programming voltages. Thus, when the self-assembly of multiple device types need to be carried out simultaneously, the host board receiving pads may be programmed by applying a proper set of positive and negative potentials to the pads. When only one type of device needs to be self-assembled on the host board, the use of the material selectivity of the DNA attachment chemistry alone is sufficient.

Specific DNA Polymers: A Selective Glue

Figure 33:
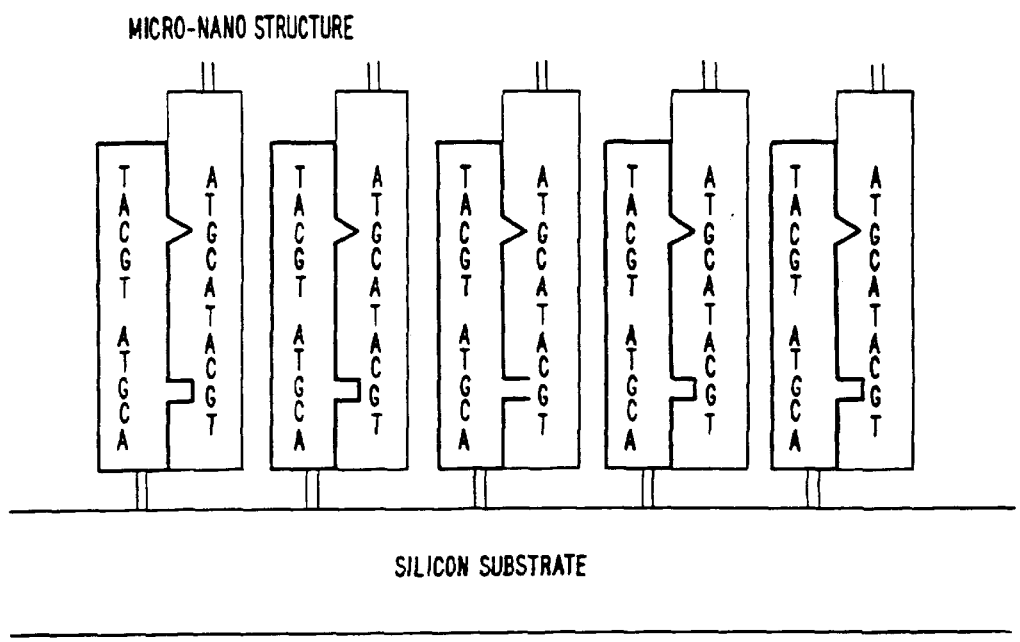
FIG. 33 shows a cross-sectional view of a micro or nanoscale structure coupled to its host board substrate by selective DNA hybridization between complementary DNA strands.

Once the host board is pre-programmed and the specialty devices are released and are freely moving in the saline solution bath, the self-assembly process can take place. At the proper (hybridization) stringency temperature, and by agitating gently the devices in the solution, hybridization of complementary DNA strands may be allowed to take place as the proper device-pad pairs come into contact (see FIG. 33). To achieve this process several different methods may be investigated.

Conventional and Electronic Hybridization

In this methods all devices may be released simultaneously into the solution, and the probability of a hybridization process taking place may be related directly to the probability of the proper device-pad pairs to come into contact. Under very simplifying assumptions, the probability of a hybridization $P_h$ may be roughly elated to the ratio of the total available pad area $A_P$ to the host board area $A_{mb}$ $$P_h \propto NA_P/A_{mb}$$

where N is the real density of one of the specialty device groups in the solution.

Since the probability distribution is expected to be random, this process may take very long times to achieve reasonable hybridization yields. Alternatively it may require the solution to be saturated with the specialty devices. This may increase the cost of the process and limit the number of types of specialty devices that can be self-assembled. In order to improve the selectivity and alignment accuracy several heating and cooling cycles will be carried out during the hybridization process. During the heat cycle, weakly hybridized components may be dissociated away to increase the chance of forming stronger bonds.

Epitaxial Lift-Off Process

A key part of the self-assembly process is the preparation of the micro/nano scale devices for DNA attachment, their handling during the attachment and finally their release into the saline solution prior to hybridization. The most popular ELO approach is to employ the selectivity of dilute HF acid on the Al GaAs series of alloys. The Aluminum rich alloys etch at a rate of approximately 1 mm/hr, while the etch rate of Gallium rich alloys is almost undetectable, less than 0.1 nm/hr. An intermediate layer of AlAs dissolves, allowing upper epitaxial layers to simply float away from the substrate. Other separation methods have also been used, including mechanical cleavage (CLEFT), and total substrate etching down to an etch stop layer. Epitaxial films in the thickness range between 20 nm and 10 mm have been separated from their growth substrates, handled and manipulated.

For example, using this technique thin III–V semiconductor films have been direct-bonded to foreign substrates, such as processed silicon wafers. The mechanical flexibility of ELO films allows a perfect conformation of the films to the substrate topography, which creates a strong and complete bond. The ELO technique then, produces a monolithic-like epitaxial thin film on an engineered substrate. Prior to lift-off, various devices can be fabricated on the films while still on their mother substrates. The ELO technique stands somewhere intermediate between a hybrid approach, such as flip-chip solder bump mounting, and a fully monolithic approach, such as direct hetero-epitaxy; it combines, however, the advantages of both. ELO is a true thin-film technology, allowing thin-film metal wiring which passes back and forth over the edge of a thin III–V film and onto a silicon micro-chip substrate. At the same time, the thin film is grown lattice-matched and essentially homo-epitaxially. Material quality, of the utmost importance for minority carrier devices such as light emitters, is never compromised. Advantages of the ELO technology over hybrid flip-chip technology include low packaging capacitance and high packing density. For high speed micro-circuits, wiring capacitance must be very low. The penalty is not merely the burden of added power dissipation. Since the series resistance of metal interconnects is not negligible, the RC time constant will ultimately act to limit the speed of opto-electronic micro-circuits irrespective of power dissipation problems, severe as they might be. The ultimate achievable packing density is somewhat scaled with respect to the working dimension of technologies. Therefore, the ELO may offer more in this aspect than the solder bump technique.

ELO films grafting on processed silicon micro-circuits requires consideration of the ultra-fine scale roughness of the deposited oxide surfaces of the micro-chip. Surface roughness interferes with the quality of the Van der Waals or metallurgical bond.

Sequential Hybridization Under DC Electric Field

To increase the probability of hybridization, a second method is to introduce each device group separately and to confine the specialty devices within regions near the positively biased pads. This confinement can be done under the influence of a DC electric field by applying a suitable positive voltage to the pads. The effect of the electric field can then be viewed as increasing the ratio of the areas, or equivalently increasing the device density, N, in the above equation. However, in this case each device group must be introduced sequentially, so the unwanted device groups do not screen the right devices from reaching the pad.

Parallel Hybridization Under an AC Electric Field

The disadvantage of the sequential hybridization is that it increases the cost of manufacturing as the types of specialty devices is increased. An alternative method is to introduce all device types concurrently into the solution, to apply an initial DC voltage to create a distribution of the devices around each pad, and then to apply an AC voltage at a suitable frequency to eliminate the screening effect of the unwanted devices types. The effect of the AC field can be seen as a stronger stirring mechanism.

Metallurgical bonds

Figure 34:
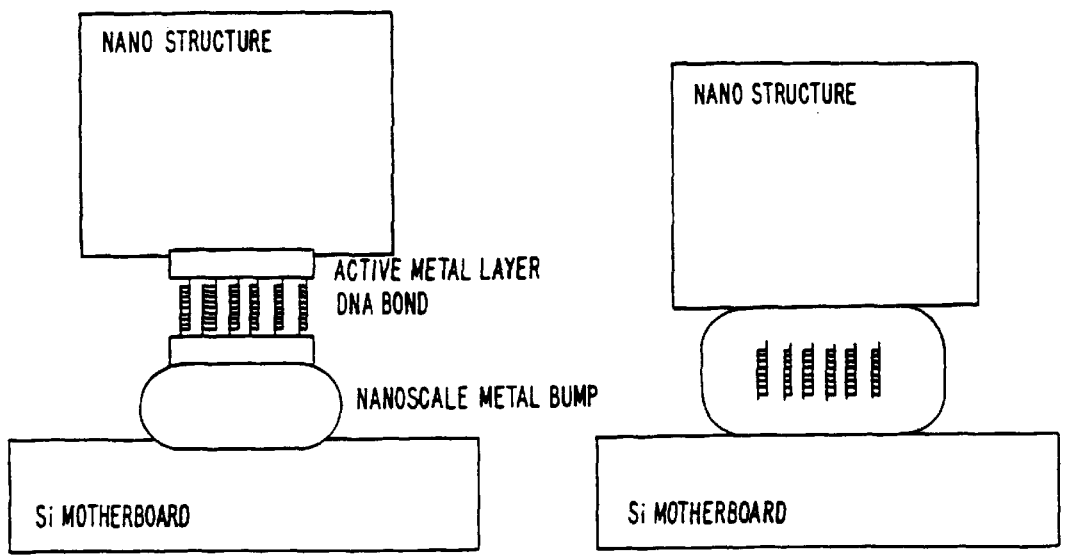
FIG. 34 shows a cross-sectional view of nanostructures held in place via a DNA bond (left-hand side) and nanostructure held by a metallurgical contact after a high temperature cycle (right-hand side).

After the hybridization process the specialty devices are held in their proper places through the formation of the double-stranded DNA structure which has very high bonding strength. The entire assembly is then cleaned by rinsing and then dried. At this point there is no electrical contact between the host board and the specialty devices. The DNA bond strength remains in the solid state and serves to keep the devices in place. One method to achieve a metallurgical bond with ohmic contact is to use conductive materials on the pads and devices that can be bonded together eutectically at low temperatures. A second method is to use metals with low melting temperatures like solder or indium under a metal layer that is active for DNA attachment. In this case the bumps must be made in nanometer dimensions. While the device are held in place by the DNA bonds, in both cases the application of heat will result in the formation of a metallurgical bond and an ohmic contact. The DNA polymer will remain within the bond but may only contribute to an increased contact resistance depending on the initial DNA loading factor used. FIG. 34 shows a the process described above.

Alignment and Orientation of the Specialty Devices

One of the critical issues that needs to be addressed in the self-assembly approach is the accuracy with which the specialty devices can be aligned to the pads on the host board. We will first assume that the specialty devices have a circular base such that the process is rotation invariant. In this case, it is expected that if the pad diameter is d, an alignment accuracy of d/2 could be achieved with the DNA bonding process. Devices that are misaligned with more than d/2 misalignment will not form a strong bond during the hybridization process and would not be held in place during the heating and cooling cycles of the hybridization process. In addition, if the nano-bump technology outlined in the previous section is employed, after the high temperature cycle for forming the metallurgical bonds, the devices may be self-aligned to the pads in a similar fashion as with the C4 technology used for flip-chip bonding.

Figure 35:
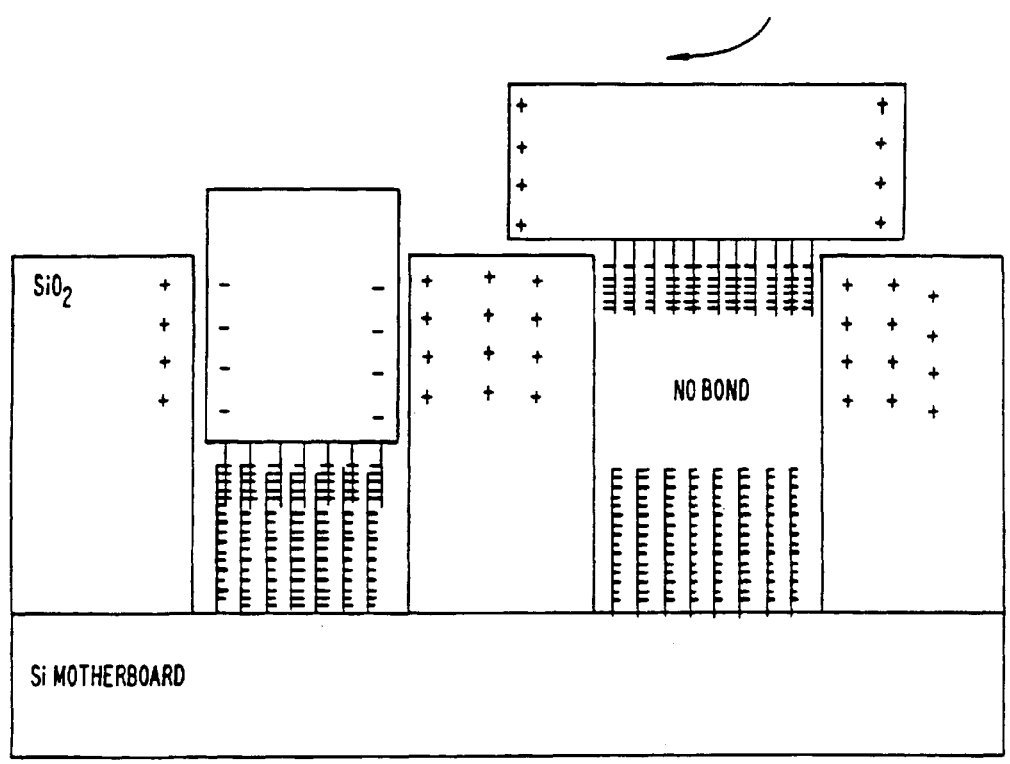
FIG. 35 shows a cross-sectional view of an apparatus for the orientation of speciality devices prior to hybridization by physical masking and charge guiding.

A more difficult issue arises if the specialty device do not have a circular symmetric base and need to be placed with a certain orientation on the pads. Two different approaches for bonding with the proper orientation may be used. As a first approach, properly patterned silicon dioxide layers are used to physically mask out specialty devices with the wrong orientations as shown in FIG. 35. The devices will fit onto the pads only if they possess the right orientation. Another approach to orient the device is to use coulombic forces prior to the hybridization of DNA. By ion implantation, or e-beam lithography exposure an opposite sign charge build-up can be realized in certain locations on the pads and on the devices. These charge patterns guide the devices to their proper orientations. As can be seen in FIG. 35, both approaches can be used together to provide DNA bonding with proper orientation of the specialty devices.

Process For Electric Field Orientation Synthesis of Nanospheres and Submicron Devices Electric field synthesis is preferably used for producing nanostructures or microstructures (e.g., nanospheres, nanoparticles, sub-micron and micro scale devices) with multiple DNA surface identities. These multiple surface identities can be in the form of specific DNA sequences which are located at different co-ordinates on the particle surface. These co-ordinates can be, for example, polar or tetrahedral in nature, and impart potential self-assembly properties which allow the nanostructures to form 2 and 3 dimensional photonic and electronic structures (such as the photonic band gap structures). FIG. 36 (upper) shows a generalized diagram of a the nanosphere (20 nm diameter) with multiple DNA sequence identities in polar and equatorial positions. FIG. 36 (lower) also shows some simple structures that could be formed by hybridizing the nanospheres together.

Figure 37:
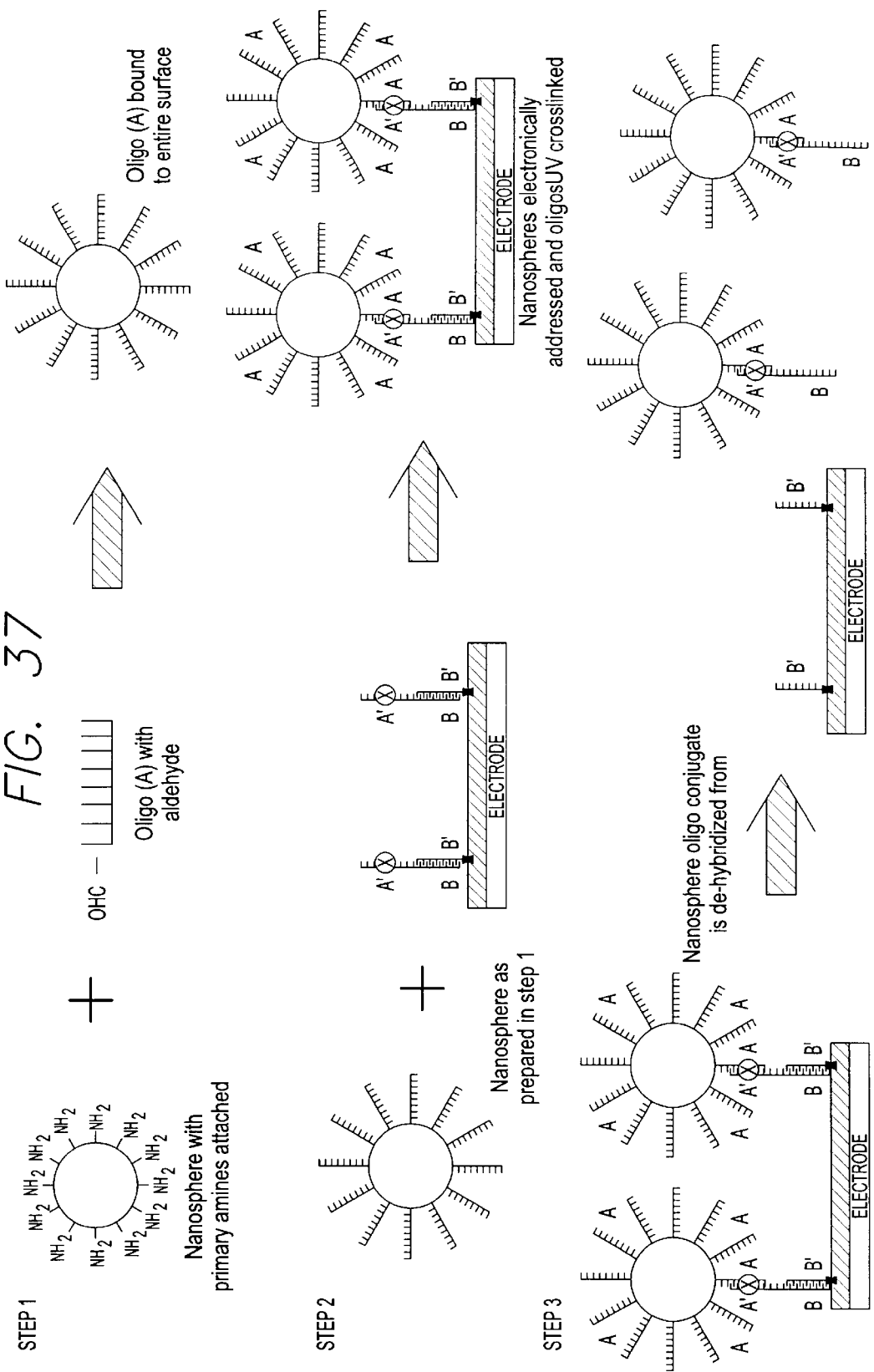
FIG. 37 shows the steps in a process for electric field orientation of devices.
Figure 38:
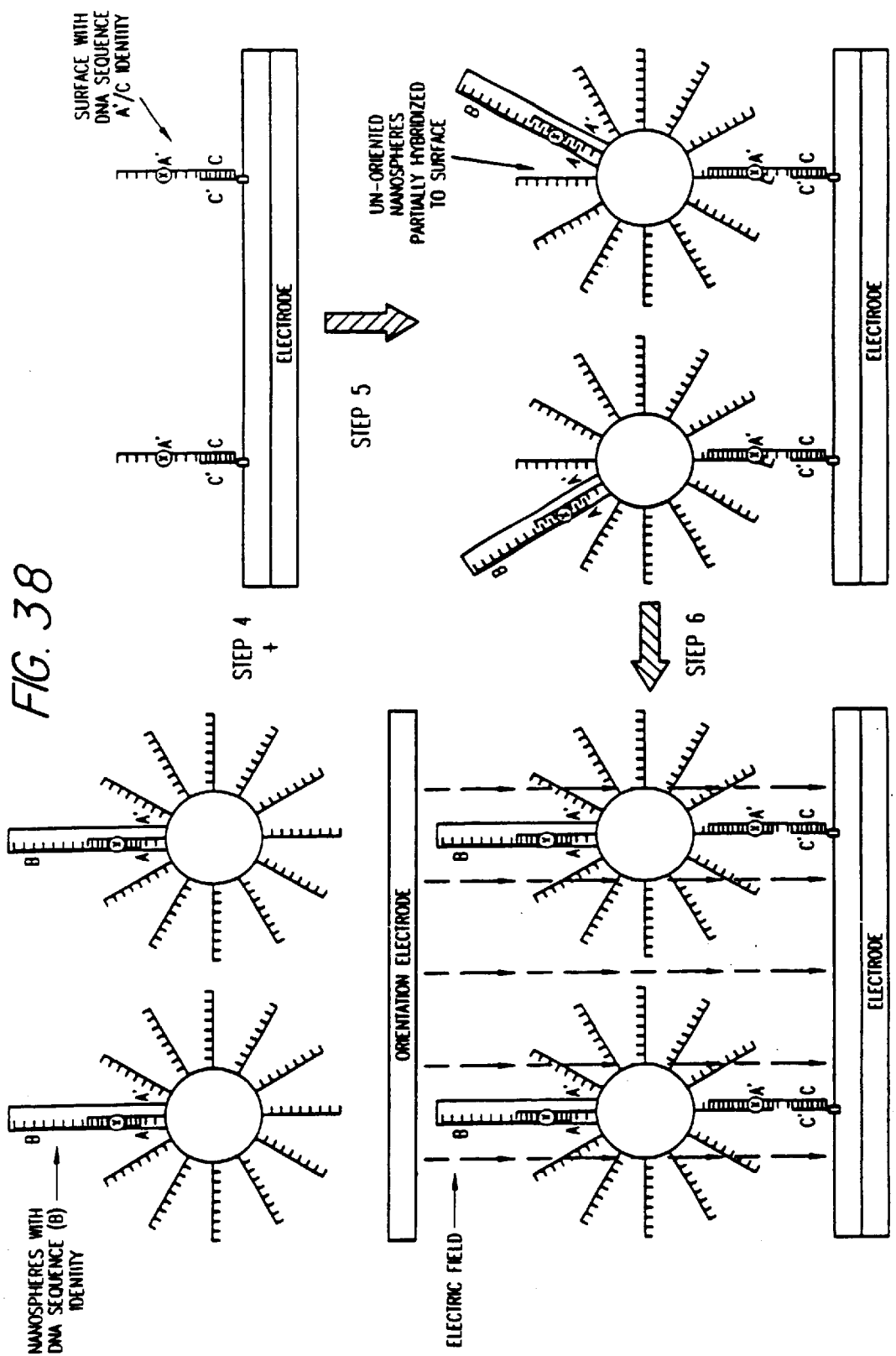
FIG. 38 shows further steps in the electric field orientation process.

FIG. 37 shows the initial steps for producing such nanostructures. In step (1), a suitably functionalized nanosphere (with amine groups) is reacted with aldehyde modified oligonucleotides with sequence identity (A). Identity (A) refers to a unique sequence of bases in the DNA; for example a 20-mer oligonucleotide with a 5'-GCACCGATTCGAT ACCGTAG-3' Sequence ID #1. In step 2, the oligo (A) modified nanospheres are now hybridized to a microlocation surface (with an underlying electrode) which has a complementary A' sequence (5'-CTACGGTATCGAATCGGTGC-3') Sequence ID #2. The (A') sequence contains a crosslinker agent (psoralen) and extends into a secondary sequence with (B) identity (5'-TTCAGGCAATTGATCGTACA-3'), (Sequence ID #3) which was in turn hybridized to a (B') DNA sequence (5'-TGTACGATCAATTGC CTGAA-3') (Sequence ID #4) covalently linked to the surface. In step 3 the hybridized nanospheres are now given a short exposure to UV irradiation which causes the psoralen moiety within the (A/A') hybridized sequence to covalently crosslink. The nanospheres are now de-hybridized (passively or electronically) from the surface. The nanospheres now have a (B) DNA sequence identity imparted to a polar position on the structures. FIG. 38 shows the continuation of the processing scheme. In steps 4 and 5, the (B) DNA sequence identity modified nanospheres are now "partially hybridized" to a new microlocation which in turn has been hybridized with a (C-A') sequence, to a complementary C' sequence which is covalently linked to the surface. The (C) sequence is different form the (A) and the (B) DNA sequences. The (B) DNA sequence nanobeads partially hybridize to the surface via the (A/A') DNA sequences, however they are not oriented in any particular fashion on the surface. Because the (B) DNA nanospheres have a non-uniform negative charge distribution on their surface (due to the extra charge from the (B) DNA, they can be oriented in an electric field. In step 6, a secondary electrode is positioned above the lower electrode, and an electric field strength is applied which is strong enough to orient the nanospheres, but does not de-hybridize them from the surface. While FIG. 38 shows the nanospheres in a polar orientation, in terms of the (B) and (C) sequences; the relative positioning of the electrodes can produce electric fields which yield other angles for the relative position of the (B) and (C) DNA sequences. When the nanospheres are in their correct alignment, they can be completely hybridized (A'-C/C'), by lowering the temperature, and then exposed to UV irradiation to crosslink the (A/A') sequences. Upon de-hybridization, this produces a nanosphere with (B) and (C) DNA sequences with relative polar (north and south) positions. We believe that repeating the process two more times can produce nanospheres with (B), (C), (D), and (E) DNA identities in polar/equatorial or tetrahedral coordinates.

Multi-Step and Multiplex Synthesis and Fabrication Techniques and Devices

Figure 39:
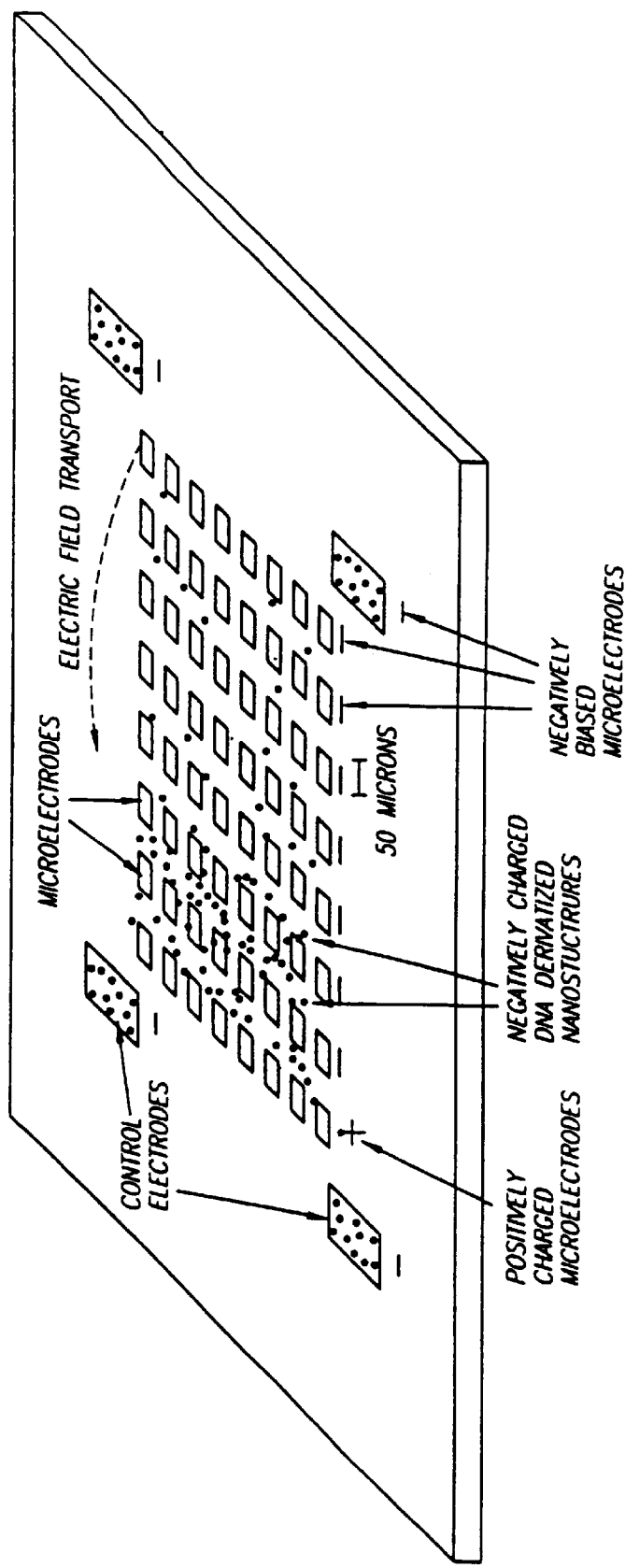
FIG. 39 shows a perspective view of nanostructure transport and assembly on a microelectronic array device.

Various techniques and devices can be used to carry out multi-step and multiplex synthesis and fabrication. FIG. 39 shows a microelectronic array device with 64 microelectrodes arranged in an 8×8 matrix, and four larger control electrodes just outside the matrix. Electrode structures on the device can range in size from ~1 micron to several centimeters or more in large scale or macroscopic versions of these devices. Permeation layers and/or template materials may be placed over such devices which would allow the devices to be used to carry out multi-step and multiplex synthesis reactions and fabrication steps on substrate materials. Thus, devices can be used for multi-step and multiplex reactions and fabrication on "themselves"; as well as manufacturing devices, which produce the assembled systems on various substrate materials. We define "multi-step" processes as these which have more than one synthesis or fabrication step at one or more locations on the device; and "multiplex" as processes involving the synthesis or fabrication of different components on different locations on the device.

FIG. 40 shows the process by which multi-step transport and positioning of nanospheres or nanoparticles can be carried out using such devices. In this sequence of figures, negatively charged nanostructures (type 1) are transported and concentrated from the bulk solution onto specific microlocations on the left side of the array. This is achieved by biasing the microlocations positive, relative to the control electrodes biased negative. The negatively charged type 1 nanostructures within the electric field are transported and concentrated (electrophoretically) at the specific microlocations. The type 1 nanostructures can be various devices or structures which have specific DNA sequences which allows them to hybridize at other specific locations on the device itself or to other nanostructures which contain complementary DNA sequences.

In the next step, type 2 nanostructures are transported and concentrated at specific microlocations on the right side of the device. In the next steps, the type 1 nanostructures are transported to specific microlocations at the center of the array which have complementary DNA attached. The type 1 nanostructures are transported to specific microlocations at the center of the array which have complementary DNA attached. The type 1 nanostructure hybridize and become specifically attached to these locations. The type 2 nanostructures are now transported to the same center location, as the type 1 nanostructures. The type 2 nanostructures are now transported to the same center location as the type 1 nanostructures. The type 2 nanostructures contain attached DNA sequences which are complementary to the type 1 nanostructures. The type 2 nanostructures hybridize and become a bound layer over the type 1 nanostructures.

Figure 41:
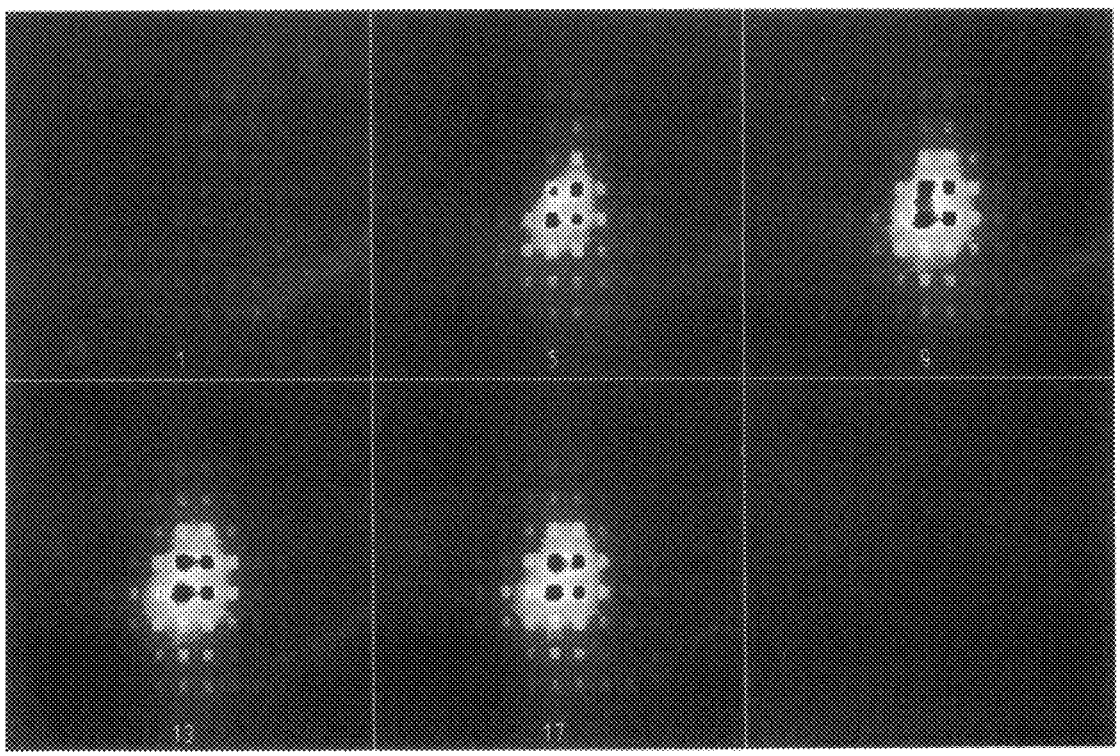
FIG. 41 shows images of an 8×8 array.

This sequence of steps in FIG. 40 is meant to depict only one of numerous multi-step and multiplex fabrication scenarios which can be carried out with these devices and self-assembling nanostructures, submicron and micron sized structures to which specific DNA sequences are attached. We refer to these processes as electric field assisted self-assembly of DNA derivatized structures. By way of example, FIG. 41 shows a sequence of photos which demonstrate the transport of 200 nanometer sized fluorescent nanospheres to selected microlocations on an 8×8 microelectrode array device. The microlocations are 501 $\mu$m×50 $\mu$m in size. The negatively charged 200 nm fluorescent nanospheres are rapidly transported and concentrated onto the positively charged microlocations. In other experimental work, nanospheres have been moved from one location to other locations on the device; and it is possible to form various patterns or arrangements of nanostructures on these devices.

Positioning and Orientation of Large Structures

Figure 42:
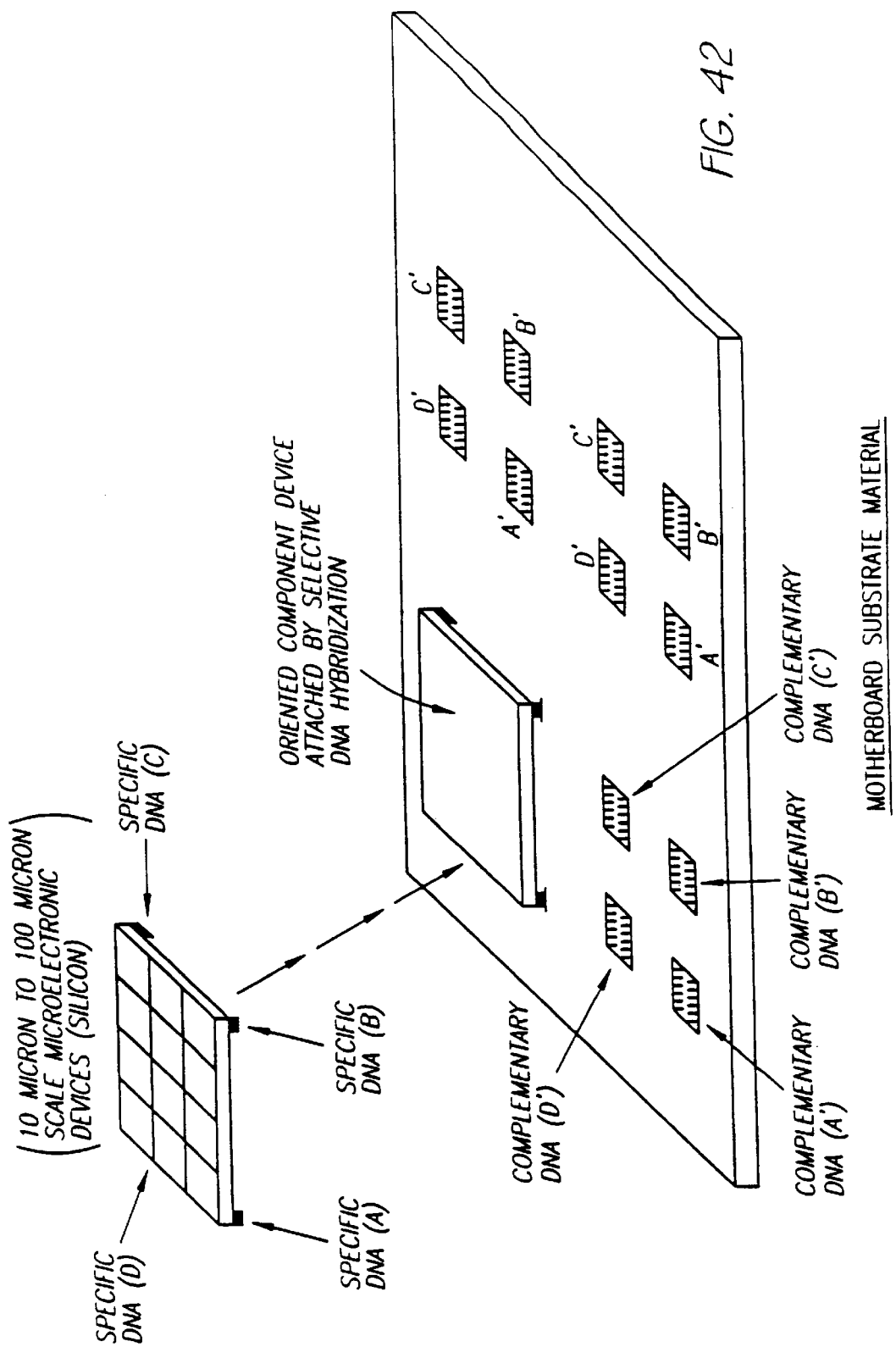
FIG. 42 shows an apparatus for attachment and orientation of larger sized devices onto a substrate or motherboard.

One useful application of this invention involves the attachment and orientation of larger (10–100 micron) sized devices onto substrate or host materials. This process is shown in FIG. 42. In this example, a device is selectively derivatized with four different DNA sequences, and the host board is selectively derivatized with the four complementary sequences. The devices are then allowed to hybridize and attach to the substrate by the processes which were described in earlier sections on passive and active electric field methods for hybridization.

Nanofabrication Within Microelectronic Parameters

Figure 43:
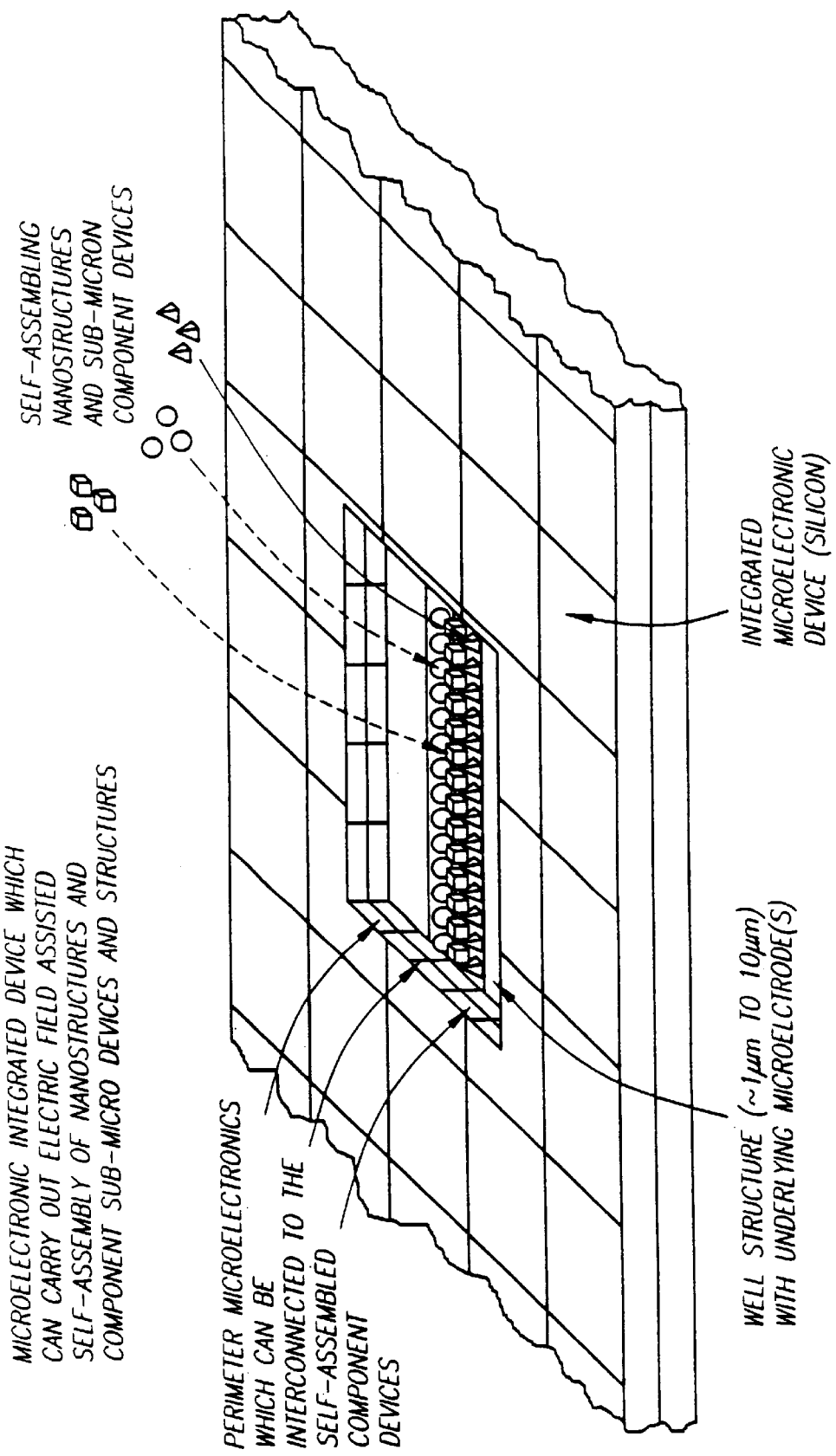
FIG. 43 shows an apparatus for fabrication of nanostructures.

Within the scope of this invention are applications which involve the nanofabrication of arrangements of nanostructures and sub-micron devices within parameters of microelectronic, optoelectronic, and optical components. In these cases, microelectronic devices are designed and built by classical procedures, but contain areas which are designed for self-assembly of nanostructures and submicron components. By way of example, FIG. 43 shows one such device. In this example, a microelectronic device built in silicon using classical photolithographic techniques, has a well structure with an underlying micro microelectrode. This microelectrode is now used to carry out the electric field assisted self-assembly of various nanostructures and sub-micron components within the parameter of the microelectronic components. This technique allows interconnection between the microelectronic components and the nanoscale components, as well as the creation of much denser integrated devices including arrangements of multiple layers (3D fabrication) of components. Thus, this invention is considered a way to synergize both classical microelectronics (optoelectronic) fabrication techniques, with self-assemblying nanofabrication techniques.

Nanofabrication Within Nanoscale Parameters

Figure 44:
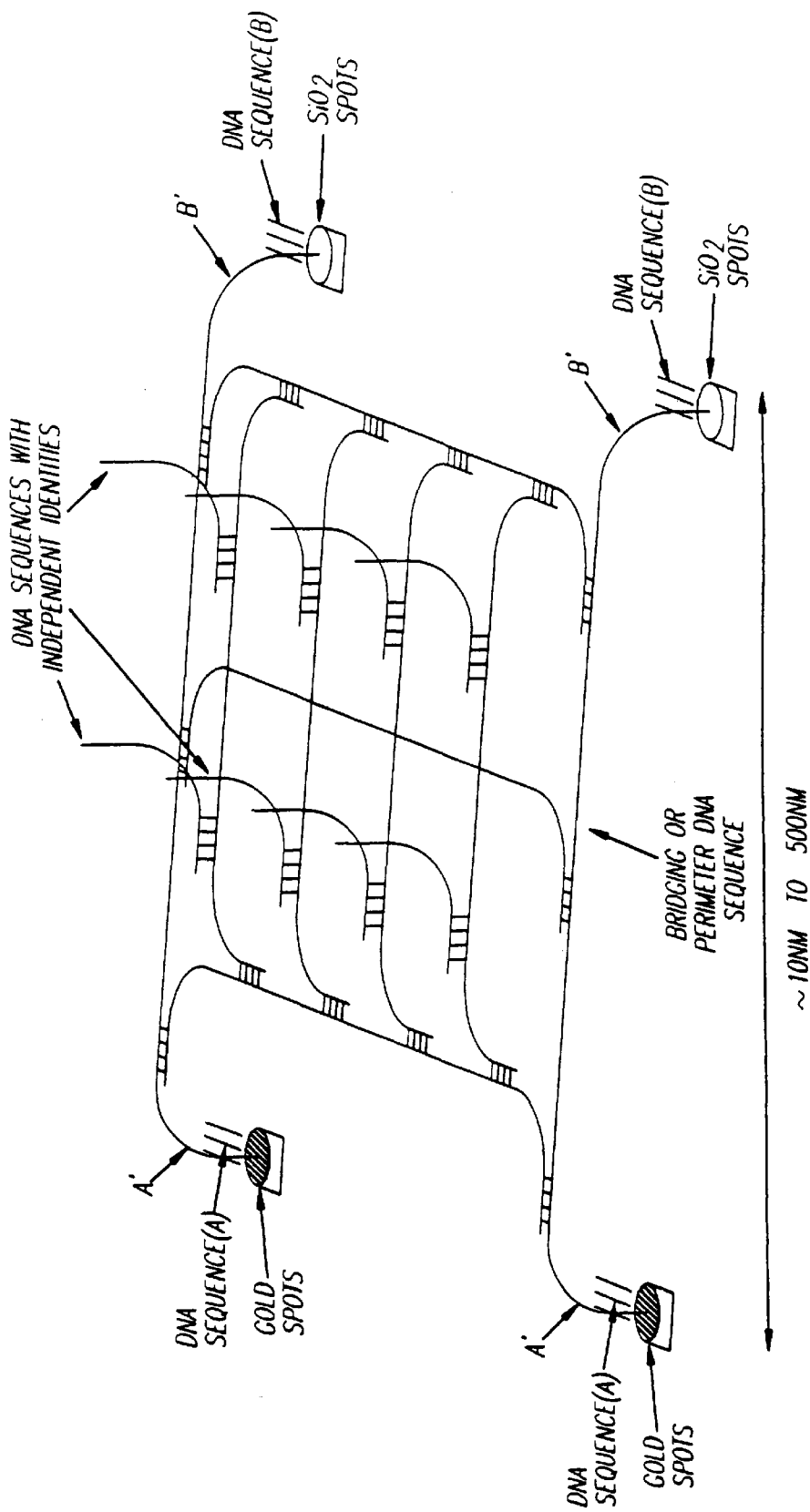
FIG. 44 shows an apparatus for nanofabrication of a nanoscale device.

Within the scope of this invention are techniques which allow the nanofabrication of the matrix of selective binding DNA sequences to be assembled with a group of nanoscale or sub-micron positions which have been deposited by atomic force, microscope, e-beam, or other sub-micron fabrication techniques. FIG. 44 shows an example of this methodology. In this example, four sub-micron attachment structures are deposited onto a suitable substrate material. Two of the structures are of material which can be selectively activated for subsequent attachment of DNA sequences (i.e., gold for thiol attachment chemistry). The other two, of a material which can be selectively activated for another specific attachment chemistry (i.e., silicon dioxide for silane aldehyde/amine attachment chemistry). From these positions two different DNA sequences can be attached. In further steps, complementary DNA sequences are hybridized which span the two different locations forming a square parameter. From proper position of other DNA sequences can be hybridized to the parameter DNA, ultimately forming a matrix structure which has selective hybridization sites within the matrix. From these types of matrix nanostructures (with selective DNA identities) a variety of two and three dimensional nanofabrications can be carried out.

METHODS AND APPARATUS FOR OPTICAL WRITING

Figure 6:
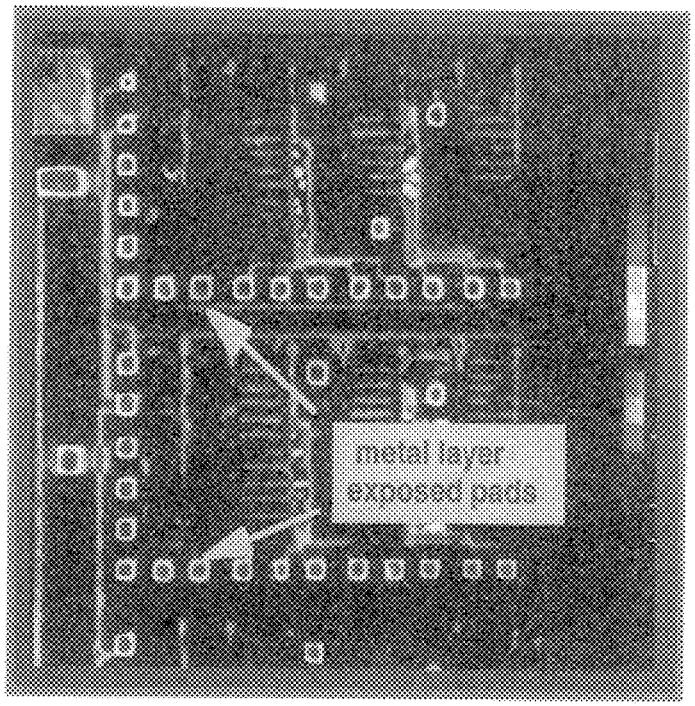
FIG. 6 shows a plan view of a structure for selective attachment of fluorescent DNA sequences to aluminum pads on silicon VLSI chips.

DNA optical storage involves the design and synthesis of chromophoric DNA polymers which absorb light energy at a single wavelength and re-emit at predetermined multiple wavelengths. Our work shows that DNA polymers can be attached in a self-organized manner to solid surfaces and made into unit cells that have the designed functionality. We demonstrated that DNA polymers attached to solid surfaces could exhibit multiple chromophoric responses, photonic energy transfer, and quenching. FIG. 6 and FIG. 7 show results related to attachment of fluorescent DNA polymers to silicon dioxide and aluminum surfaces and UV writing (imaging) into monolayers of DNA on the surface of these substrates.

UV Write Mechanism for DNA Optical Storage

Four different mechanisms exist by which information can be written into DNA substrate materials: i) spatial UV inactivation of thymidines within DNA sequences; ii) spatial UV inactivation of fluorophores and chromophores; iii) spatial UV inactivation or activation of quencher chromophores; and iv) spatial UV activation or inactivation of subsequent hybridization by crosslinking (e.g., psoralens).

Figure 8A:
FIG. 8A is a plan view of a UV image mask write followed by hybridization into DNA optical storage material.
Figure 8B:
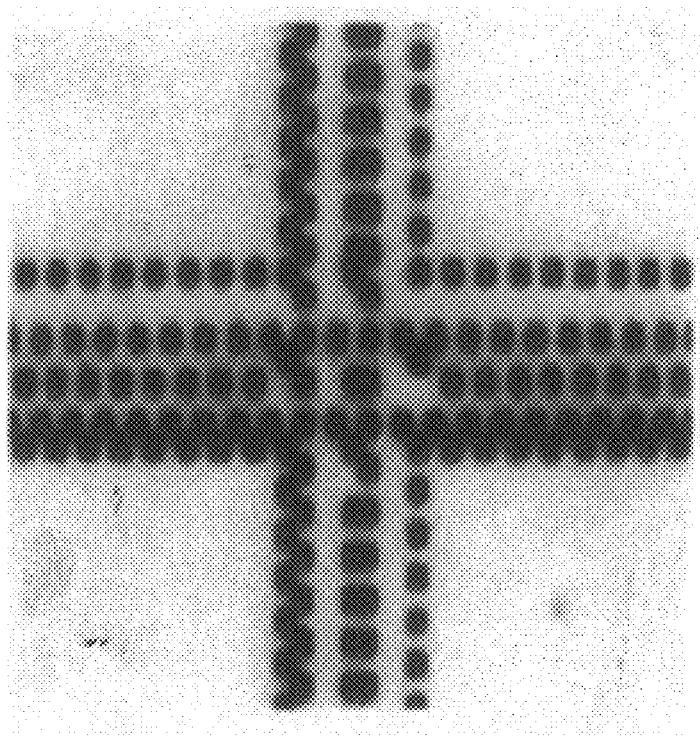
FIG. 8B is a plan view of a UV image mask write into DNA optical storage material (10 micron resolution).

FIGS. 8a and b shows UV write/hybridization results using a logo mask and a four color write mask. These represent images that are produced in monolayers of DNA on silicon substrates to which complementary fluorescent DNA sequences are hybridized.

UV/psoralen Write Process—Step 1

Regarding the UV/psoralen write process, FIGS. 9 thru 19, schematically show the complete process for preparing a "four identity DNA substrate material".

This process imparts multiple DNA identities in substrate materials using psoralen crosslinking agents. DNA intercalated psoralen compounds when exposed to low-energy UV light (365 mn) are able to covalently crosslink the DNA strands together. Linking DNA strands together with psoralen allows creation multiple identities on substrate surfaces.

Figure 9:
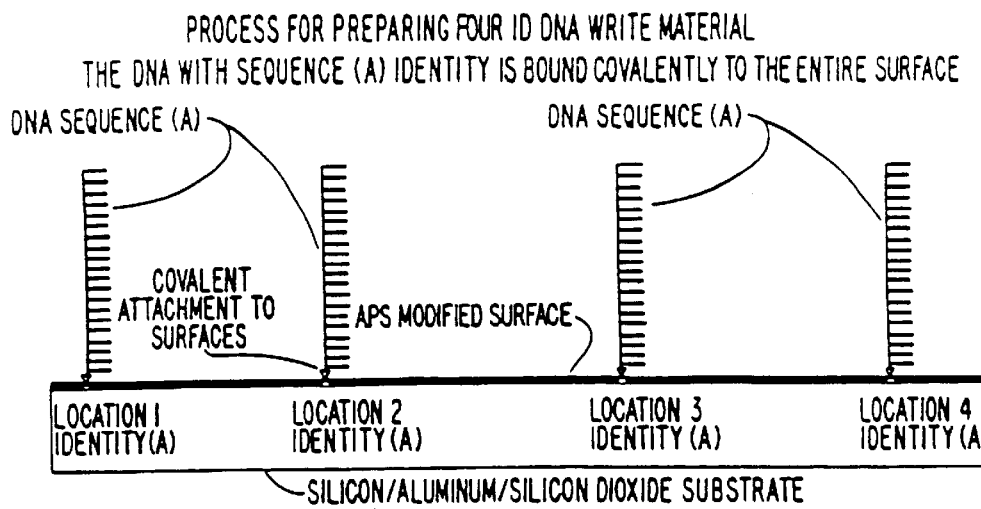
FIG. 9 is a cross-sectional view of an apparatus and method for preparing multiple write materials.

FIG. 9 shows DNA sequences with identity (A) covalently attached to the silicon/Aluminum/Silicon Dioxide substrate surface. The chip surface is first reacted with aminopropyltriethoxysilane (APS) reagent, which provides amine groups on the substrate surface for attaching the DNA sequences. The capture DNA sequences (A) are functionalized in their terminal position with a ribonucleoside group which is subsequently oxidized to form an amine reactive dialdehyde group. The DNA (A) sequences can now be covalently coupled to the amine groups on the APS functionalized substrate surface. For purposes of illustration the figures show four individual DNA strands as a way to depict the four potential write identity quadrants (refereed to as locations in the figures). In the actual material there are from $\sim 2.5 \times 10^4$ to $2.5 \times 10^5$ DNA strands per quadrant (quadrant size is preferably about 250 nm square).

Figure 10:
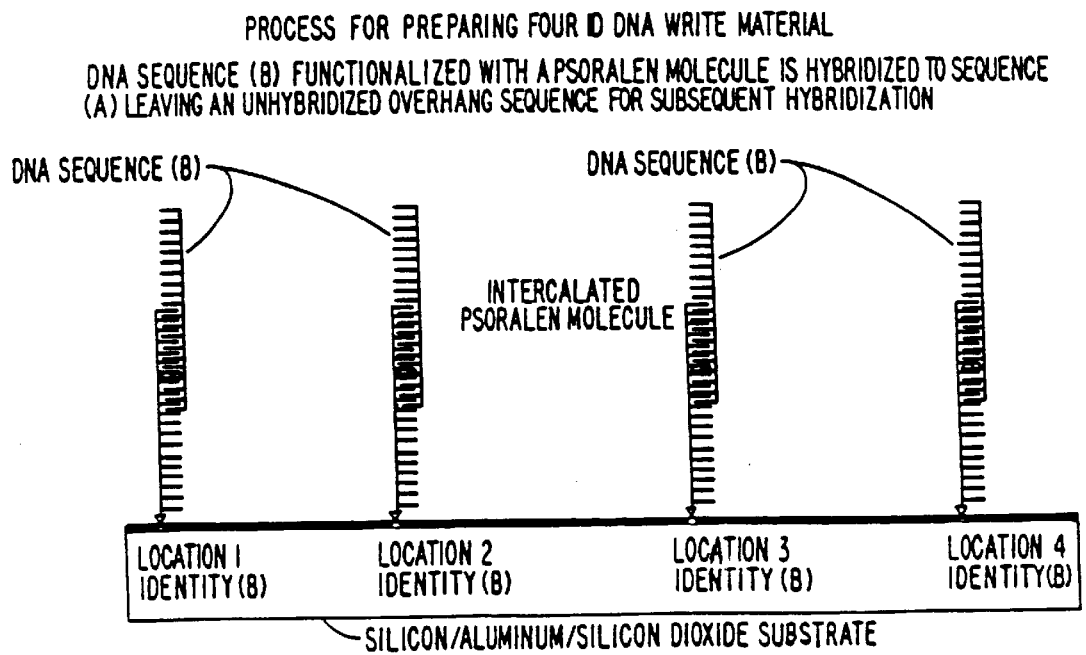
FIG. 10 is a cross-sectional view of a step in the process for preparing DNA write materials wherein a DNA sequence B is hybridized to sequence A bound to the substrate leaving an unhybridized overhang sequence for subsequent hybridization.

FIG. 10 shows the write identity process is initiated by hybridizing a (B) identity psoralen modified DNA sequence that is also partially complementary to the (A) identity capture sequence existing in all four quadrants (locations). The psoralen molecules intercalate within the hybridized double-stranded DNA.

FIG. 11 shows a UV mask is now used to block quadrant 1, while quadrants 2, 3 and 4 are exposed. The unmasked quadrants (2, 3 & 4) are irradiated with low-energy UV light (365 nm). The UV exposure causes the intercalated psoralen molecules within the hybridized double-stranded DNA to covalently crosslink the strands.

FIG. 12 shows the entire surface is now subjected to a dehybridization process. The non-crosslinked (B) identity DNA sequence in quadrant 1 is removed, leaving the (A) identity DNA sequence in that position. Quadrants 2, 3 & 4 now have the (B) identity DNA sequence in their positions.

Figure 13:
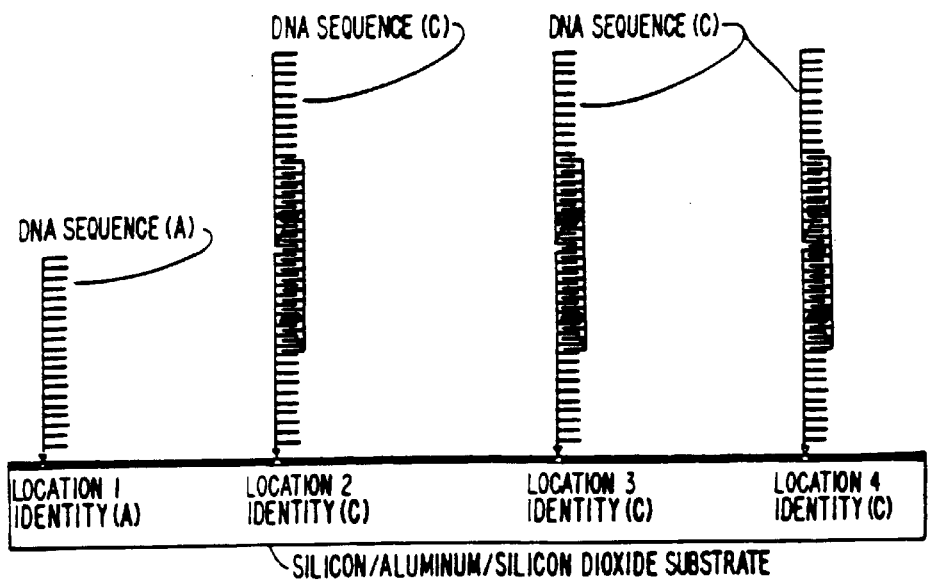
FIG. 13 is a cross-sectional view of a step in the process for preparing DNA write materials wherein a functionalized DNA sequence C is hybridized to sequence B, and the process repeated.
Figure 14:
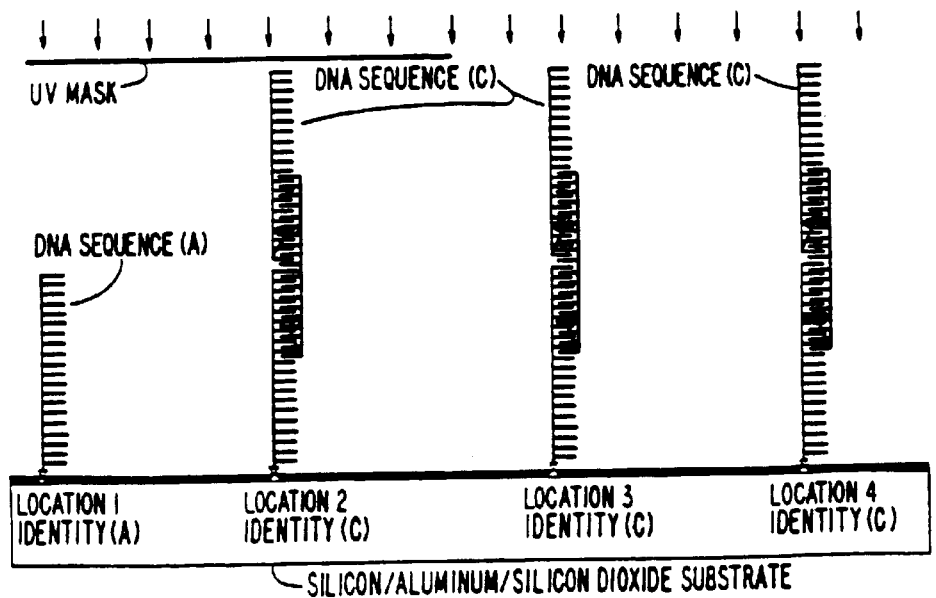
FIG. 14 is a cross-sectional view of a step in the process for preparing DNA write materials wherein locations 1 and 2 are masked while locations 3 and 4 are exposed resulting in cross-linking of sequences B and C.
Figure 15:
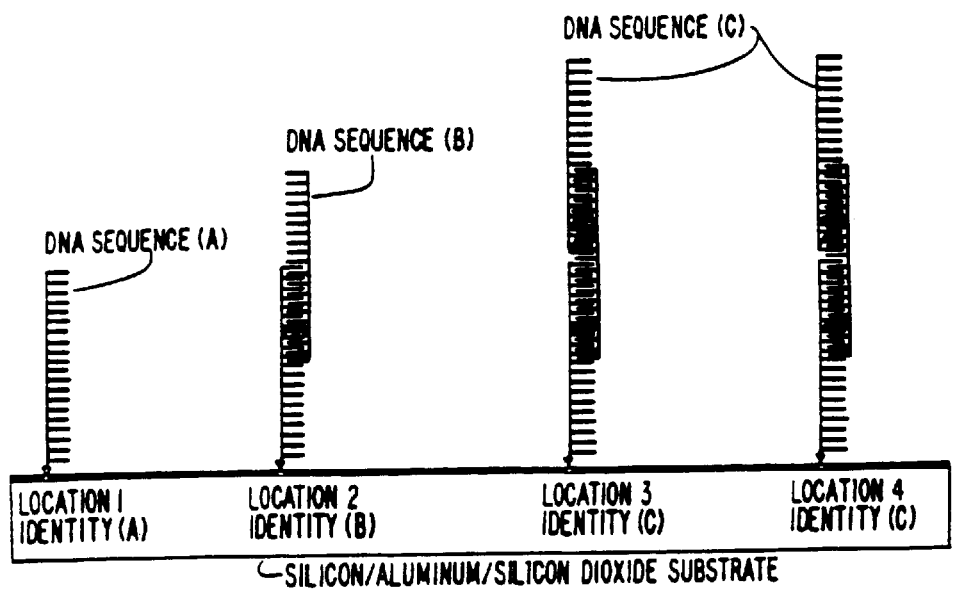
FIG. 15 is a cross-sectional view of a step in the process for preparing DNA write materials wherein dehybridization is carried out to remove sequence C from location 2, an permanent DNA sequence B being present at location 2.
Figure 16:
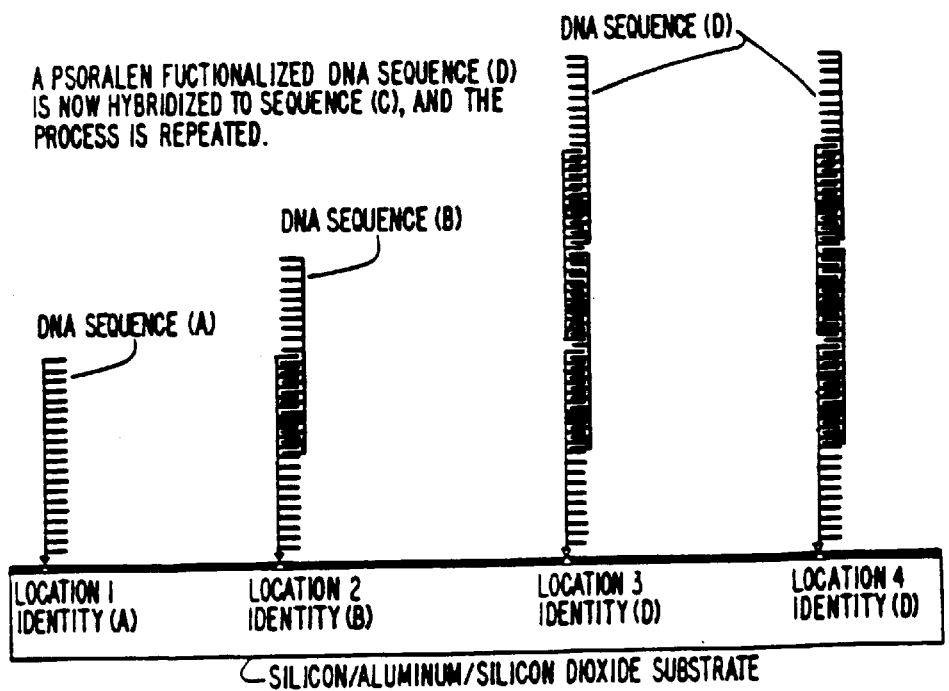
FIG. 16 is a cross-sectional view of a step in the process for preparing DNA write materials wherein a functionalized DNA sequence D is hybridized to sequence C.
Figure 17:
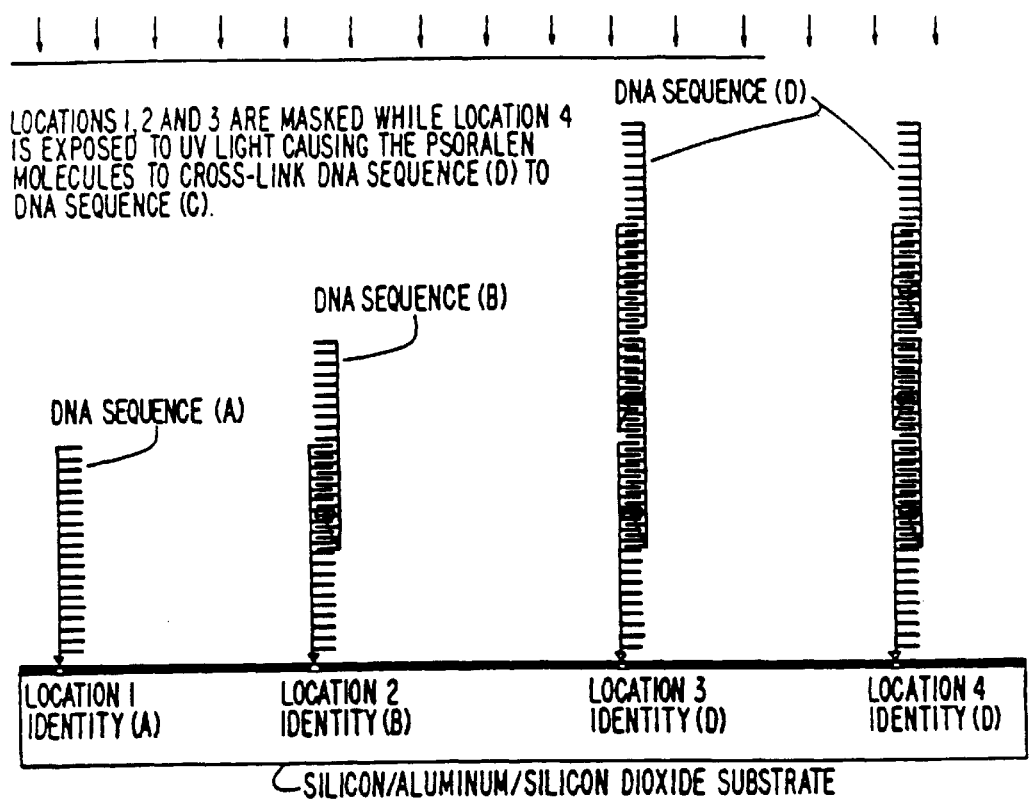
FIG. 17 is a cross-sectional view of a step in the process for preparing DNA write materials wherein locations 1, 2 and 3 are masked while location 4 is exposed to light causing the cross-linking of DNA sequence D to DNA sequence C.
Figure 18:
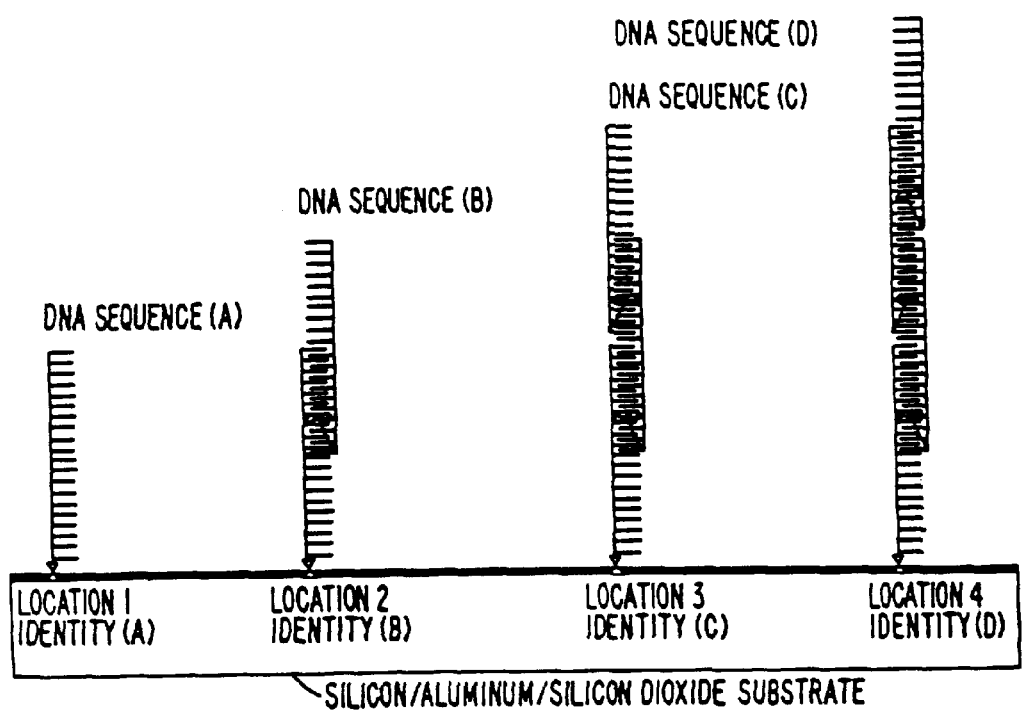
FIG. 18 is a cross-sectional view of a step in the process for preparing DNA write materials wherein dehybridization is carried out to remove DNA sequence D from location 3, a permanent sequence C being present at location 3 and a permanent sequence D being present at location 4.

FIG. 13 shows the process is now repeated with a (C) identity DNA sequence, containing the partial (B) identity DNA complement, being hybridized to the (B) sequence in quadrants 2, 3 and 4.

FIGS. 14 thru 18 depict essentially the repetition of the processes shown in FIGS. 9 thru 13. When completed, the final material contains four separate DNA identity sequences (A, B, C, & D) each located in a separate quadrant.

FIG. 19 shows, at this point, where one can check the specificity of the four DNA sequences (A, B, C, & D) by hybridizing the four fluorescently labeled complementary sequences to the surface. Each quadrant should now produce its specific fluorescent color.

UV/psoralen Write Process—Step 2

The actual information UV write process (to the four DNA identity substrate) is carried out by another masking and UV exposure procedure (see FIGS. 20, 21, and 22). In this case, a higher energy UV irradiation (254 nm) is used to render the DNA in the UV exposed regions non-hybridizable. When DNA is exposed to this higher energy UV light, the thymidine bases within the DNA sequence dimerize and prevent any further hybridization from occurring. This procedure can thus be used to inactivate the individual quadrants or "turn them off". When the fluorescently labeled complementary DNA sequences are hybridized to the material, only the quadrants with hybridizable complementary DNA sequences will have the appropriate fluorescent color. This is the mechanism by which data can be selectively written into DNA.

FIGS. 20 & 21 show turning "On" the B and D identities, and turning "Off" the A and C identities. Before the UV write process is started, the specific A, B, C, & D sequences in all four quadrants 1, 2, 3, & 4 are hybridizable. The write process is initiated by masking quadrants 2 and 4, and exposing the surface to the high-energy (254 nm) UV irradiation. Quadrants 1 and 3 are now effectively inactivated or made unhybridizable by UV exposure, while the DNA sequences in 2 & 4 remain hybridizable.

FIG. 22 shows how the material can now be hybridized with the fluorescent DNA complements to all four DNA identities, however, only the fluorescent DNA complements to the B and D identities will effectively hybridize and produce the final fluorescent colors. The UV write process being completed, the material now has two distinct fluorescent colors in the B and D quadrants, and no fluorescent colors in the A and C quadrants.

Experimental Demonstration of Two Color DNA Write Process

Figure 23A:
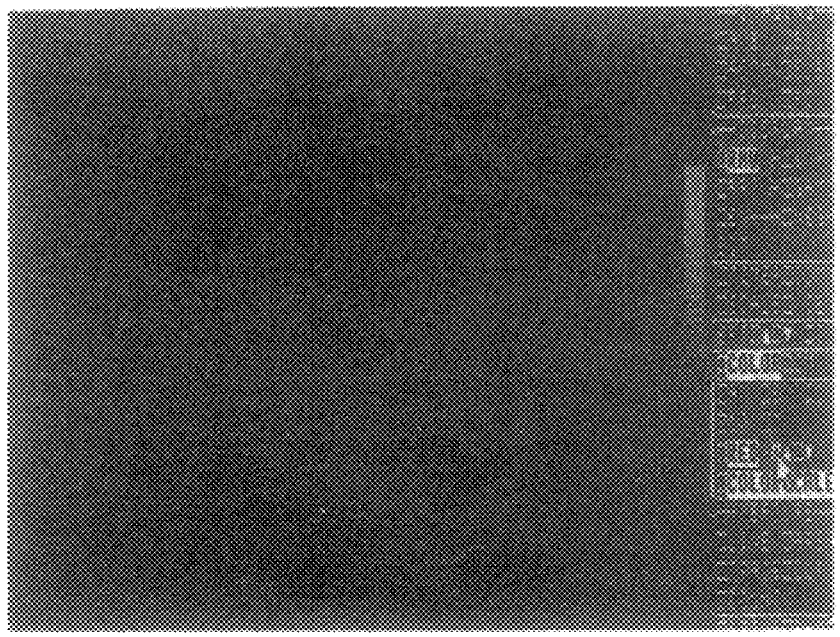
FIG. 23A is a planned image of the background fluorescence for APS-reacted silicon substrate surface before DNA attachment.
Figure 27A:
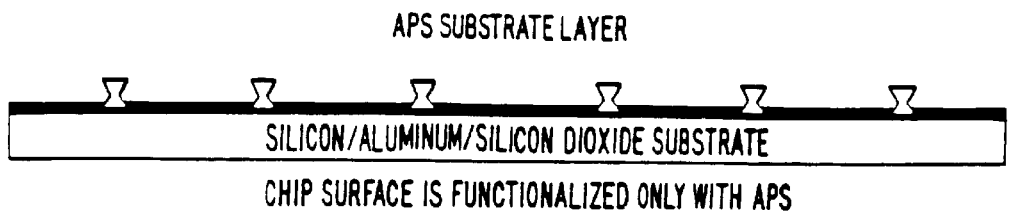
FIGS. 27A, B and C are cross-sectional views of apparatus and method steps for forming fluorescently labeled sequences, wherein FIG. 27A specifically shows a substrate with a functionalized surface.

We have demonstrated two color write using the psoralen/UV process. The series of process and write steps are described below in the text. FIGS. 23A&B, 24A&B, and 25A&B show the actual photographs of the substrate and fluorescent write materials. FIGS. 27A, B&C, and 28A, B&C, provide further schematic descriptions of the process.

Figure 23B:
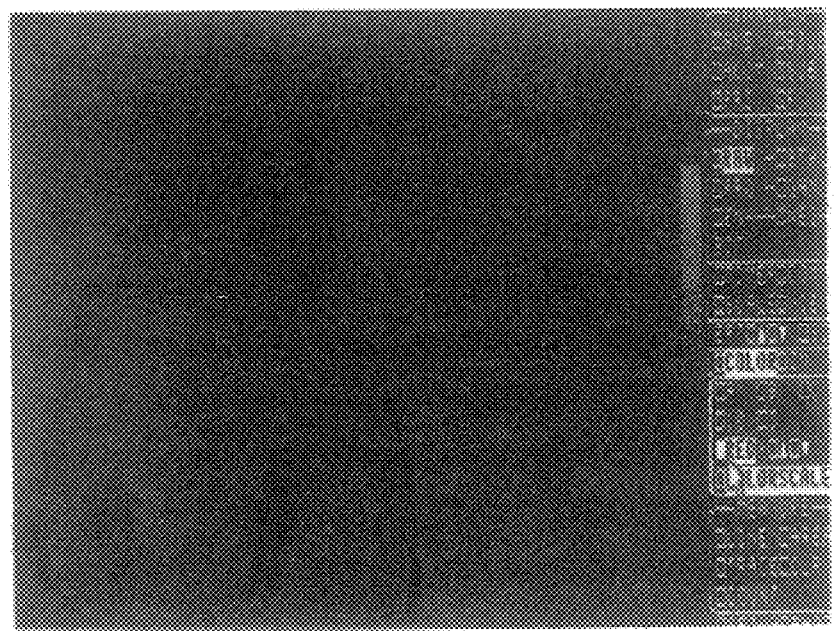
FIG. 23B is a planned image of the background fluorescence level after capture DNA is bound to the APS-reacted substrate.
Figure 27B:
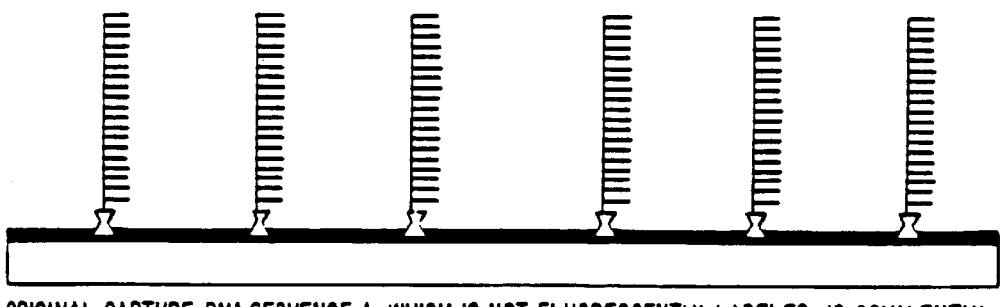
FIG. 27B shows a substrate with a functionalized surface further with a capture sequence A attached to the functionalized surface.
Figure 27C:
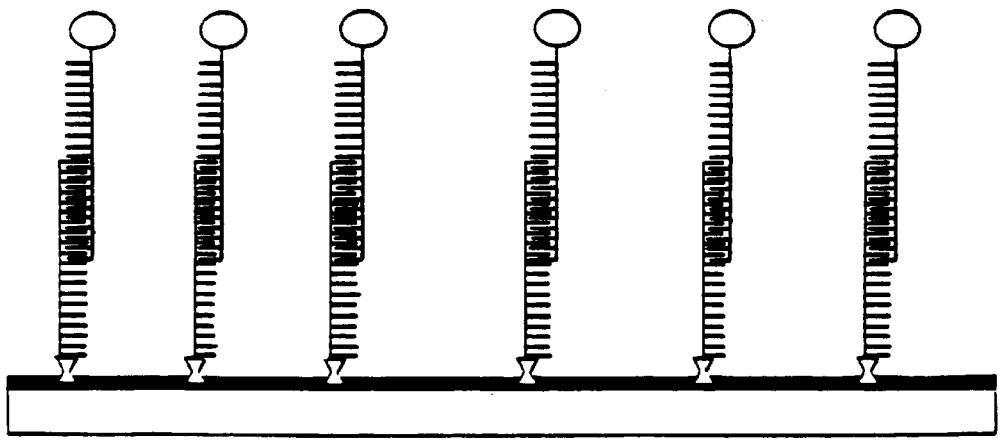
FIG. 27C shows the substrate with the functionalized surface, sequence A and labeled complementary sequence hybridized.

Step 1: A control chip surface (Silicon Dioxide/Aluminum/Silicon) was treated with Aminopropyltriethoxysilane (APS). FIG. 23-A shows the chip surface appears basically black, because of the relatively low level of background fluorescence. FIG. 27-A is a schematic representation of the material at this point of the process. All photographs were taken using the Jenalumar Epi-fluorescent microscope/Hammamatsu Intensified CCD Camera/Argus Ten Imaging system.

Step 2: A second control chip surface (APS reacted) was then reacted with the DNA (A) identity capture sequence that contains the proper base composition for subsequent psoralen crosslinking. The DNA (A) sequence has a ribo group on the 3' end that is oxidized to a dialdehyde, this reacts with the amine groups on the surface to covalently attach the DNA. FIG. 23-B shows a photograph of the substrate surface with the DNA (A) present, but without any fluorescent complementary DNA present. The chip surface still appears black, because of the relatively low level of background fluorescence. FIG. 27-B is a schematic representation of the material at this point of the process.

Figure 24A:
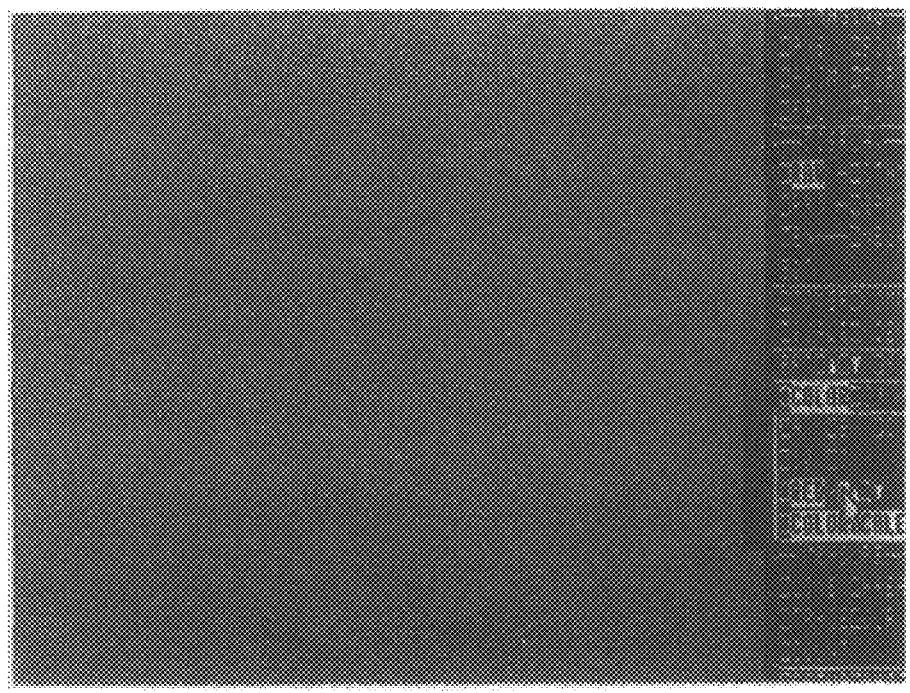
FIG. 24A is a planned image of a chip treated with APS and capture DNA and then hybridized with a Bodipy Texas Red labeled complementary probe sequence ac ross the entire chip surface.
Figure 24B:
FIG. 24B is a planned image of the chip surface after hybridization of a fluorescent Bodipy Texas Red labeled complementary probe to the non-psoralen cross-linked identity on the right side of the chip surface.

Step 3: A third control chip surface which has been APS reacted and has the DNA (A) capture sequence attached, is hybridized with a Bodipy Texas Red fluorescently labeled complementary sequence. FIG. 24-A now shows the entire chip surface producing intense red fluorescence. FIG. 27-C is a schematic representation of the material at this point of the process.

Step 4: A fourth chip is treated with APS and (A) identity DNA capture sequence is then bound to the surface as in Step 2.

Step 5: The complementary (B) identity sequence, with a psoralen molecule attached, is then hybridized to the (A) identity sequence over the entire surface.

Step 6: One half of the chip surface is masked, while the other half is exposed to low-energy (365 nm) UV light. This causes the covalent crosslinking of the (A) identity DNA sequence with the (B) identity DNA sequence.

Step 7: The surface is then treated with a 0.1 normal Sodium Hydroxide solution to remove (dehybridize) the non-crosslinked DNA from the masked side of the chip. At this point one half of the chip is covered with covalently linked (B) identity DNA sequence, and the half contains the original (A) identity DNA sequence.

Figure 28A:
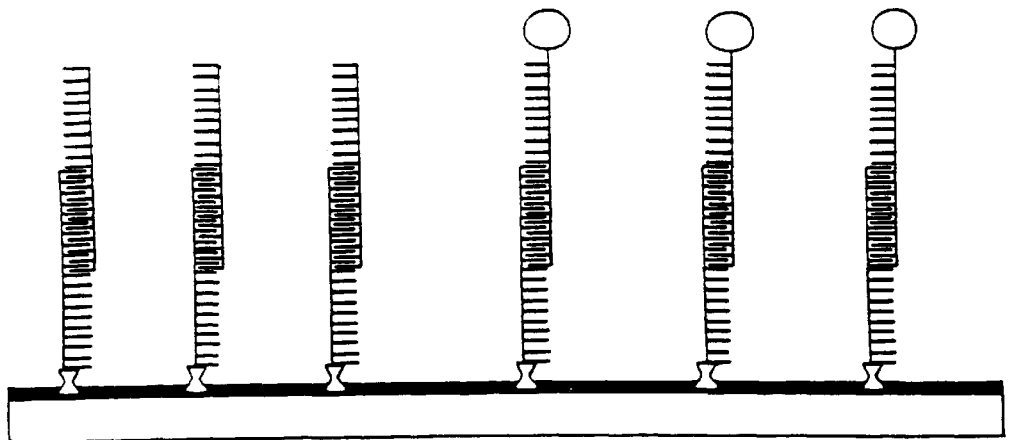
Figure 28B:
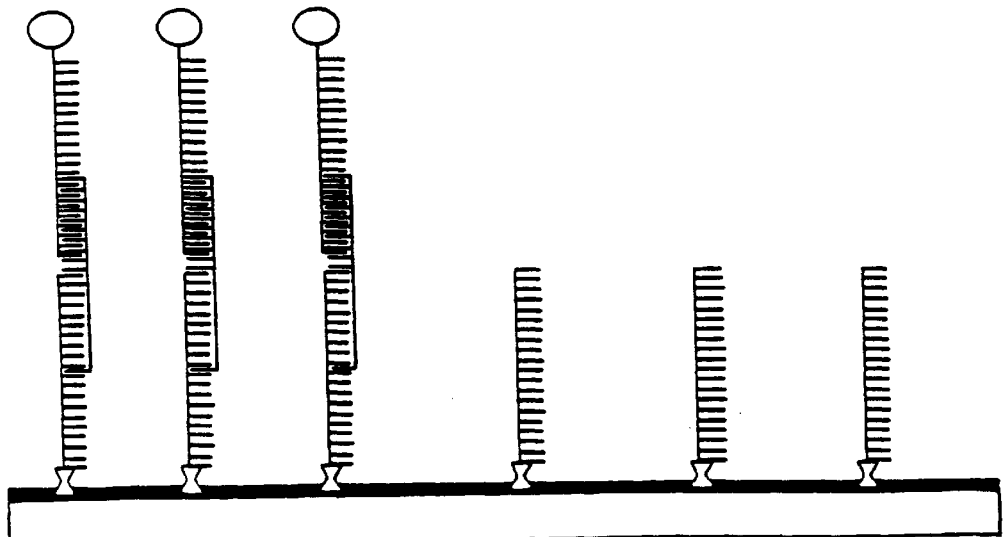
Figure 28C:
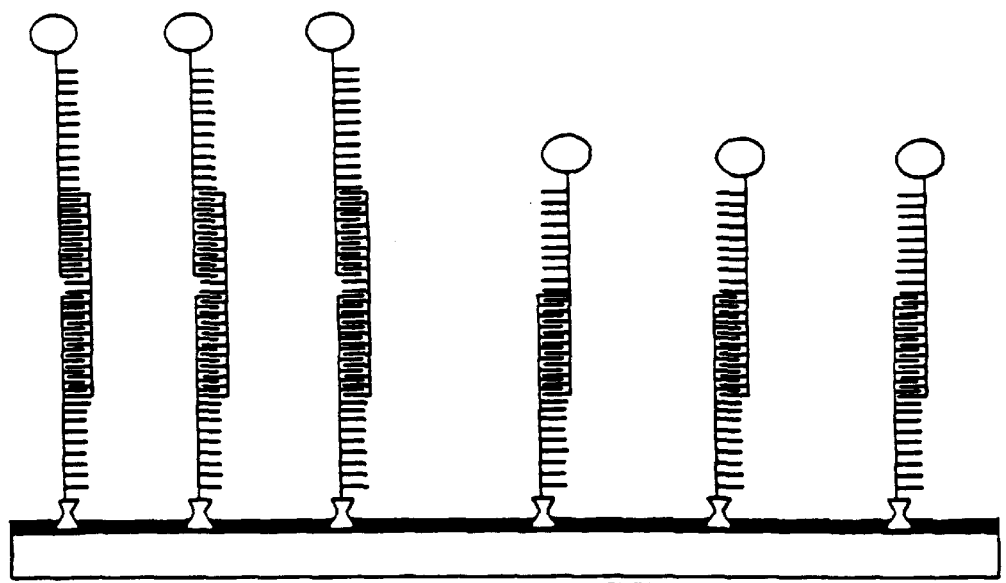
Figure 29:
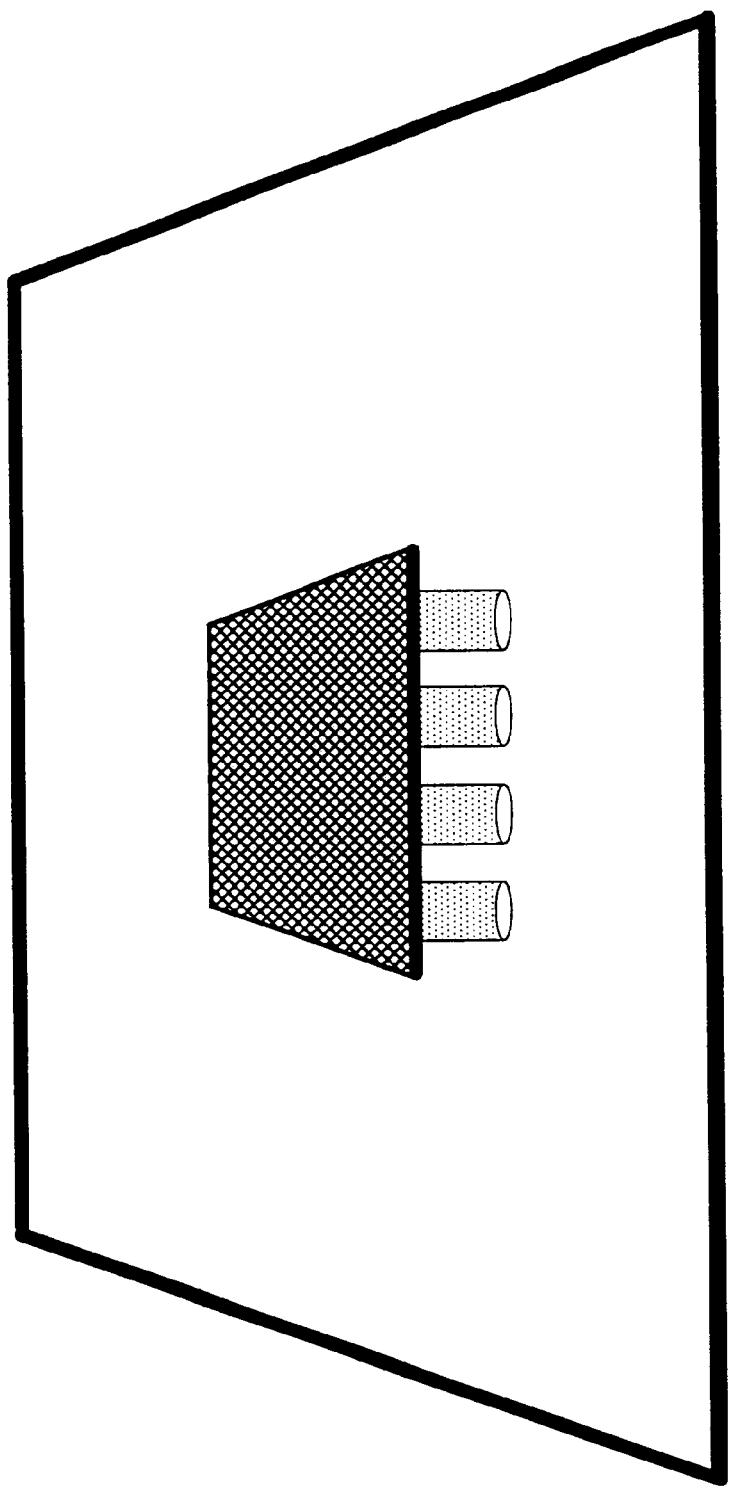
FIG. 29 is a perspective view of a flip-chip bonding arrangement which conserves the geometrical dimensions leading to the coupling of small dense arrays of specialty devices onto local regions of host boards.

Step 8: A complementary (A) identity DNA sequence labeled with Bodipy Texas Red fluorescent dye (excitation maximum 595 nm and emission maximum 626 nm) is now hybridized to the chip. The complementary fluorescent (A) identity DNA sequence hybridizes only to the half of the chip surface containing the (A) identity capture sequence (FIG. 24-B). FIG. 28-A is a schematic representation of the material at this point of the process. Steps 4 thru 7 are repeated on a fifth chip surface.

Figure 25A:
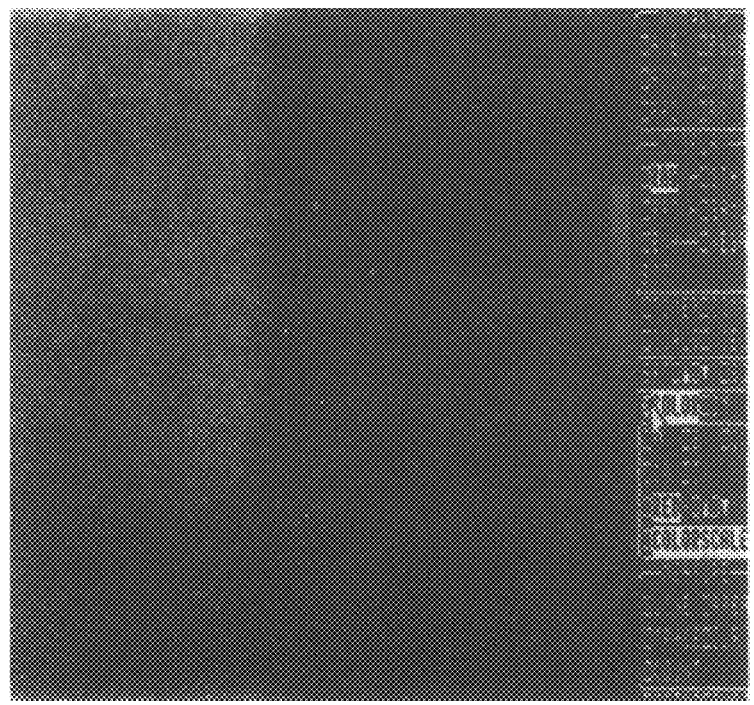
FIG. 25A is a plan image of the chip surface after hybridization of a fluorescent Bodipy Orange (b) complementary probe to the (b) sequence identity on the left side of the chip surface.
Figure 25B:
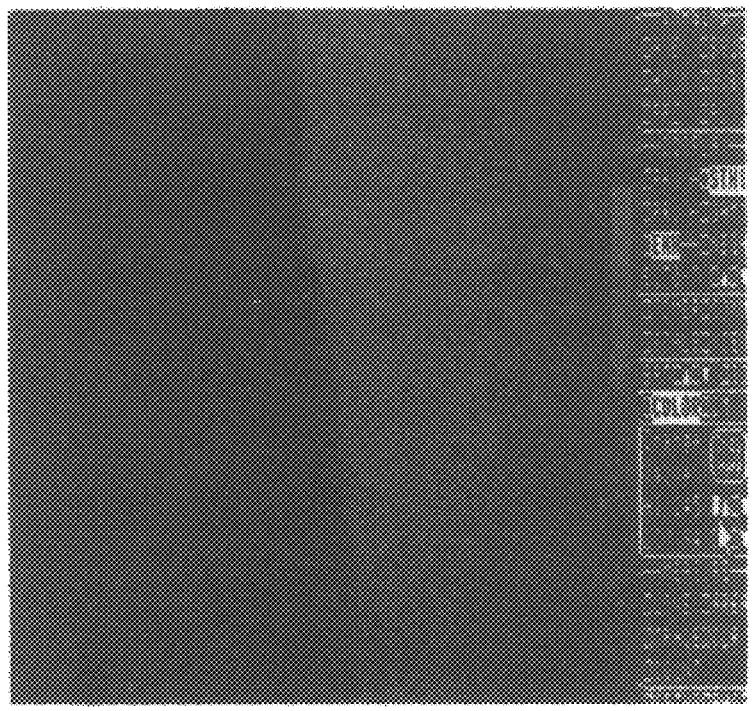
FIG. 25B is a plan image of the chip after both crosslinked (B) and non-cross-linked (A) sides are hybridized with their respective fluorescently labeled complementary DNA (A) and (B) probes.

Step 9: A BODIPY Orange fluorescent dye (excitation maximum 558 nm and emission maximum 568 $\mu$m) labeled sequence complementary only to the (B) identity sequence is then hybridized across the whole chip. This DNA sequence hybridizes only to the half of the chip containing the (B) identity (FIG. 25-A). FIG. 28-B is a schematic representation of the material at this point of the process.

Step 10: A sequence complementary only to the (A) identity capture sequence, labeled with BODIPY Texas Red fluorescent dye is hybridized to the fifth chip. Again this fluorescently labeled DNA attaches only to the half of the chip containing the (A) identity. The chip now contains both identities with their corresponding colors (FIG. 25-B). FIG. 28-C is a schematic representation of the material at this point of the process. With the results showing exclusive hybridization of two distinct sequences to two separate parts of a chip surface (FIGS. 24-B, 25-A & 25-B), we are reasonably confident that the above protocol is indeed capable of producing multiple identities on silicon substrate surfaces.

Experimental Demonstration of 160 nm Nanosphere Binding To Substrate

Figure 26A:
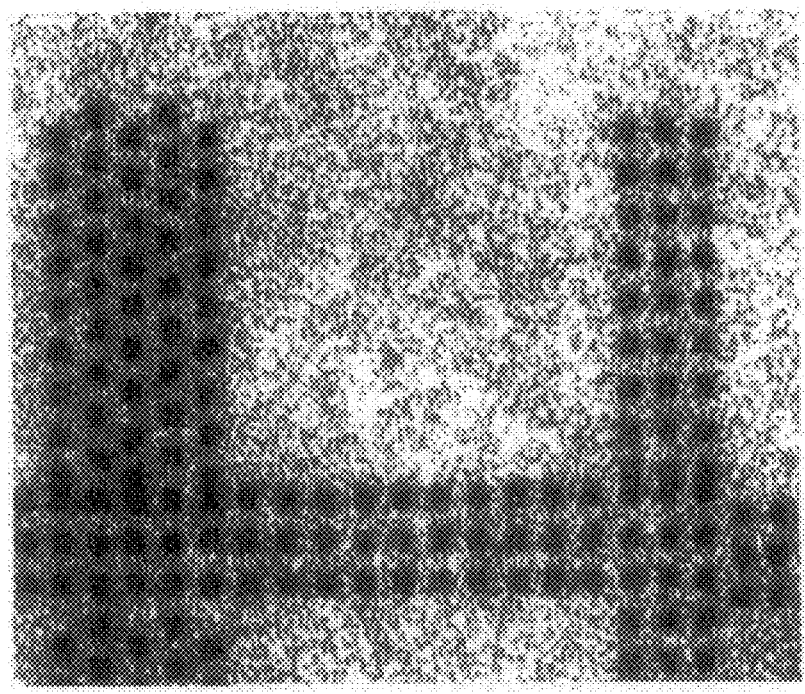
FIG. 26A is a plan image of 160 nanometer beads (white spherical features) electrostatically bound to a DNA polymer layer covalently bound to a silicon dioxide derivitized surface with partial specificity, having 10 micron square dark features where the DNA field has been UV inactivated, the nanospheres not binding in these areas.
Figure 26B:
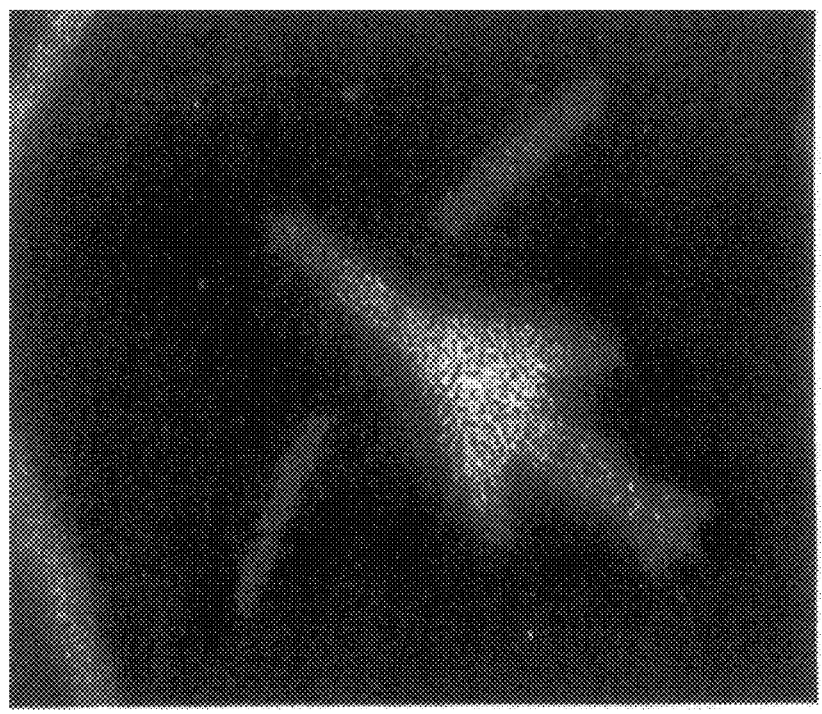
FIG. 26B is a plan image of a pattern image constructed with 160 nanometer beads (white spherical features) wherein the nanospheres are electrostatically bound to a DNA polymer layer covalently bound to silicon dioxide derivitized surface with partial specificity, the dark areas showing areas where the DNA field has been UV inactivated, the nanospheres not binding in these areas.

FIGS. 26A and 26B show results on attaching 160 nm DNA Derivitized fluorescent nanospheres to a DNA Derivitized silicon dioxide surface. The nanospheres are bound to the image sections with the active DNA, as opposed to the DNA in-activated sections. The binding is believed to be due to electrostatic as well as to hybridization interactions.

Low Density Optical Memory Applications

A number of important applications of DNA based optical data storage and memory are possible in areas regarding incorporation into documents, currency, labels, and other items. The use of fluorescent energy transfer and chromophoric DNA based mechanism for these "low density" application would have advantages over bar codes and other methods in use because of the extreme difficulty in attempting to counterfeit such information or coding.

A Photo-Electronic Optical Memory Write Systems and Devices

Figure 45:
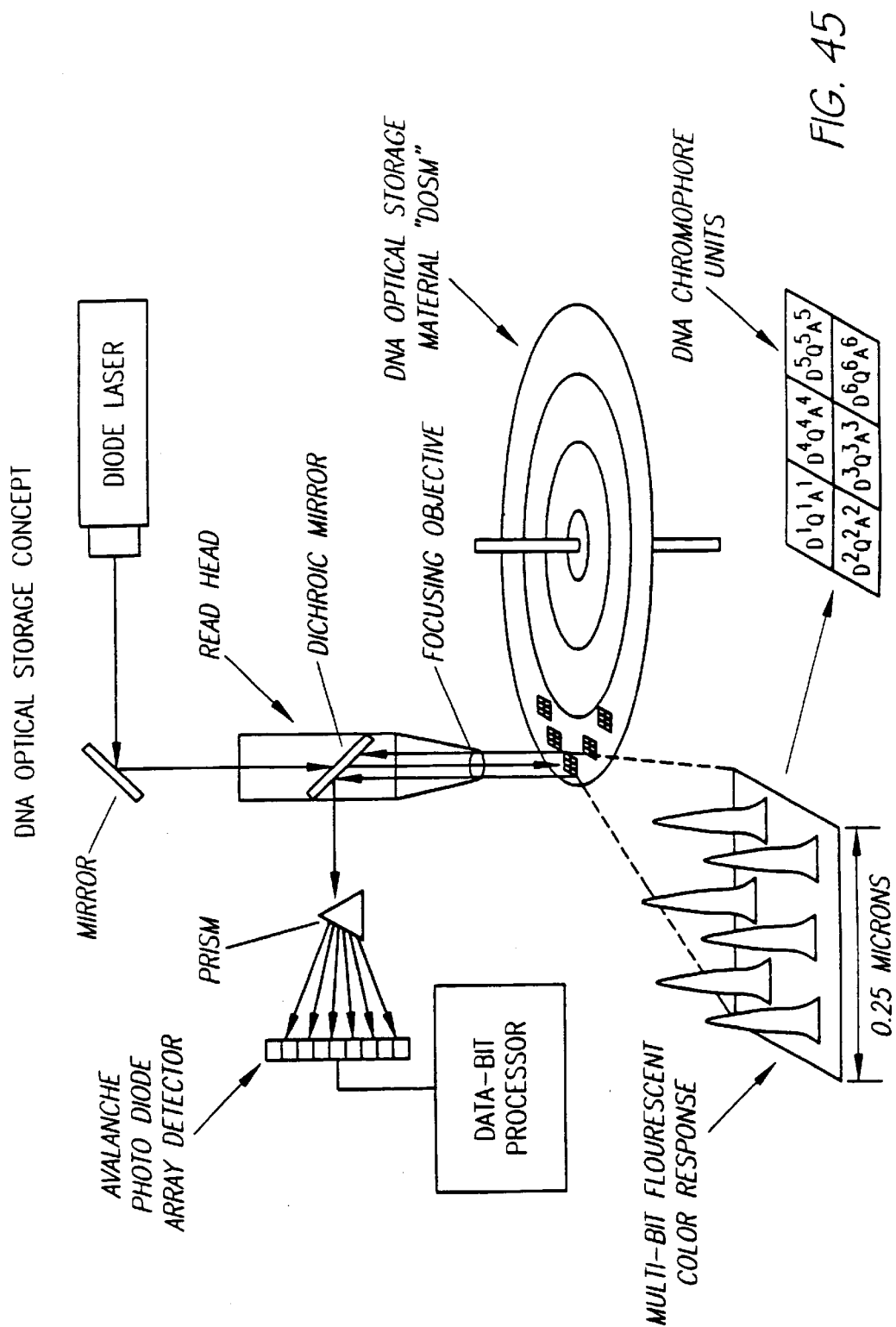
FIG. 45 shows a perspective view of a DNA optical storage system.
Figure 46A:
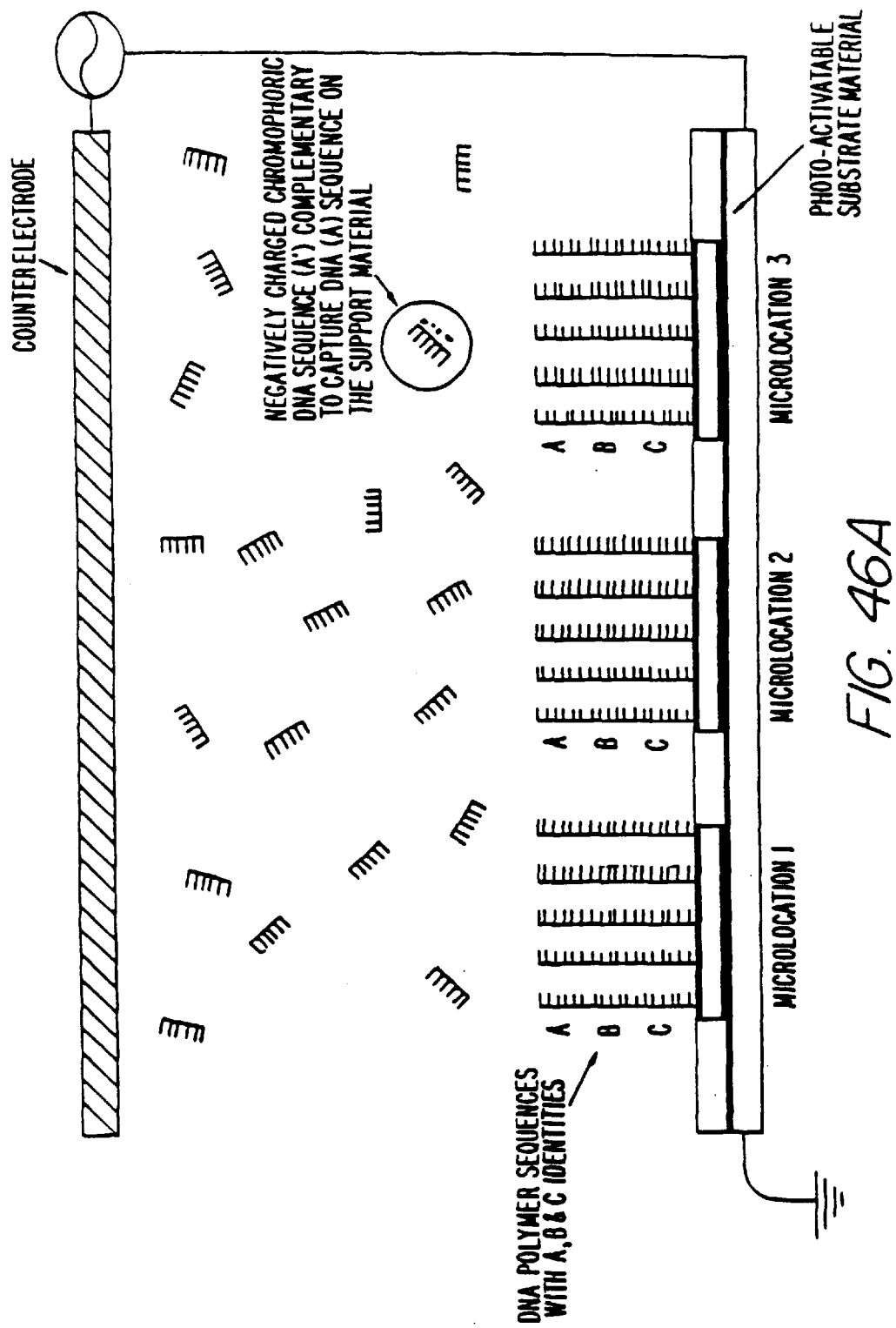
Figure 46C:
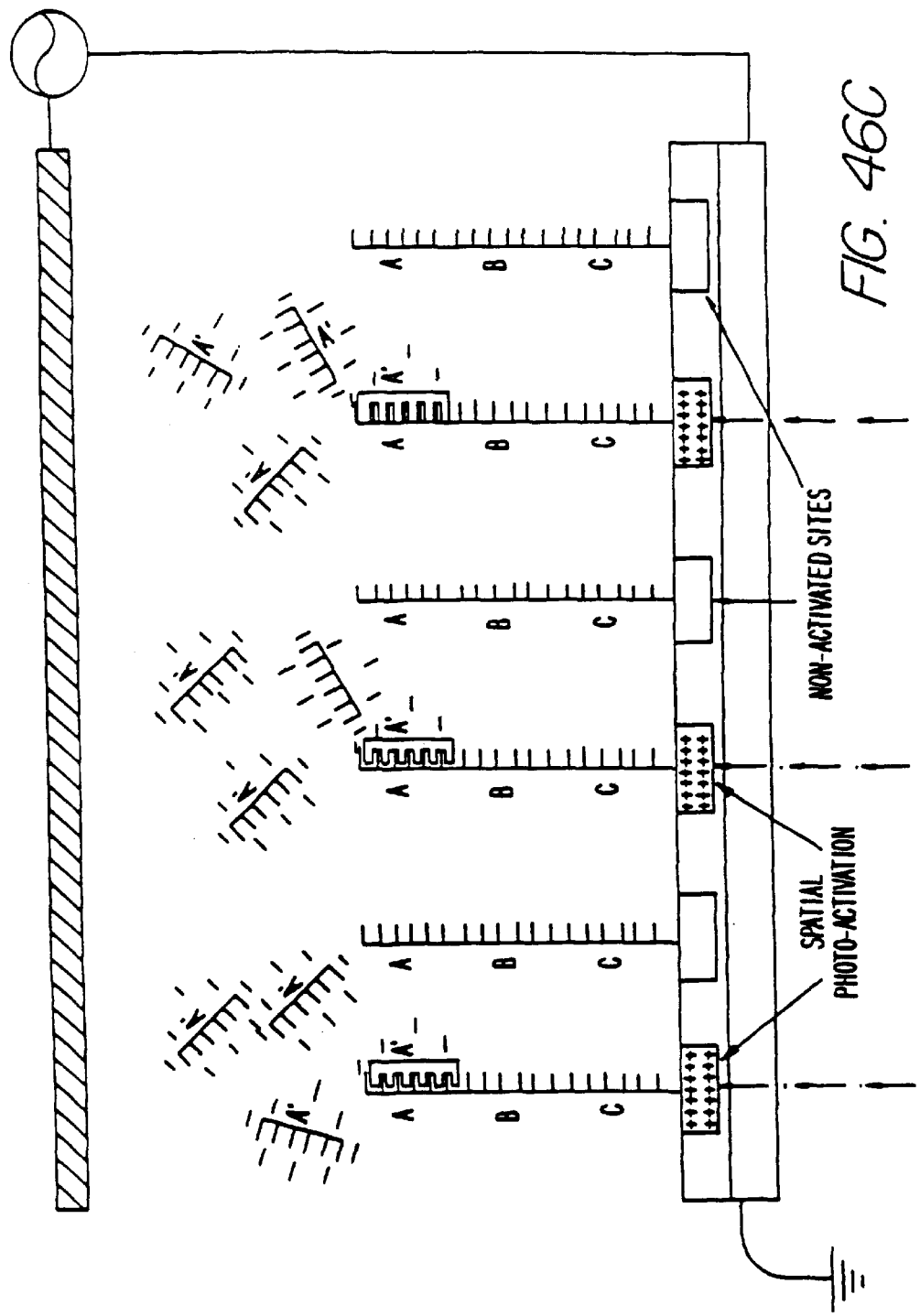
Figure 46D:
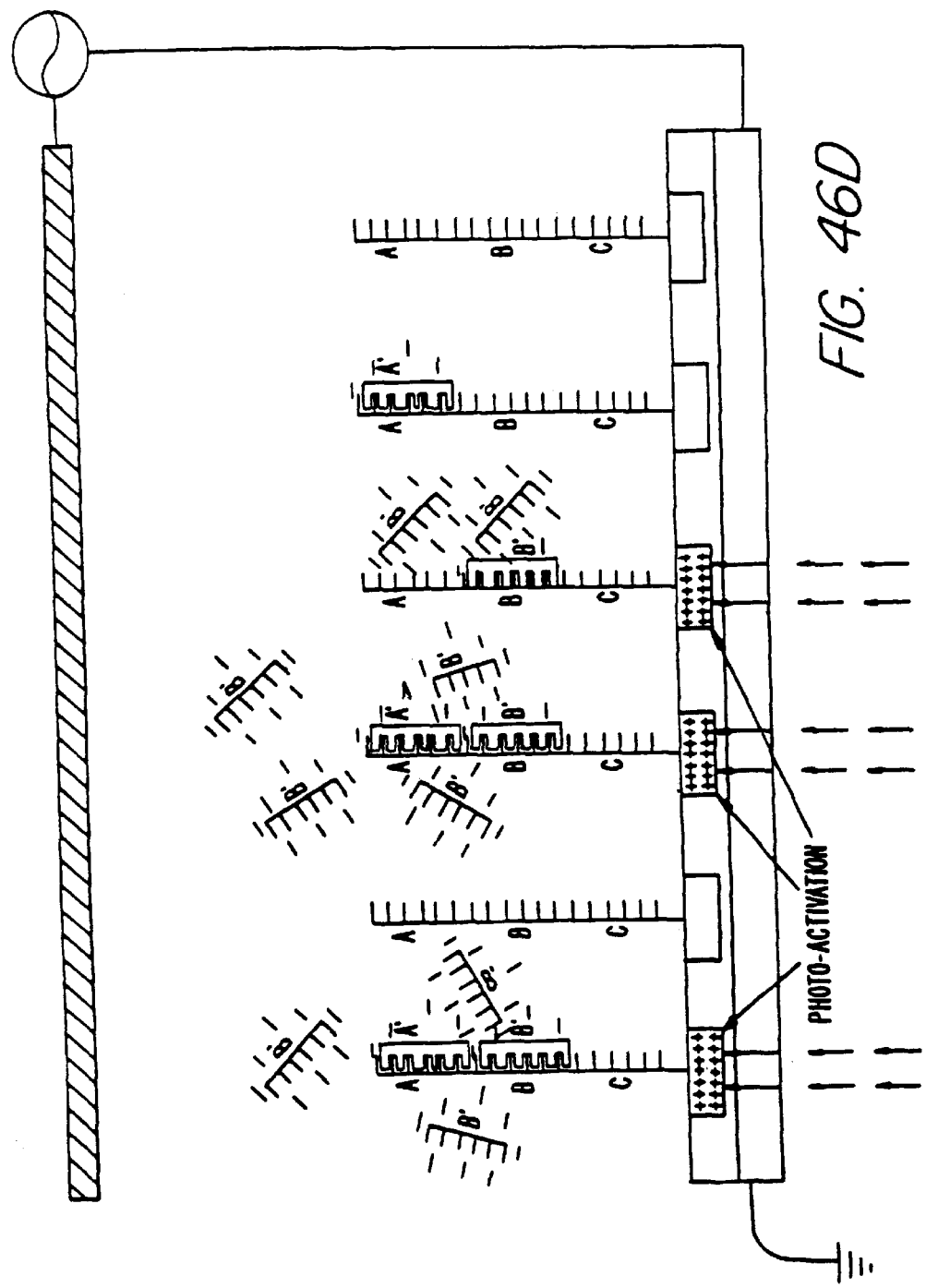
Figure 46E:
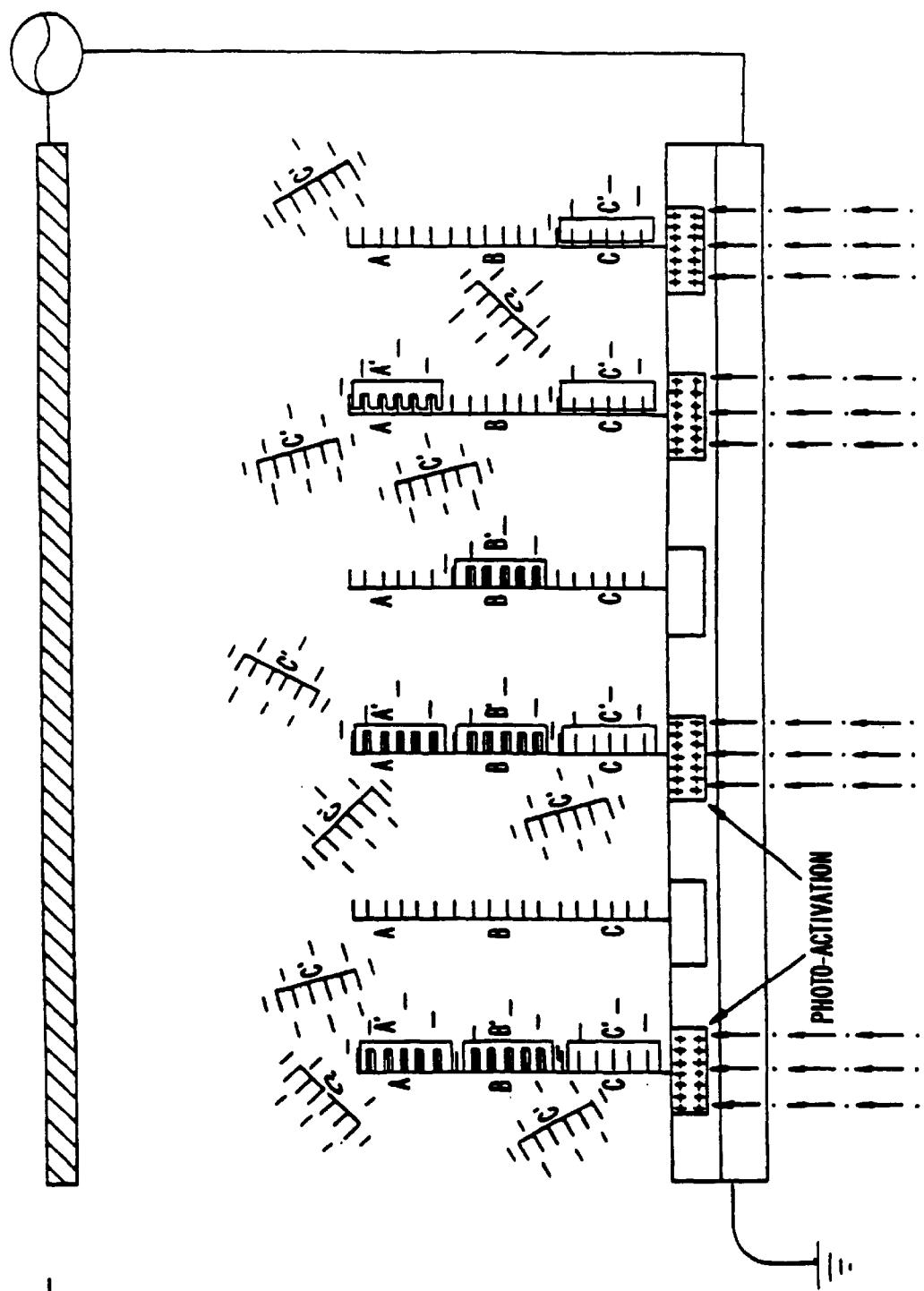

DNA polymers may be used for many photonic and electronic applications. One of the main applications using DNA polymers are for high density optical data storage media. In this application, chromophoric DNA polymers absorb light energy at a single wavelength and re-emit at predetermined multiple wavelengths. (See FIG. 45). In one aspect, these inventions relate to a method called photoelectronic write process. This process involve using spatial light addressing to a photoactive substrate material which creates microscopic electric fields, which then affect the selective transport and attachment of charged chromophoric (color) DNA's to these selected locations.

Principles of Operation

The basic principle involved in the photo/electronic write process is show in FIGS. 46.a and 46.b. The proposed write substrate would be a photoelectronic activated matrix material (e.g., a photoconductive film) onto which DNA polymer sequences would be attached. Each of these DNA sequences would have multiple identities. For the sake of illustration, FIG. 46A shows three photoactivated sites, which contain DNA sequences with three identities (A, B, & C). A solution containing chromophoric DNA with complementary identity (A') would be exposed to the substrate material, and a counter electrode would be positioned over the solution and lower substrate material. The specific microlocations on the substrate material can now be activated by spatial light addressing which would cause a charge to develop in the material at that location (see FIG. 46.b). The production of a charge produces an electric field in the solution which causes the attraction of oppositely charged molecules to the location, or will repel molecules of the same charge identity. Natural DNA would contain a net negative charge, and will migrate to a positively charged location. Synthetic DNA's can be made with net negative charge, net positive charge, or in a neutral state. FIG. 46.b shows the light activation of the center microlocation 2, with chromophoric DNA (A') migrating to this location and then binding (hybridizing) to the DNA (A) identity sequence position. When the electric field strength is high enough, the transport and concentration of the DNA chromophore units is extremely rapid; occurring in 1 to 2 seconds.

The process for producing multiple colors at a specific microlocations is shown in FIGS. 46.c through 46.f. FIG. 46.c shows a group of six microlocations, each of which contains a DNA polymer with A, B, and C sequence identities (only one capture strand is shown in these figures). Spatial light addressing of positions 1, 3, and 5 is carried out. Chromophoric DNA A' sequences (red) are transported, concentrated, and hybridized selectively to these locations. FIG. 46.d shows the process repeated for the next chromophoric DNA B' sequences (green). Spatial light addressing of positions 1, 3, and 4 are now carried out. Chromophoric DNA B' sequences are transported, concentrated, and hybridized selectively to these locations. FIG. 46.e shows the process repeated for the next chromophoric DNA C' sequences (blue). Spatial light addressing of positions 1, 3, 5 and 6, are now carried out. Chromophoric DNA C' sequences are transported, concentrated, and hybridized selectively to these locations. The write process being complete, FIG. 46.f shows the final optical material which now has chromophore DNA A'/B'/C' (red/green/blue) at microlocations 1 and 3, chromophoric DNA A'/C' (red/blue) at microlocation 5, chromophoric DNA B' (green) at microlocation 4, chromophoric DNA C' (blue) at microlocation 6, and no chromophoric DNA (no color) at microlocation 2.

In addition to the spatial light activation of photoconductive materials, other alternatives exist. For example, electrode array devices may be switched by spatial light addressing. In yet another example, electrode arrays may be switched by electronics.

Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the appended claims.

We claim:

1. A method for fabrication of structures including nanoscale and microscale components comprising the steps of:

providing a microscale or nanoscale structure with a first specific DNA sequence on a first region of the structure and a second specific DNA sequence on a second region of the structure, the second specific DNA sequence having a net charge, the structure including said first and second specific DNA sequences having a non-uniform charge distribution, providing a host support having a third specific DNA sequence thereon, orienting the structure with the first and second specific DNA structures in an electric field so as to selectively orient the first DNA sequence or the second DNA sequence toward the third DNA sequence on the host support, and hybridizing the oriented first or second DNA sequence with the third DNA sequence.

2. The method of claim 1 for fabrication of structures wherein the multiple affinity surface identities are arranged in a polar fashion.

3. The method of claim 1 for fabrication of structures wherein the multiple affinity surface identities are arranged in a tetrahedral fashion.

4. The method for fabrication of structures of claim 1 wherein the first DNA sequence is complementary to the third DNA sequence.

5. The method for fabrication of structures of claim 1 wherein the first DNA sequence is hybridized with a fourth DNA specific sequence, the fourth DNA specific sequence in turn being complementary to the third DNA specific sequence, and hybridizable thereto.

6. A method for the fabrication of devices including microscale or nanoscale components comprising the steps of:

fabricating first microscale or nanoscale component devices on a first region of a support, said first component devices including at least a first specific DNA polymer sequence thereon and a non-nucleic acid component, releasing at least one first component device from the first support into a solution, electrophoretically transporting the released first component device to a second region of the support, and attaching the first component device to a selected location on the second region of the support, the second region of the support containing complementary DNA polymer sequences to the first specific DNA polymer sequence on the first component device, the attachment including at least hybridizing of the first specific DNA polymer sequence on the first component device and the complementary DNA polymer sequence on the second region of the support.

7. The method of claim 6 for the fabrication of devices wherein the step of releasing the device is performed by epitaxial lift-off.

8. The method of claim 6 for the fabrication of devices wherein the transporting is accomplished through a fluid.

9. The method of claim 8 for the fabrication of devices further including the step of drying at least the host support and attached device.

10. The method of claim 6 for the fabrication of devices wherein the transport is electrophoretic.

11. The method of claim 6 for the fabrication of devices wherein the attachment of devices to the host support is performed by grafting.

12. The method of claim 6 for the fabrication of devices wherein the second component device is attached to the first component device.

13. The method of claim 6 for the fabrication of devices wherein the host support is a microelectronic array.

14. The method of claim 6 for the fabrication of devices further including the step of forming contacts on the host support.

15. The method of claim 6 for the fabrication of devices wherein the released first component device is an electrical component structure.

16. The method of claim 6 for the fabrication of devices wherein the released first component device is a general component structure.

17. The method of claim 6 for the fabrication of devices wherein the transport is achieved by use of an electric field.

18. The method of claim 17 for the fabrication of devices wherein the electric field is an alternating current electric field.

19. The method of claim 16 for the fabrication of devices wherein the electric field is a direct current electric field.

20. The method of claim 16 for the fabrication of devices wherein the attachment of the released first component device to the host support is achieved at least in part by the use of an electric field.

21. A method for the fabrication of devices including microscale or nanoscale components comprising the steps of:

fabricating first and second microscale or nanoscale component devices on a common first support, said component devices including at least a specific DNA polymer sequence thereon and a non-nucleic acid component, releasing at least one first component device and at least one second component device from the first support into a solution, electrophoretically transporting the released first component device and second component device to a host support, and attaching the first component device and second component device to selected locations on the host support, the host support containing complementary DNA polymer sequences to the specific DNA polymer sequences on the component devices, the attachment including at least hybridization of the specific DNA polymer sequence on the component devices and the complementary DNA polymer sequence on the host support.

22. The method of claim 21 for the fabrication of devices wherein the step of releasing the device is performed by epitaxial lift-off.

23. The method of claim 21 for the fabrication of devices wherein the transporting is accomplished through a fluid.

24. The method of claim 23 for the fabrication of devices further including the step of drying at least the host support and attached device.

25. The method of claim 21 for the fabrication of devices wherein the transport is electrophoretic.

26. The method of claim 21 for the fabrication of devices wherein the attachment of devices to the host support is performed by grafting.

27. The method of claim 21 for the fabrication of devices wherein the second component device is attached to the first component device.

28. The method of claim 21 for the fabrication of devices wherein the host support is a microelectronic array.

29. The method of claim 21 for the fabrication of devices wherein the first support and host support are physically distinct structures.

30. The method of claim 21 for the fabrication of devices wherein the first support and the host support are separate regions of a common structure.

31. The method of claim 21 for the fabrication of devices further including the step of forming contacts on the host support.

32. The method of claim 21 for the fabrication of devices wherein the released first component device is an electrical component structure.

33. The method of claim 21 for the fabrication of devices wherein the released first component device is a general component structure.

34. The method of claim 21 for the fabrication of devices wherein the transport is achieved by use of an electric field.

35. The method of claim 34 for the fabrication of devices wherein the electric field is an alternating current electric field.

36. The method of claim 34 for the fabrication of devices wherein the electric field is a direct current electric field.

37. The method of claim 34 for the fabrication of devices wherein the attachment of the released first component device to the host support is achieved at least in part by the use of an electric field.

38. A method for the fabrication of a photonic bandgap devices including microscale or nanoscale components comprising the steps of:
    fabricating first microscale or nanoscale component devices on a first support, said first component devices including at least a first specific DNA polymer sequence thereon and a non-nucleic acid component,
    releasing at least one first component device from the first support into a solution,
    electrophoretically transporting the released first component device to a host support,
    attaching the first component device to a selected location on the host support, the host support containing complementary DNA polymer sequences to the first specific DNA polymer sequence on the first component device, the attachment including at least hybridization of the first specific DNA polymer sequence on the first component device and the complementary DNA polymer sequence on the host support, and
    forming a structure on the first component device after the first component device is attached to the host support to form a photonic bandgap device.

39. The method of claim 38 for the fabrication of devices wherein the step of releasing the device is performed by epitaxial lift-off.

40. The method of claim 38 for the fabrication of devices wherein the transporting is accomplished through a fluid.

41. The method of claim 40 for the fabrication of devices further including the step of drying at least the host support and attached device.

42. The method of claim 38 for the fabrication of devices wherein the transport is electrophoretic.

43. The method of claim 38 for the fabrication of devices wherein the attachment of devices to the host support is performed by grafting.

44. The method of claim 38 for the fabrication of devices further including the steps of:
    fabricating second component devices on a second support,
    releasing at least one second component device from the second support,
    transporting the second component device to the host support, and
    attaching the second component device on the host support.

45. The method of claim 44 for the fabrication of devices wherein the second component device is attached to the first component device.

46. The method of claim 44 for the fabrication of devices wherein the host support is a microelectronic array.

47. The method of claim 38 for the fabrication of devices wherein the first support and host support are physically distinct structures.

48. The method of claim 38 for the fabrication of devices wherein the first support and the host support are separate regions of a common structure.

49. The method of claim 38 for the fabrication of devices further including the step of forming contacts on the host support.

50. The method of claim 38 for the fabrication of devices wherein the released first component device is an electrical component structure.

51. The method of claim 38 for the fabrication of devices wherein the released first component device is a general component structure.

52. The method of claim 38 for the fabrication of devices wherein the transport is achieved by use of an electric field.

53. The method of claim 52 for the fabrication of devices wherein the electric field is an alternating current electric field.

54. The method of claim 52 for the fabrication of devices wherein the electric field is a direct current electric field.

55. The method of claim 52 for the fabrication of devices wherein the attachment of the released first component device to the host support is achieved at least in part by the use of an electric field.

56. The method of claim 1 for fabrication of structures wherein the multiple affinity surface identities are arranged in a polar fashion.

57. The method of claim 1 for fabrication of structures wherein the multiple affinity surface identities are arranged in a equitorial fashion.

58. A method for the fabrication of devices including microscale or nanoscale components comprising the steps of:
    fabricating first microscale or nanoscale component devices on a first support, said first component devices including at least a first specific DNA polymer sequence thereon and a non-nucleic acid component, releasing at least one first component device from the first support into a solution by epitaxial lift-off, electrophoretically transporting the released first component device to a host support, and attaching the first component device to a selected location on the host support, the host support containing complementary DNA polymer sequences to the first specific DNA polymer sequence on the first component device, the attachment including at least hybridization of the first specific DNA polymer sequence on the first component device and the complementary DNA polymer sequence on the host support.

59. The method of claim 58 for the fabrication of devices wherein the released first component device is a display element.

60. The method of claim 58 for the fabrication of devices wherein the attachment of devices to the host support is performed by grafting.

61. The method of claim 58 for the fabrication of devices further including the steps of:

fabricating second component devices on a second support, releasing at least one second component device from the second support, transporting the second component device to the host support, and attaching the second component device on the host support.

62. The method of claim 61 for the fabrication of devices wherein the second component device is attached to the first component device.

63. The method of claim 61 for the fabrication of devices wherein the host support is a microelectronic array.

64. The method of claim 61 for the fabrication of devices wherein the first support and the second support are separate regions of a common structure.

65. The method of claim 58 for the fabrication of devices wherein the released first component devices include emitters and the host device is an emitter array.

66. The method of claim 58 for the fabrication of devices including the further step of forming a structure on the first component device after the first component device is attached to the host support.

67. The method of claim 66 for the fabrication of devices wherein the combined first component device and attached structure forms a photonic band gap device.

68. The method of claim 58 for the fabrication of devices further including the step of forming contacts on the host support.

69. The method of claim 68 for the fabrication of devices wherein the contacts are formed by transporting and attaching conductive materials on the host support.

70. The method of claim 58 for the fabrication of devices wherein the released first component device is a component semiconductor device.

71. The method of claim 58 for the fabrication of devices wherein the released first component device is a component optoelectronic device.

72. The method of claim 58 for the fabrication of devices wherein the released first component device is a component electronic device.

73. The method of claim 58 for the fabrication of devices wherein the released first component device is an optical component structure.

74. The method of claim 58 for the fabrication of devices wherein the released first component device is an electrical component structure.

75. The method of claim 58 for the fabrication of devices wherein the transport is achieved by use of an electric field.

76. The method of claim 75 for the fabrication of devices wherein the electric field is an alternating current electric field.

77. The method of claim 75 for the fabrication of devices wherein the electric field is a direct current electric field.

78. The method of claim 75 for the fabrication of devices wherein the attachment of the released first component device to the host support is achieved at least in part by the use of an electric field.

79. The method of claim 61 for the fabrication of devices wherein n-component devices are attached to n-separate supports, where n>2.

80. A method for the fabrication of devices including microscale or nanoscale components comprising the steps of:

fabricating first microscale or nanoscale component devices on a first support, said first component devices including at least a first specific DNA polymer sequence thereon and a non-nucleic acid component, releasing at least one first component device from the first support into a solution, electrophoretically transporting the released first component device to a host support through a fluid, and attaching the first component device to a selected location on the host support, the host support containing complementary DNA polymer sequences to the first specific DNA polymer sequence on the first component device, the attachment including at least hybridization of the first specific DNA polymer sequence on the first component device and the complementary DNA polymer sequence on the host support, and drying at least the host support and attached device.

81. The method of claim 80 for the fabrication of devices wherein the released first component device is a laser.

82. The method of claim 80 for the fabrication of devices wherein the released first component device is a display element.

83. The method of claim 82 for the fabrication of devices wherein the display element is an active display element.

84. The method of claim 80 for the fabrication of devices wherein the step of releasing the device is performed by epitaxial lift-off.

85. The method of claim 80 for the fabrication of devices further including the steps of:

fabricating second component devices on a second support, releasing at least one second component device from the second support, transporting the second component device to the host support, and attaching the second component device on the host support.

86. The method of claim 85 for the fabrication of devices wherein the second component device is attached to the first component device.

87. The method of claim 85 for the fabrication of devices wherein the host support is a microelectronic array.

88. The method of claim 80 for the fabrication of devices wherein the released first component devices include emitters and the host device is an emitter array.

89. The method of claim 80 for the fabrication of devices including the further step of forming a structure on the first component device after the first component device is attached to the host support.

90. The method of claim 89 for the fabrication of devices wherein the combined first component device and attached structure forms a photonic band gap device.

91. The method of claim 80 for the fabrication of devices wherein the host support is a microelectronic array.

92. The method of claim 80 for the fabrication of devices wherein the first support comprises a host board.

93. The method of claim 80 for the fabrication of devices wherein the released first component device is a component semiconductor device.

94. The method of claim 80 for the fabrication of devices wherein the released first component device is a component optoelectronic device.

95. The method of claim 80 for the fabrication of devices wherein the released first component device is a component electronic device.

96. The method of claim 80 for the fabrication of devices wherein the released first component device is an optical component structure.

97. The method of claim 80 for the fabrication of devices wherein the released first component device is an electrical component structure.

98. The method of claim 80 for the fabrication of devices wherein the released first component device is a general component structure.

99. The method of claim 80 for the fabrication of devices wherein the transport is achieved by use of an electric field.

100. The method of claim 99 or the fabrication of devices wherein the electric field is an alternating current electric field.

101. The method of claim 99 for the fabrication of devices wherein the electric field is a direct current electric field.

102. A method for the fabrication of devices including microscale or nanoscale components comprising the steps of:

fabricating first microscale or nanoscale component devices on a first support, said first component devices including at least a first specific DNA polymer sequence thereon and a non-nucleic acid component, releasing at least one first component device from the first support into a solution, electrophoretically transporting the released first component device to a host support, and attaching the first component device to a selected location on the host support, wherein the host support is a microelectronic array containing complementary DNA polymer sequences to the first specific DNA polymer sequence on the first component device, the attachment including at least hybridization of the first specific DNA polymer sequence on the first component device and the complementary DNA polymer sequence on the host support.

103. The method of claim 102 for the fabrication of devices wherein the released first component device is a laser.

104. The method of claim 102 for the fabrication of devices wherein the released first component device is a display element.

105. The method of claim 104 for the fabrication of devices wherein the display element is an active display element.

106. The method of claim 102 for the fabrication of devices further including the steps of:

fabricating second component devices on a second support, releasing at least one second component device from the second support, transporting the second component device to the host support, and attaching the second component device on the host support.

107. The method of claim 106 for the fabrication of devices wherein the second component device is attached to the first component device.

108. The method of claim 102 for the fabrication of devices wherein the first support and host support are physically distinct structures.

109. The method of claim 102 for the fabrication of devices wherein the first support and the host support are separate regions of a common structure.

110. The method of claim 106 for the fabrication of devices wherein the first support and the second support are physically distinct structures.

111. The method of claim 106 for the fabrication of devices wherein the first support and the second support are separate regions of a common structure.

112. The method of claim 102 for the fabrication of devices wherein the released first component devices include emitters and the host device is an emitter array.

113. The method of claim 102 for the fabrication of devices wherein the released first component devices include chromophoric memory units and the device is an optical memory.

114. The method of claim 102 for the fabrication of devices including the further step of forming a structure on the first component device after the first component device is attached to the host support.

115. The method of claim 114 for the fabrication of devices wherein the combined first component device and attached structure forms a photonic band gap device.

116. The method of claim 102 for the fabrication of devices wherein the released first component device is a component semiconductor device.

117. The method of claim 102 for the fabrication of devices wherein the released first component device is a component optoelectronic device.

118. The method of claim 102 for the fabrication of devices wherein the released first component device is a component electronic device.

119. The method of claim 102 for the fabrication of devices wherein the released first component device is an optical component structure.

120. The method of claim 102 for the fabrication of devices wherein the released first component device is an electrical component structure.

121. The method of claim 102 for the fabrication of devices wherein the released first component device is a general component structure.

122. The method of claim 121 for the fabrication of devices wherein the general component structure is a nanobead.

123. The method of claim 121 for the fabrication of devices wherein the general component structure is a nanoparticle.

124. The method of claim 102 for the fabrication of devices wherein the transport is achieved by use of an electric field.

125. The method of claim 124 for the fabrication of devices wherein the attachment of the released first component device to the host support is achieved at least in part by the use of an electric field.

126. The method of claim 106 for the fabrication of devices wherein n-component devices are attached to n-separate supports, where n>2.

\* \* \* \* \*

SEQUENCE LISTING (1) GENERAL INFORMATION:

(iii) NUMBER OF SEQUENCES:    4

(2) INFORMATION FOR SEQ ID NO:    1:

(i) SEQUENCE CHARACTERISTICS:
        (A) LENGTH:                  20
        (B) TYPE:                    nucleic acid
        (C) STRANDEDNESS:        single
        (D) TOPOLOGY:              linear (ii) SEQUENCE DESCRIPTION: SEQ ID NO: 1:

GCACCGATTC GATACCGTAG                                  20

(2) INFORMATION FOR SEQ ID NO:    2:

(i) SEQUENCE CHARACTERISTICS:
        (A) LENGTH:                  20
        (B) TYPE:                    nucleic acid
        (C) STRANDEDNESS:        single
        (D) TOPOLOGY:              linear (ii) SEQUENCE DESCRIPTION: SEQ ID NO: 2:

CTACGGTATC GAATCGGTGC                                  20

(2) INFORMATION FOR SEQ ID NO:    3:

(i) SEQUENCE CHARACTERISTICS:
        (A) LENGTH:                  20
        (B) TYPE:                    nucleic acid
        (C) STRANDEDNESS:        single
        (D) TOPOLOGY:              linear (ii) SEQUENCE DESCRIPTION: SEQ ID NO: 3:

TTCAGGCAAT TGATCGTACA                                  20

```
(2) INFORMATION FOR SEQ ID NO:      4:

(i) SEQUENCE CHARACTERISTICS:
        (A) LENGTH:                 20
        (B) TYPE:                   nucleic acid
        (C) STRANDEDNESS:           single
        (D) TOPOLOGY:               linear (ii) SEQUENCE DESCRIPTION: SEQ ID NO: 4:

TGTACGATCA ATTGCCTGAA                                          20
```